United States Patent
Steese-Bradley et al.

(10) Patent No.: US 11,724,042 B2
(45) Date of Patent: *Aug. 15, 2023

(54) SYSTEM AND METHOD FOR SAFETY SYRINGE

(71) Applicant: CREDENCE MEDSYSTEMS, INC., Menlo Park, CA (US)

(72) Inventors: Gary Steese-Bradley, San Jose, CA (US); Stephen H. Diaz, Palo Alto, CA (US); Alan E. Shluzas, San Carlos, CA (US); John F. Shanley, Emerald Hills, CA (US); Jeff Tillack, Foster City, CA (US); Dan Thayer, Tustin, CA (US); John Merhige, Subury, MA (US)

(73) Assignee: Credence Medsystems, Inc., Menlo Park, CA (US)

( * ) Notice: Subject to any disclaimer, the term of this patent is extended or adjusted under 35 U.S.C. 154(b) by 394 days.

This patent is subject to a terminal disclaimer.

(21) Appl. No.: 17/121,414

(22) Filed: Dec. 14, 2020

(65) Prior Publication Data

US 2021/0121640 A1 Apr. 29, 2021

Related U.S. Application Data

(63) Continuation of application No. 15/801,259, filed on Nov. 1, 2017, now Pat. No. 10,864,330.
(Continued)

(51) Int. Cl.
*A61M 5/32* (2006.01)
*A61M 5/178* (2006.01)
(Continued)

(52) U.S. Cl.
CPC .......... *A61M 5/3221* (2013.01); *A61M 5/178* (2013.01); *A61M 5/2066* (2013.01);
(Continued)

(58) Field of Classification Search
CPC .. A61M 5/3137; A61M 5/178; A61M 5/2066; A61M 5/2448; A61M 5/28;
(Continued)

(56) References Cited

U.S. PATENT DOCUMENTS

| 2,653,607 A | 9/1953 | Vindin |
| 4,031,892 A | 6/1977 | Hurschman |

(Continued)

FOREIGN PATENT DOCUMENTS

| CN | 102573959 A | 7/2012 |
| WO | WO 2014/085118 | 6/2014 |
| WO | WO 2015/164839 | 10/2015 |

OTHER PUBLICATIONS

Final Office Action for U.S. Appl. No. 15/801,259 dated May 28, 2020.
(Continued)

*Primary Examiner* — Tiffany Legette
(74) *Attorney, Agent, or Firm* — Vista IP Law Group, LLP

(57) ABSTRACT

A system for mixing drug products and injecting includes a syringe body, proximal and distal stopper members disposed in the syringe body, a plunger member, and a needle hub assembly coupled to the distal needle interface of the syringe body. The proximal and distal stopper members form a proximal drug chamber between there between and a distal drug chamber between the distal stopper member and a distal end of the syringe body. The plunger member includes a needle retention feature, an energy-storage member, and an energy-storage member latching member all disposed in disposed in a plunger interior. First and second sizes of the respective proximal and distal drug chambers can be modified by movement of the proximal and distal stopper members relative to the syringe body. The needle is at least (Continued)

partially retractable into plunger interior upon manipulation of the plunger member relative to the syringe body.

19 Claims, 73 Drawing Sheets

Related U.S. Application Data

(60) Provisional application No. 62/542,230, filed on Aug. 7, 2017, provisional application No. 62/480,276, filed on Mar. 31, 2017, provisional application No. 62/431,382, filed on Dec. 7, 2016, provisional application No. 62/416,102, filed on Nov. 1, 2016.

(51) Int. Cl.
*A61M 5/24* (2006.01)
*A61M 5/20* (2006.01)
*A61M 5/28* (2006.01)
*A61M 5/315* (2006.01)
*A61M 5/31* (2006.01)
*A61J 1/20* (2006.01)

(52) U.S. Cl.
CPC ............ *A61M 5/2448* (2013.01); *A61M 5/28* (2013.01); *A61M 5/284* (2013.01); *A61M 5/3137* (2013.01); *A61M 5/3148* (2013.01); *A61M 5/31501* (2013.01); *A61M 5/31511* (2013.01); *A61M 5/31513* (2013.01); *A61M 5/3202* (2013.01); *A61M 5/322* (2013.01); *A61M 5/3234* (2013.01); *A61J 1/2006* (2015.05); *A61J 1/2096* (2013.01); *A61M 5/3232* (2013.01); *A61M 5/3293* (2013.01); *A61M 2005/323* (2013.01); *A61M 2005/3223* (2013.01); *A61M 2005/3231* (2013.01); *A61M 2005/3241* (2013.01)

(58) Field of Classification Search
CPC ................ A61M 5/284; A61M 5/3148; A61M 5/31501; A61M 5/31511; A61M 5/31513; A61M 5/3202; A61M 5/322; A61M 5/3221; A61M 5/3234; A61M 5/3232; A61M 5/3293; A61M 2005/3241; A61M 2005/3231; A61M 2005/323; A61M 2005/3223
See application file for complete search history.

(56) References Cited

U.S. PATENT DOCUMENTS

| | | |
|---|---|---|
| 5,549,561 A | 8/1996 | Hjertman |
| 9,814,842 B2 | 11/2017 | Diaz et al. |
| 2008/0140005 A1 | 6/2008 | Luo |
| 2011/0046603 A1 | 2/2011 | Felsovalyi et al. |
| 2012/0245530 A1 | 9/2012 | Oden et al. |
| 2013/0035664 A1 | 2/2013 | Mojdehbakhsh |
| 2013/0165860 A1 | 6/2013 | Doud et al. |
| 2015/0005706 A1 | 1/2015 | Diaz |
| 2015/0148748 A1 | 5/2015 | Shluzas |
| 2016/0206834 A1 | 7/2016 | Shluzas |
| 2018/0117260 A1 | 5/2018 | Shluzas |
| 2018/0133408 A1 | 5/2018 | Shluzas |

OTHER PUBLICATIONS

Non-Final Office Action for U.S. Appl. No. 15/801,259 dated Nov. 13, 2019.
Amendment Response to NFOA for U.S. Appl. No. 15/801,259 dated Feb. 13, 2020.
Amendment Response to FOA for U.S. Appl. No. 15/801,259 dated Jul. 27, 2020.
Notice of Allowance for U.S. Appl. No. 15/801,259 dated Aug. 11, 2020.
PCT International Search Report for PCT/US2017/059608, Applicant: Credence MedSystems, Inc., Form PCT/ISA/210 and 220, dated Apr. 10, 2018.
PCT Written Opinion of the International Search Authority for PCT/US2017/059608, Applicant: Credence MedSystems, Inc., Form PCT/ISA/237, dated Apr. 10, 2018.
PCT International Preliminary Report on Patentability (Chapter I of the Patent Cooperation Treaty) for PCT/US2017/059608, Applicant: Credence MedSystems, Inc., Form PCT/ISA/326 and 373, dated May 16, 2019.
Foreign OA for JP Patent Appln. No. 2019-522940 dated Dec. 8, 2020.
Foreign OA for JP Patent Appln. No. 2019-522940 dated May 18, 2021.
Foreign NOA for JP Patent Appln. No. 2019-522940 dated Oct. 12, 2021 (with English translation).
Foreign OA for JP Patent Appln. No. 2021-181853 dated Jul. 26, 2022.
Foreign OA for JP Patent Appln. No. 2021-181853 dated Jan. 10, 2023.
Foreign OA for CN Patent Appln. No. 201780080647.1 dated Feb. 20, 2021 (with English translation).
Foreign Response to OA for CN Patent Appln. No. 201780080647.1 dated Jul. 7, 2021.
Foreign OA for IN patent Appln. No. 201947020604 dated Jul. 26, 2021.
Foreign Response for JP Patent Appln. No. 2021-181853 dated Apr. 5, 2023.
Foreign Response for EP patent Appln. No. 17804727.0 dated Feb. 14, 2023.

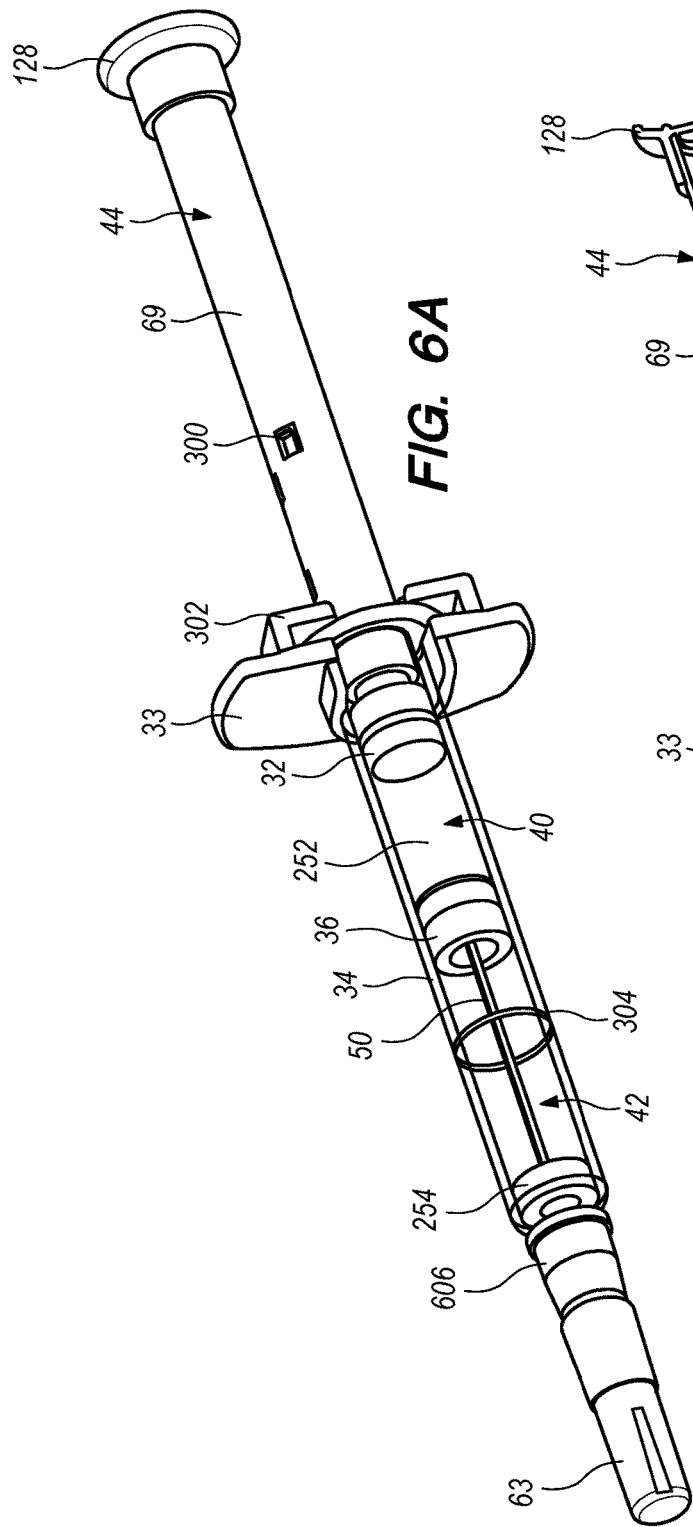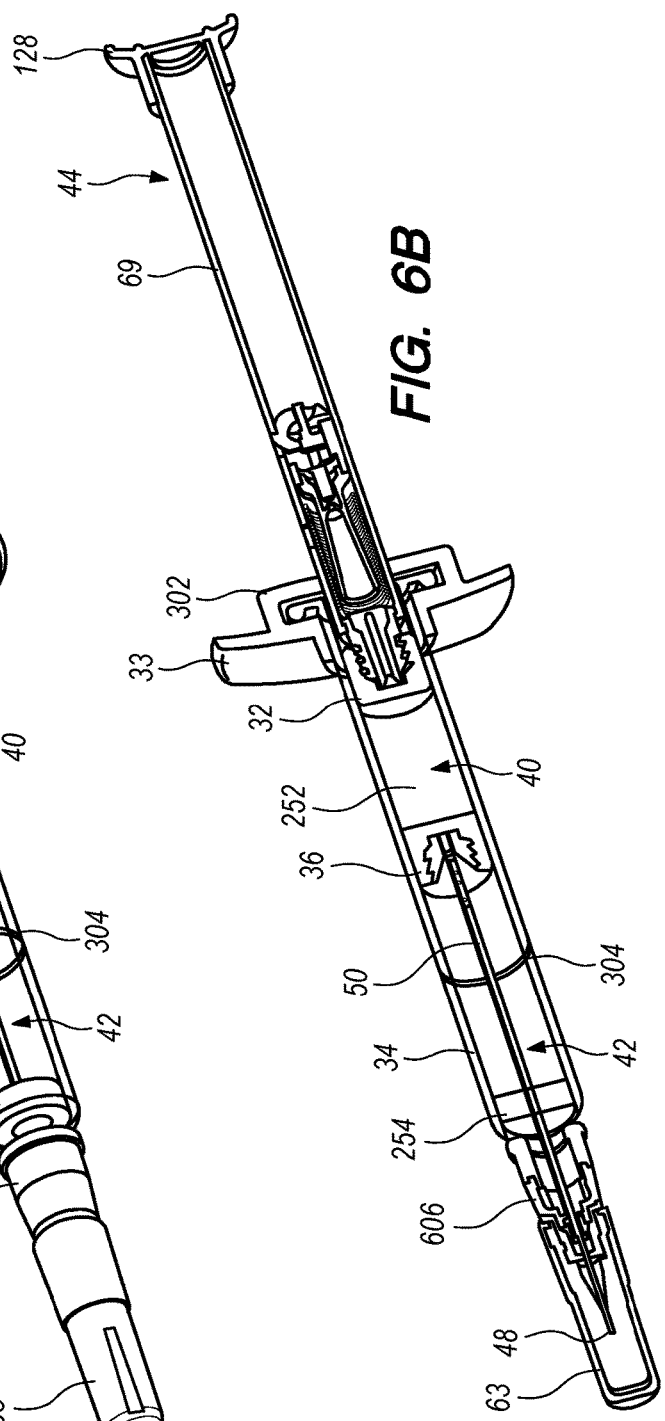

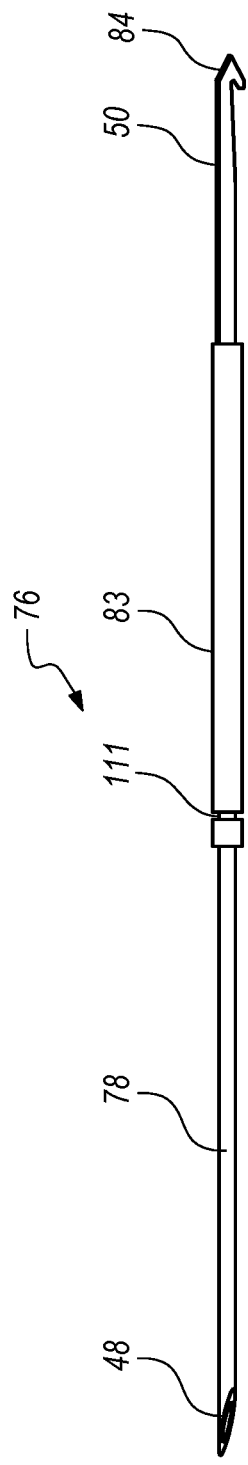
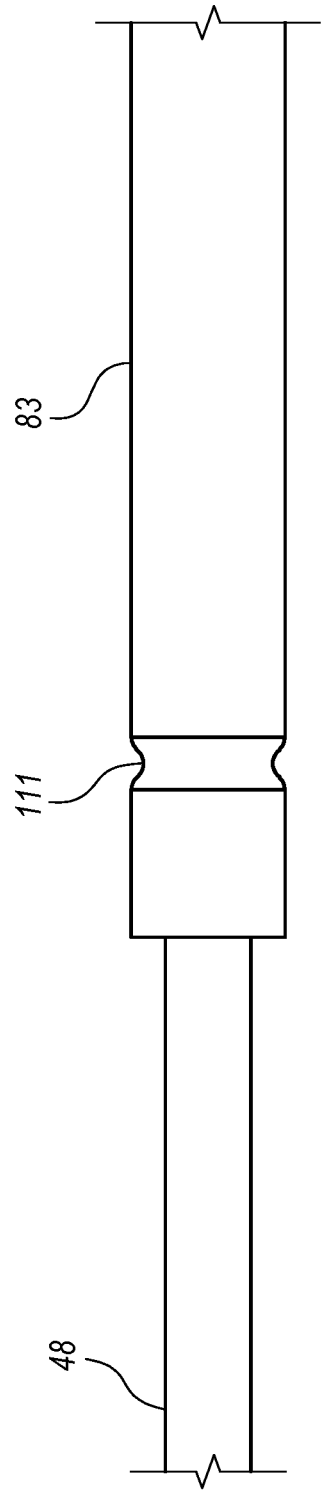
FIG. 6E
FIG. 6F

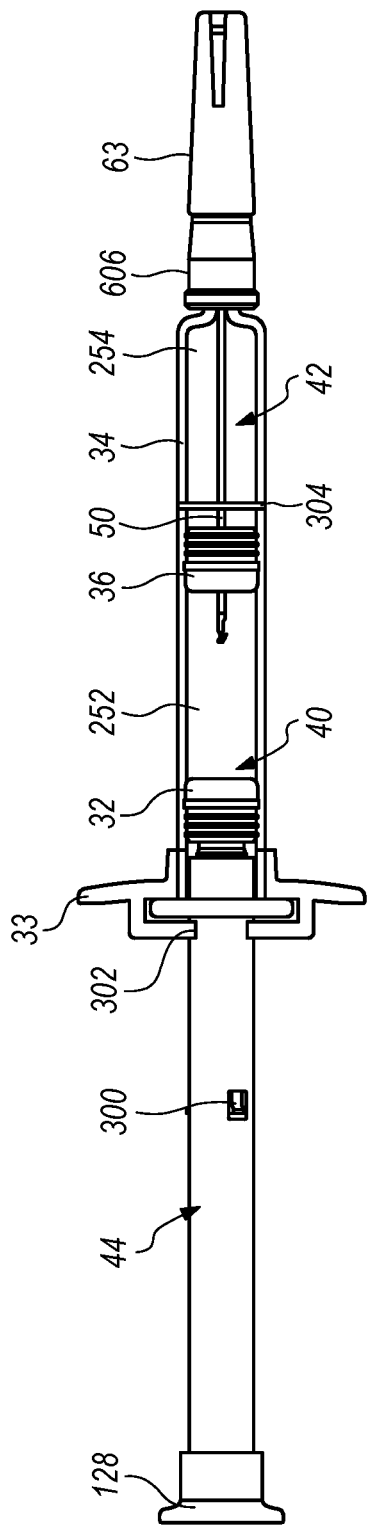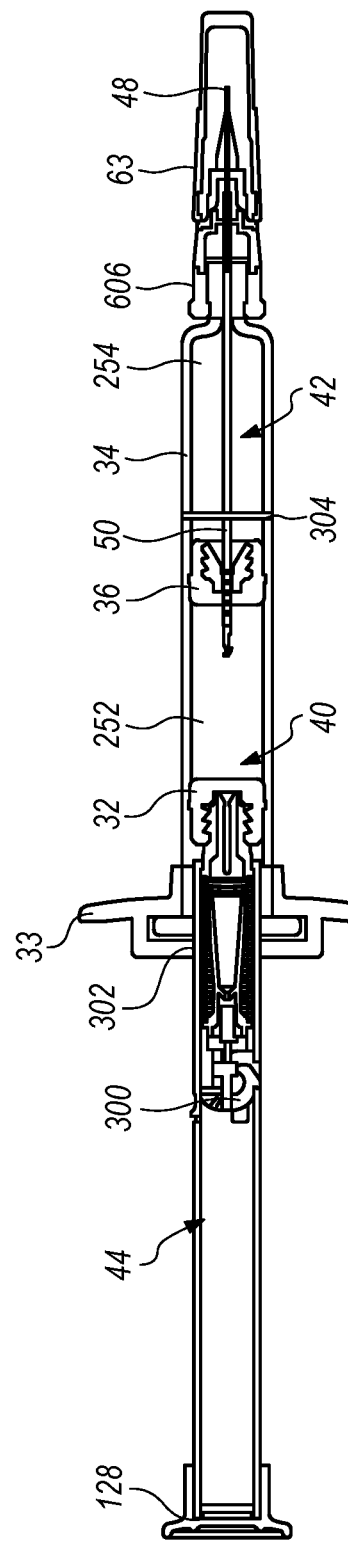

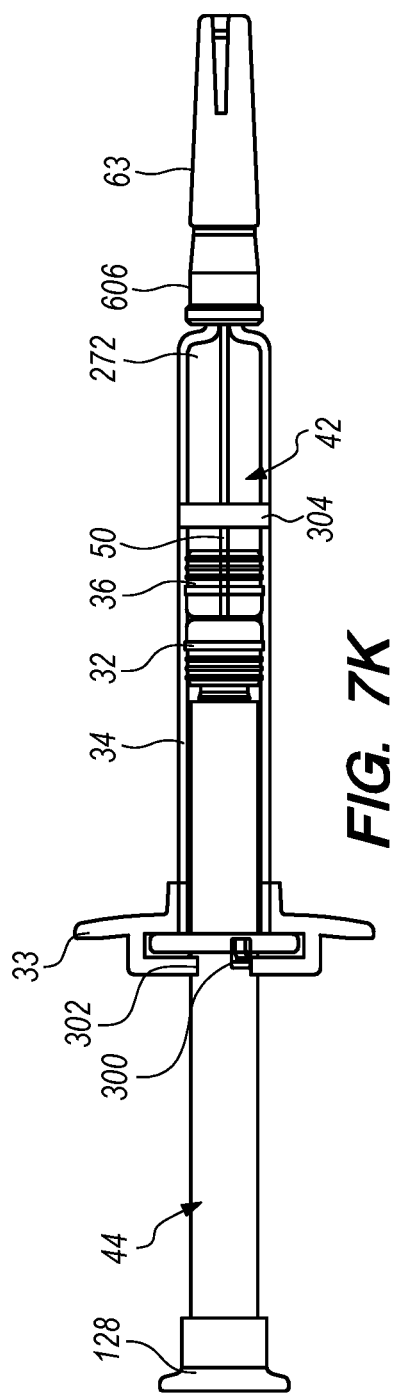
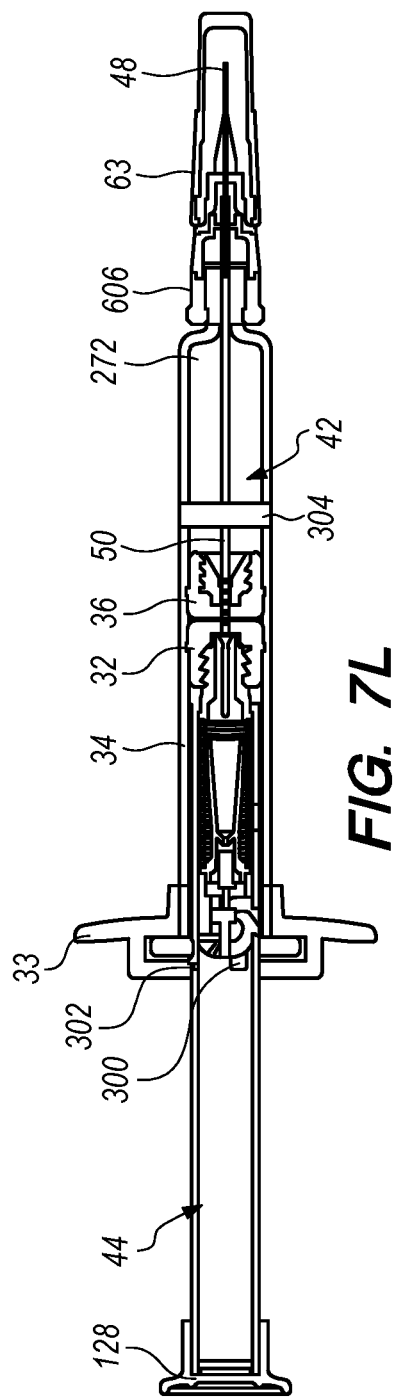

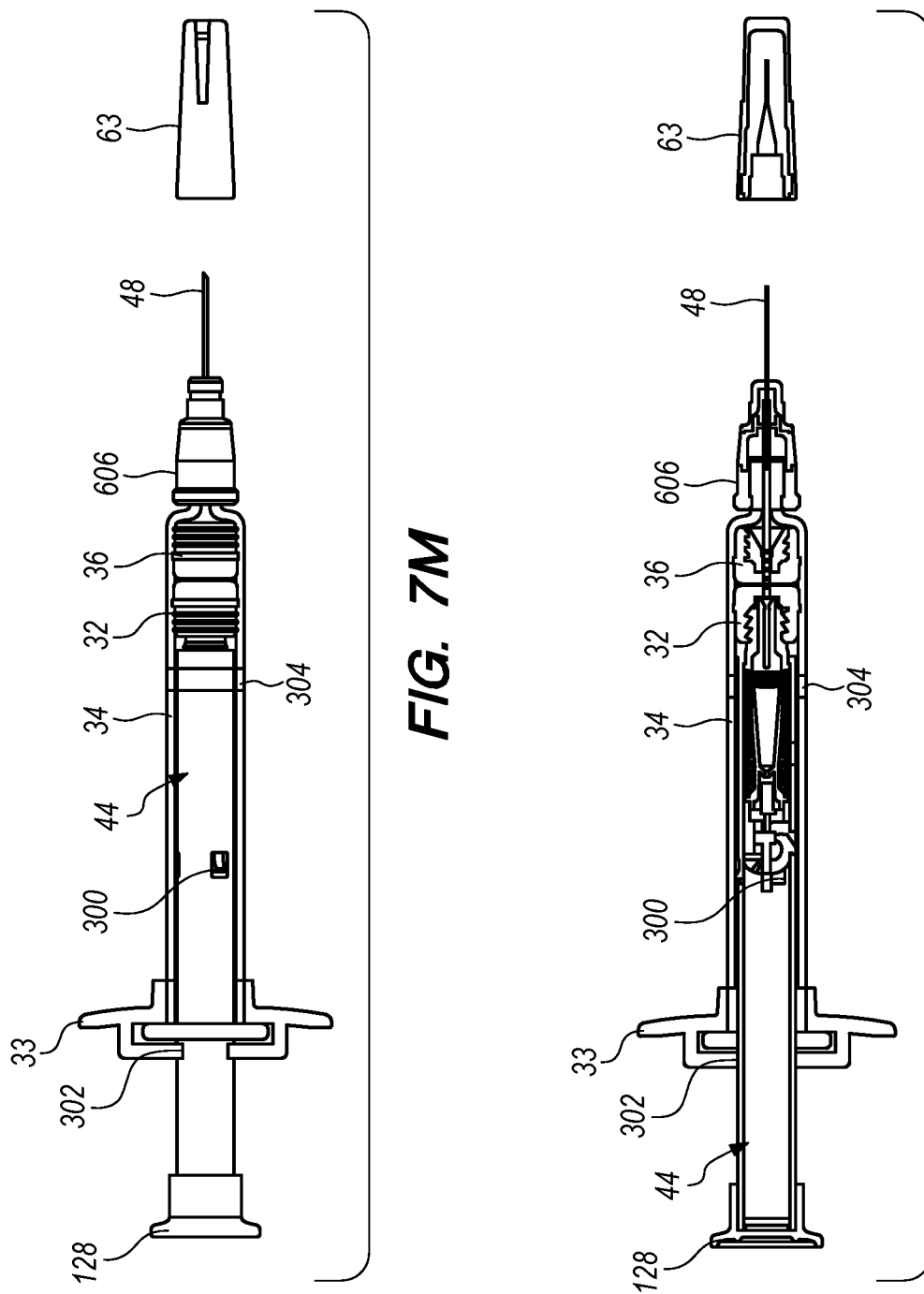

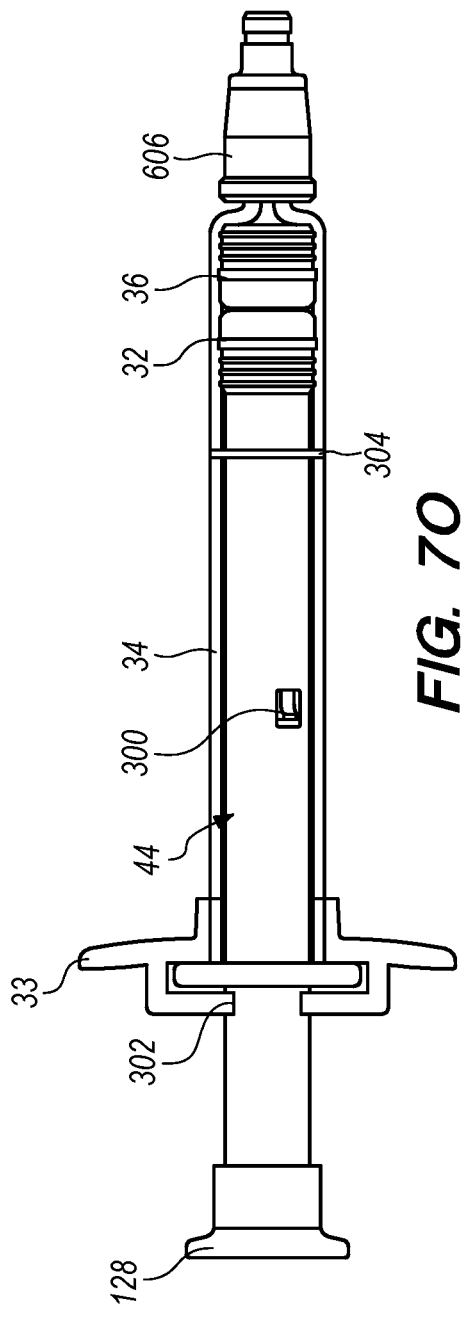
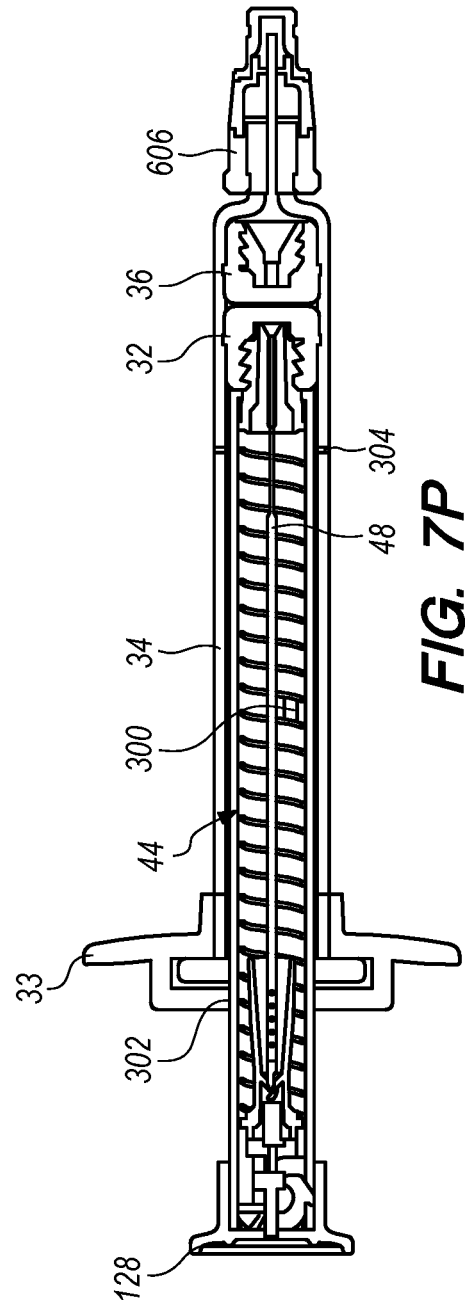
FIG. 7O
FIG. 7P

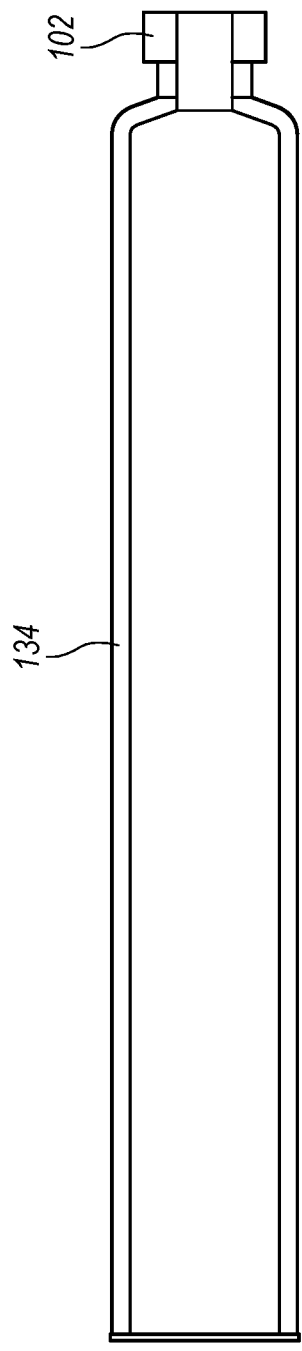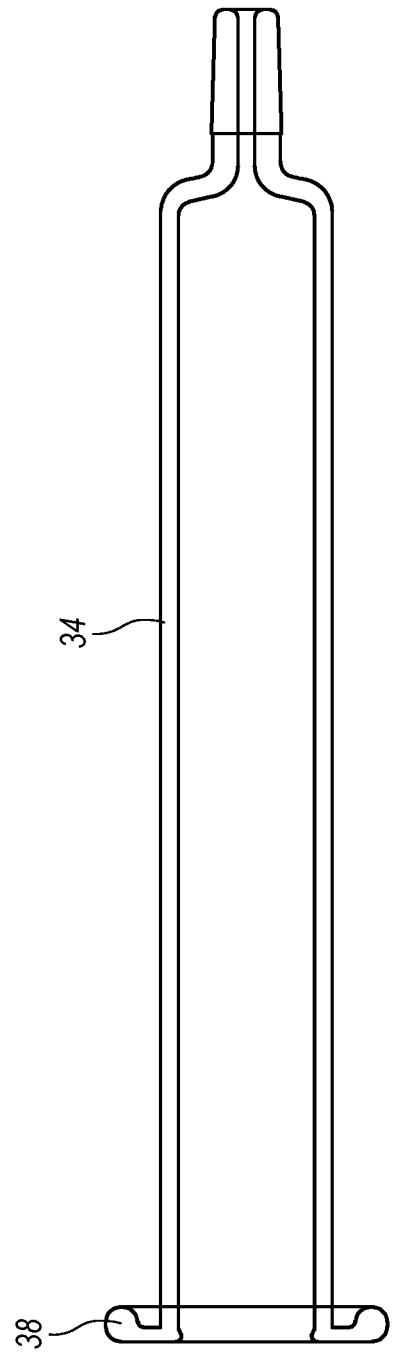

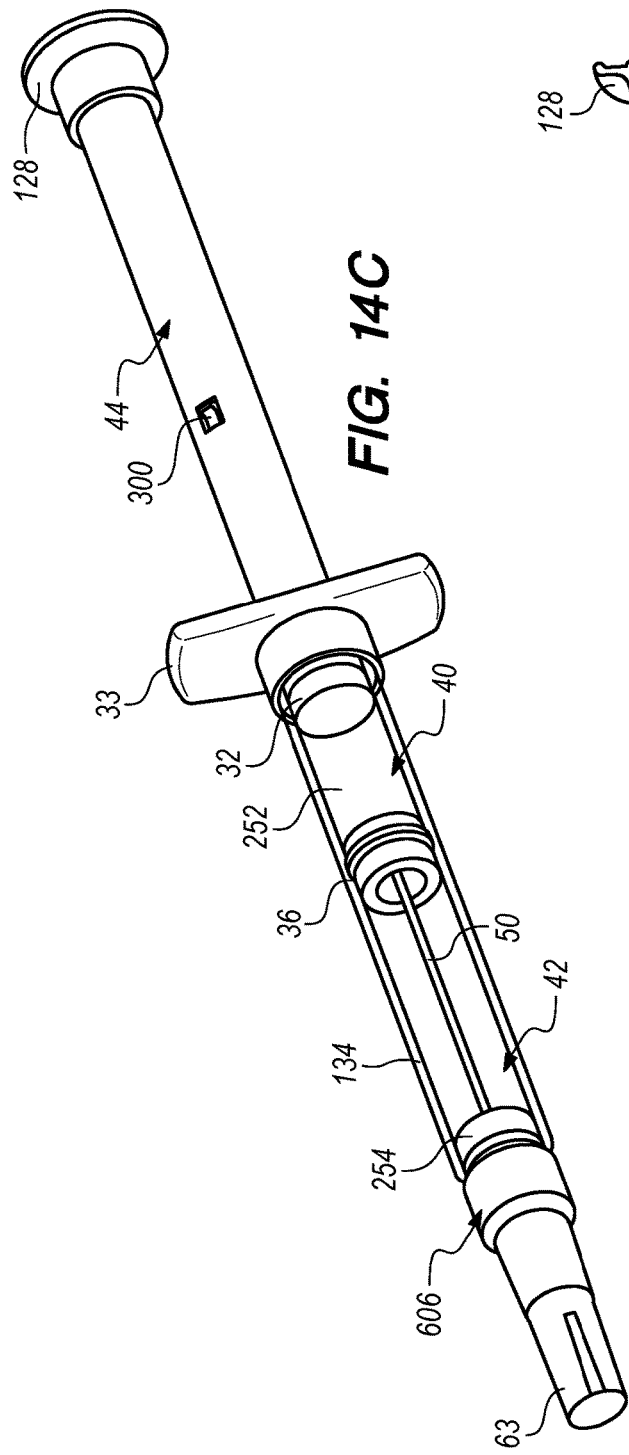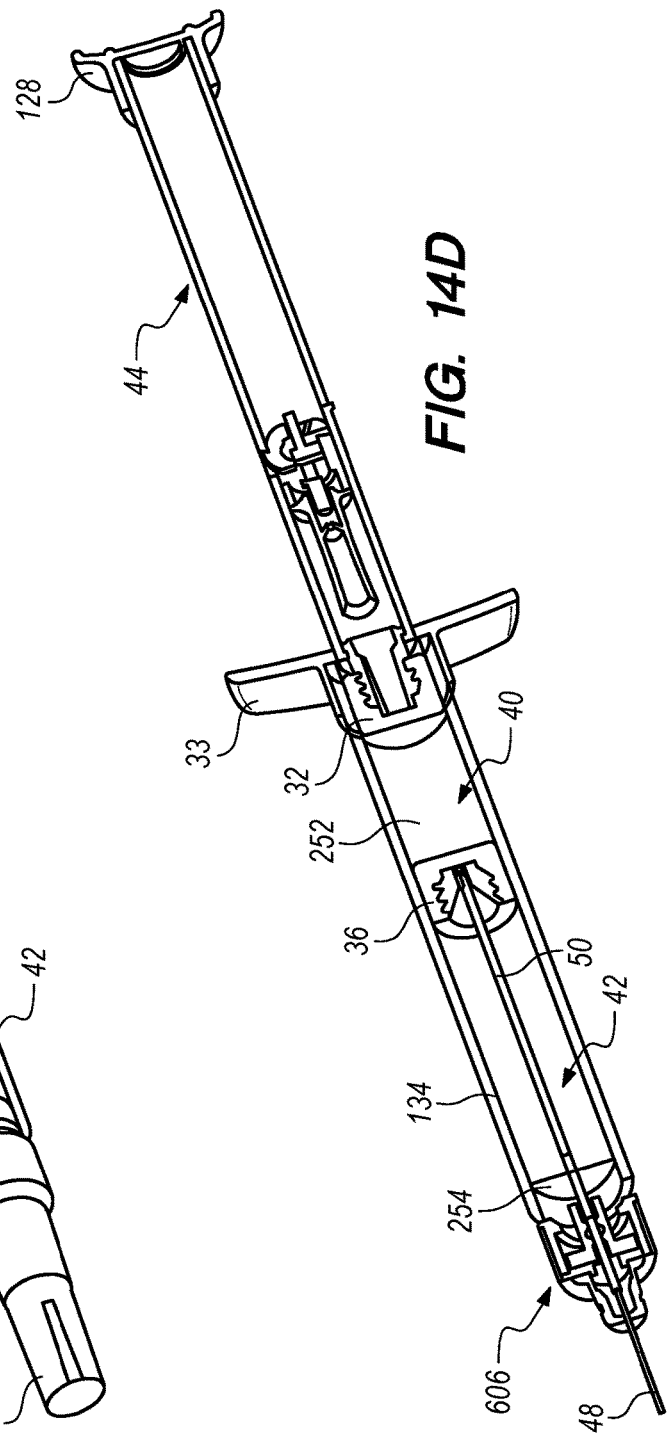

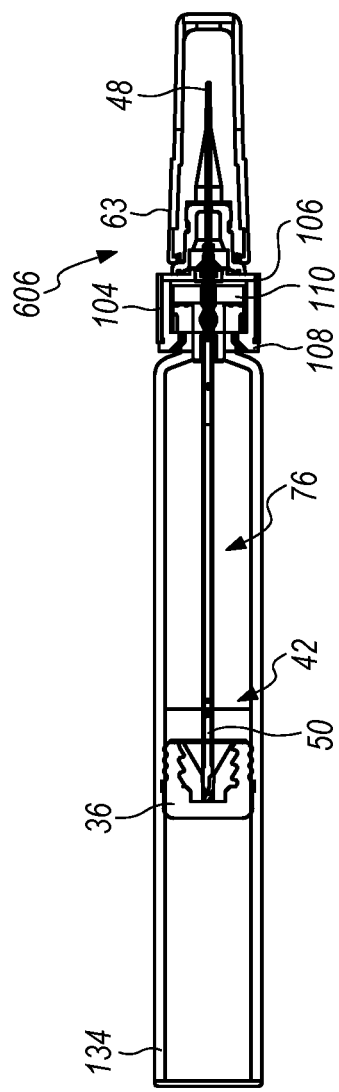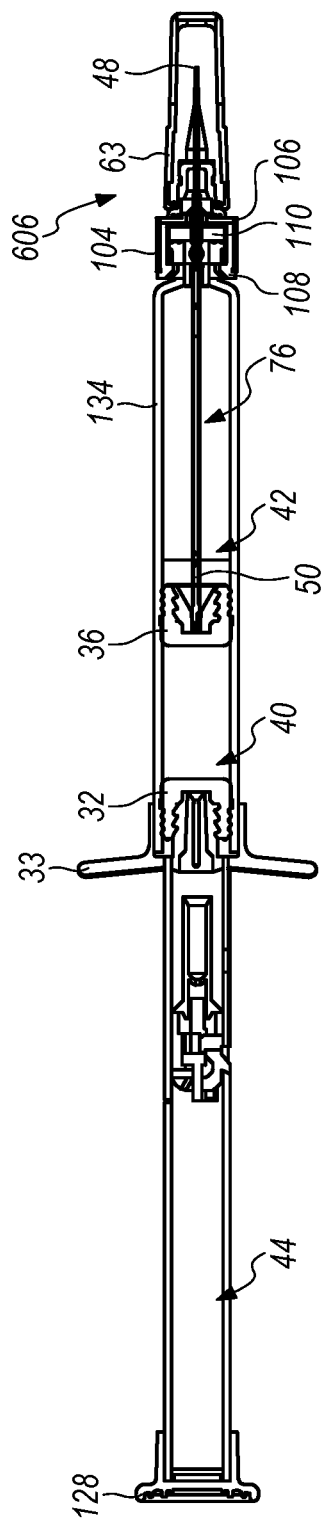
FIG. 16C
FIG. 16D

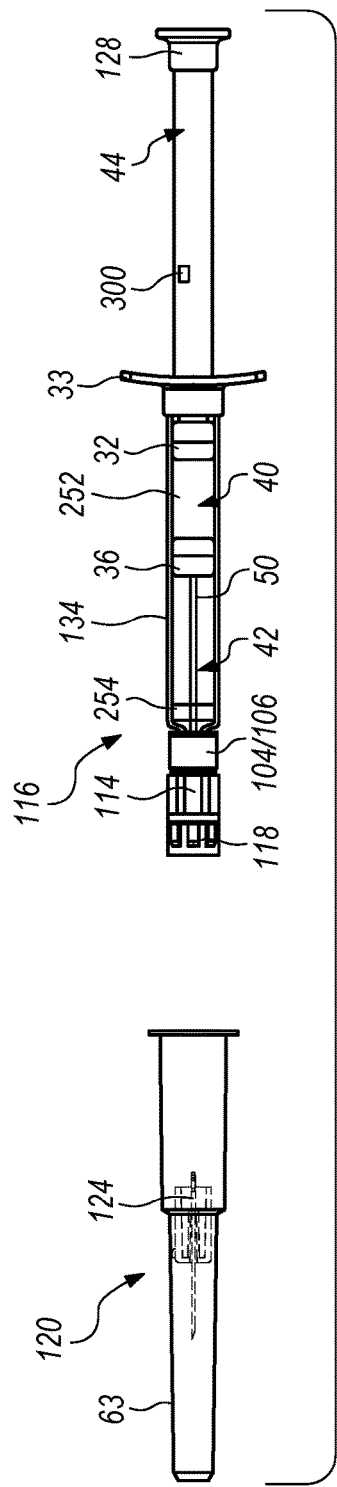
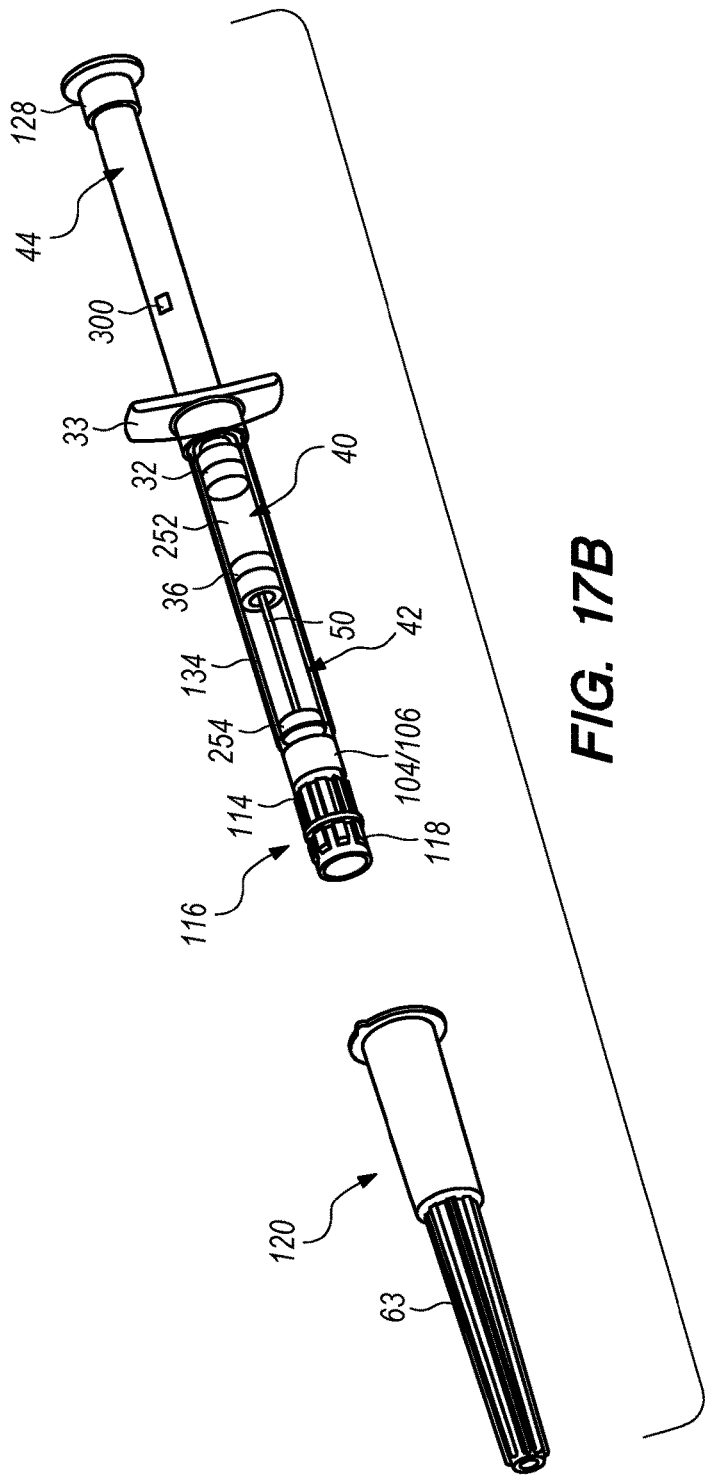
FIG. 17A
FIG. 17B

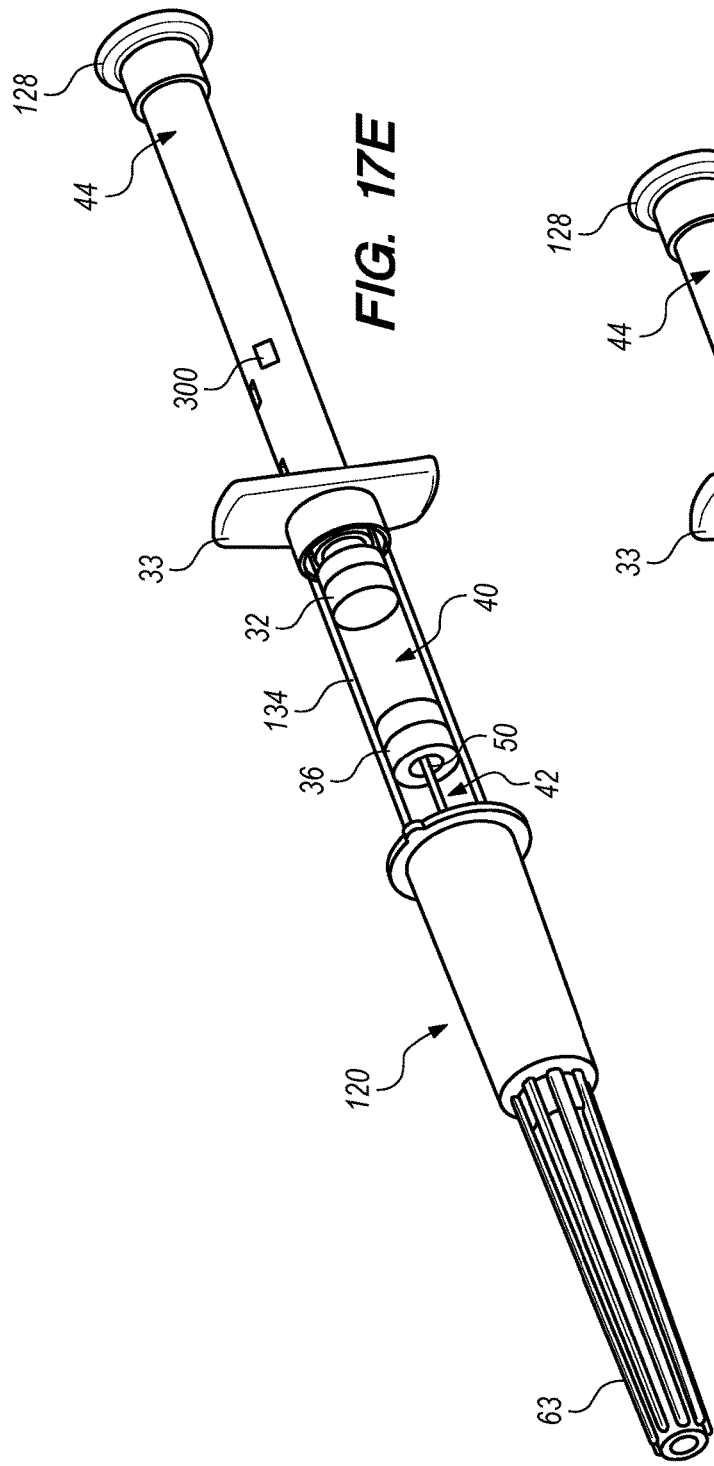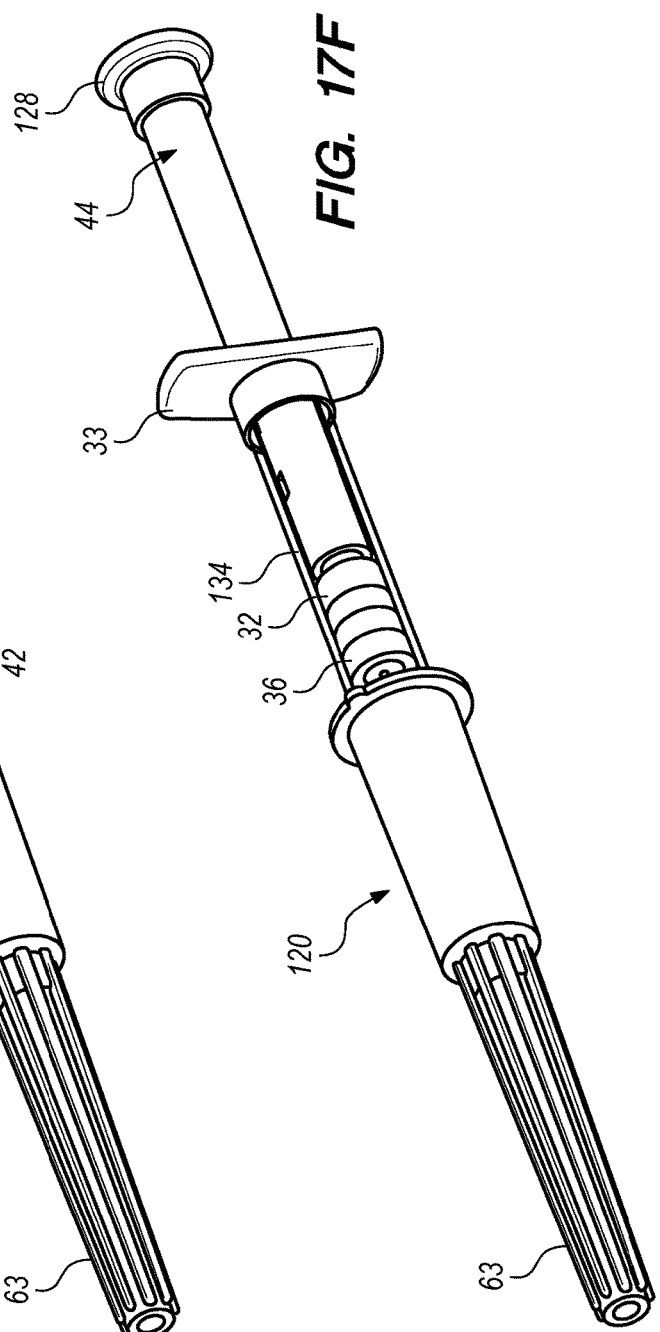

SYSTEM AND METHOD FOR SAFETY SYRINGE

CROSS-REFERENCE TO RELATED APPLICATION(S)

The present application is a continuation of U.S. patent application Ser. No. 15/801,259, filed on Nov. 1, 2017, and entitled "SYSTEM AND METHOD FOR SAFETY SYRINGE," which claims priority to (1) U.S. Provisional Patent Application Ser. No. 62/416,102, filed on Nov. 1, 2016 and entitled "SYSTEM AND METHOD FOR SAFETY SYRINGE"; (2) U.S. Provisional Patent Application Ser. No. 62/431,382, filed on Dec. 7, 2016 and entitled "SYSTEM AND METHOD FOR SAFETY SYRINGE"; (3) U.S. Provisional Patent Application Ser. No. 62/480,276, filed Mar. 31, 2017 and, entitled "SYSTEM AND METHOD FOR SAFETY SYRINGE"; (4) U.S. Provisional Patent Application Ser. No. 62/542,230, filed Aug. 7, 2017, and entitled "CARTRIDGE SAFETY INJECTION SYSTEM AND METHODS." This application includes subject matter similar to the subject matter described in the following co-owned U.S. patent applications: (1) U.S. Utility patent application Ser. No. 14/696,342, filed Apr. 24, 2015, entitled "SYSTEM AND METHOD FOR SAFETY SYRINGE"; (2) U.S. Utility patent application Ser. No. 14/543,787, filed Nov. 17, 2014, entitled "SYSTEM AND METHOD FOR DRUG DELIVERY WITH A SAFETY SYRINGE"; (3) U.S. Utility patent application Ser. No. 14/321,706, filed Jul. 1, 2014, entitled "SAFETY SYRINGE"; (4) U.S. Utility patent application filed on Nov. 1, 2017 and entitled "SYSTEM AND METHOD FOR SAFETY SYRINGE"; (5) U.S. Utility patent application filed on Nov. 1, 2017 and, entitled "SYSTEM AND METHOD FOR SAFETY SYRINGE"; and (6) U.S. Utility patent application filed on Nov. 1, 2017 and, entitled "CARTRIDGE SAFETY INJECTION SYSTEM AND METHODS." The contents of the aforementioned patent applications are hereby expressly and fully incorporated by reference in their entirety, as though set forth in full.

FIELD OF THE INVENTION

The present invention relates generally to injection systems, devices, and processes for facilitating various levels of control over fluid infusion, and more particularly to systems and methods related to multiple chamber safety syringes in healthcare environments.

BACKGROUND

Millions of syringes, such as that depicted in FIG. 1A (2), are consumed in healthcare environments every day. A typical syringe (2) comprises a tubular body (4), a plunger (6), and an injection needle (8). As shown in FIG. 1B, such a syringe (2) may be utilized not only to inject fluid into a patient, but also to withdraw or expel fluid out of or into a container such as a medicine bottle, vial, bag, or other drug containment system (10). Indeed, due to regulatory constraints in some countries such as the United States as well as sterility maintenance concerns, upon use of a medicine bottle (10) with a syringe (2) as shown in a particular patient's environment, such medicine bottle may only be utilized with a single patient and then must be disposed of—causing significant medical waste from bottle and remaining medicine disposal, and even contributing to periodic shortages of certain critical drugs. Referring to FIG. 2A, three Luer-type syringes (12) are depicted, each having a Luer fitting geometry (14) disposed distally, so that they may be coupled with other devices having similar mating geometry, such as the Luer manifold assembly (16) depicted in FIG. 2B. The Luer manifold assembly of FIG. 2B may be used to administer liquid drugs to the patient intravenously with or without the use of an intravenous infusion bag. The Luer fittings (14) of the syringes of FIG. 2A may be termed the "male" Luer fittings, while those of FIG. 2B (18) may be termed the "female" Luer fittings; one of the Luer interfaces may be threaded (in which case the configuration may be referred to as a "Luer lock" configuration) so that the two sides may be coupled by relative rotation, which may be combined with compressive loading. In other words, in one Luer lock embodiment, rotation, possibly along with compression, may be utilized to engage threads within the male fitting (14) which are configured to engage a flange on the female fitting (18) and bring the devices together into a fluid-sealed coupling. In another embodiment, tapered interfacing geometries may be utilized to provide for a Luer engagement using compression without threads or rotation (such a configuration may be referred to as a "slip-on" or "conical" Luer configuration). While such Luer couplings are perceived to be relatively safe for operators, there is risk of medicine spilling/leaking and parts breakage during assembly of a Luer coupling. The use of needle injection configurations, on the other hand, carries with it the risk of a sharp needle contacting or stabbing a person or structure that is not desired. For this reason, so called "safety syringes" have been developed.

One embodiment of a safety syringe (20) is shown in FIG. 3, wherein a tubular shield member (22) is spring biased to cover the needle (8) when released from a locked position relative to the syringe body (4). Another embodiment of a safety syringe (24) is shown in FIGS. 4A-4B. With such a configuration, after full insertion of the plunger (6) relative to the syringe body (4), the retractable needle (26) is configured to retract (28, 26) back to a safe position within the tubular body (4), as shown in FIG. 4B. Such a configuration which is configured to collapse upon itself may be associated with blood spatter/aerosolization problems, the safe storage of pre-loaded energy which may possible malfunction and activate before desirable, loss of accuracy in giving full-dose injections due to residual dead space within the spring compression volume, and/or loss of retraction velocity control which may be associated with pain and patient anxiety.

Further complicating the syringe marketplace is an increasing demand for pre-filled syringe assemblies such as those depicted in FIGS. 5A and 5B, which generally comprise a syringe body, or "drug enclosure containment delivery system", (34), a plunger tip, plug, or stopper (36), and a distal seal or cap (35) which may be fitted over a Luer type interface (FIG. 5A shows the cap 35 in place; FIG. 5B has the cap removed to illustrate the Luer interface 14). Liquid medicine may reside in the volume, or medicine reservoir, (40) between the distal seal and the distal end (37) of the plunger tip (36). The plunger tip (36) may comprise a standard butyl rubber material and may be coated, such as with a biocompatible lubricious coating (e.g., polytetrafluoroethylene ("PTFE")), to facilitate preferred sealing and relative motion characteristics against the associated syringe body structure and material. The proximal end of the syringe body (34) in FIG. 5B comprises a conventional integral syringe flange (38), which is formed integral to the material of the syringe body (34). The flange (38) is configured to extend radially from the syringe body (34) and may be configured to be a full circumference, or a partial circumference around the syringe body (34). A partial flange is known as a "clipped flange" while the other is known as a "full flange." The flange is used to grasp the syringe with the fingers to provide support for pushing on the plunger to give the injection. The syringe body (34) preferably comprises a translucent material such as a glass or polymer. To form a contained volume within the medicine chamber or reservoir (40), and to assist with expulsion of the associated fluid through the needle, a plunger tip (36) may be positioned within the syringe body (34). The syringe body (34) may define a substantially cylindrical shape (i.e., so that a plunger tip 36 having a circular cross sectional shape may establish a seal against the syringe body (34)), or be configured to have other cross sectional shapes, such as an ellipse.

Such assemblies are desirable because they may be standardized and produced with precision in volume by the few manufacturers in the world who can afford to meet all of the continually changing regulations of the world for filling, packaging, and medicine/drug interfacing materials selection and component use. Such simple configurations, however, generally will not meet the new world standards for single-use, safety, auto-disabling, and anti-needle-stick. Thus certain suppliers have moved to more "vertical" solutions, such as that (41) featured in FIG. 5C, which attempts to meet all of the standards, or at least a portion thereof, with one solution; as a result of trying to meet these standards for many different scenarios, such products may have significant limitations (including some of those described above in reference to FIGS. 3-4B) and relatively high inventory and utilization expenses.

Moreover, an increasing number of injectable liquids (e.g., medicines) have an additional requirement that two or more components must be combined to form an injectable combination or solution shortly before delivery into a patient. While the multiple components can be mixed in a separate open container before the injectable combination is taken up into a syringe, such mixing in an open container and drawing into a syringe can be inaccurate and lead to loss of components or the injectable combination. Further, drawing the injectable combination into a syringe can lead to unnecessary exposure of a user to an uncapped needle.

In addition, an increasing number of injectable liquids (e.g., medicines) have yet another requirement that time of exposure of the injectable liquid to metals (e.g., stainless steel of a needle) be minimized.

There is a need for injection systems which address the shortcomings of currently-available configurations. In particular, there is a need for multiple chamber safety injection solutions which may utilize the existing and relatively well-controlled supply chain of conventionally delivered pre-filled syringe assemblies such as those described in reference to FIGS. 5A and 5B.

SUMMARY

Embodiments are directed to injection systems. In particular, the embodiments are directed to multiple chamber safe injection systems that move the needle into a protected configuration to minimize accidental user injury and contamination with used needles.

In one embodiment, a system for mixing drug products and injecting includes a syringe body defining a proximal opening and a distal needle interface at a distal end thereof. The system also includes proximal and distal stopper members disposed in the syringe body, forming a proximal drug chamber between the proximal and distal stopper members and a distal drug chamber between the distal stopper member and the distal end of the syringe body. The system further includes a plunger member defining a plunger interior and configured to be manually manipulated to insert the proximal stopper member relative to the syringe body. The plunger member includes a needle retention feature disposed in the plunger interior, an energy-storage member disposed in the plunger interior, and an energy-storage member latching member disposed in the plunger interior. The system further includes a needle hub assembly coupled to the distal needle interface of the syringe body. The needle hub assembly includes a needle having a needle proximal end feature, a hub, and a needle latching member configured to couple the needle to the hub. First and second sizes of the respective proximal and distal drug chambers can be modified by movement of the proximal and distal stopper members relative to the syringe body. The needle is at least partially retractable into plunger interior upon manipulation of the plunger member relative to the syringe body to transform the energy-storage member latching member from a latched state to an unlatched state.

In another embodiment, a system for mixing drug products and injecting includes a cartridge body defining a proximal opening and a distal needle interface at a distal end thereof. The system also includes proximal and distal stopper members disposed in the cartridge body, forming a proximal drug chamber between the proximal and distal stopper members and a distal drug chamber between the distal stopper member and the distal end of the cartridge body. The system further includes a plunger member defining a plunger interior and configured to be manually manipulated to insert the proximal stopper member relative to the cartridge body. The plunger member includes a needle retention feature disposed in the plunger interior, an energy-storage member disposed in the plunger interior, and an energy-storage member latching member disposed in the plunger interior. The system further includes a needle hub assembly coupled to the distal needle interface of the cartridge body. The needle hub assembly includes a needle having a needle proximal end feature, a hub, and a needle latching member configured to couple the needle to the hub. First and second sizes of the respective proximal and distal drug chambers can be modified by movement of the proximal and distal stopper members relative to the cartridge body. The needle is at least partially retractable into plunger interior upon manipulation of the plunger member relative to the cartridge body to transform the energy-storage member latching member from a latched state to an unlatched state.

In one or more embodiments, the needle is configured to pierce entirely through at least the distal stopper member to be retracted into the plunger interior. The energy-storage member latching member may be intercoupled between an interior surface of the plunger member and the needle retention feature. The proximal and distal drug chambers may respectively contain first and second components of a drug to be mixed together prior to injecting into a patient.

In one or more embodiments, the system has a transport configuration wherein the needle proximal end feature is disposed in the distal drug chamber, a transfer configuration wherein the needle proximal end feature has at least partially pierced the distal stopper member and is at least partially disposed in the proximal drug chamber, and a mixed configuration wherein the proximal and distal stopper members are in contact with each other, thereby transferring a first drug component from the proximal drug chamber to the distal drug chamber to mix the first drug component with a second drug component in the distal drug chamber. The needle may include a distal end opening, a middle opening disposed in the distal drug chamber when the system is in the transport, transfer, and mixed configurations, and a proximal opening disposed in the proximal drug chamber when the system is in the transport and transfer configurations.

In one or more embodiments, the needle also includes a plurality of proximal openings, the proximal opening being one of the plurality of proximal openings. At least some of the proximal openings may be disposed in the proximal drug chamber when the system is in the transport and transfer configurations, and at least some of the proximal openings may be occluded by the proximal stopper member when the system is in the mixed configuration. The proximal stopper member may include a plug configured to occlude at least some of the proximal openings when the system is in the mixed configuration. A length of the plug may be greater than a distance between a proximal most opening of the plurality of proximal openings and a distal most opening of the plurality of proximal openings.

In one or more embodiments, the syringe or cartridge body includes a position indicator configured to be adjacent with a distal end of the distal stopper when the when the system is in the mixed configuration. The plunger member may include a retention clip configured to be selectively coupled to the syringe or cartridge body when the system is in the mixed configuration to prevent proximal movement of the plunger member relative to the syringe or cartridge body. The retention clip may be configured to generate an audible signal when the retention clip is selectively coupled to the syringe or cartridge body.

In one or more embodiments, the proximal and distal stoppers include respective first and second polymer coatings on respective distal and proximal surfaces thereof, such that the proximal drug chamber is defined by the syringe or cartridge body and the first and second polymer coatings. The distal stopper may have a funnel that tapers in a proximal direction, and a space disposed at a tapered proximal end of the funnel.

In one or more embodiments, the hub includes a collet and a sleeve. The collet may be configured to removably couple the needle hub assembly to the distal needle interface of the cartridge body when the sleeve is disposed around the collet. The hub may include a sealing member configured to surround and form a fluid tight seal around an external surface of the needle.

In one or more embodiments, the system also includes a transfer pipe disposed in the distal drug chamber. The needle and the transfer pipe may be removably coupled when the needle hub assembly is removably coupled to the distal needle interface of the cartridge body. The transfer pipe may have a reduced diameter section at a distal end thereof configured to secure the needle thereto.

In still another embodiment, a system for injecting includes a syringe body defining a proximal opening and a distal needle interface at a distal end thereof. The system also includes proximal and distal stopper members disposed in the syringe body, forming a drug chamber between the proximal and distal stopper members. The system further includes a plunger member defining a plunger interior and configured to be manually manipulated to insert the proximal stopper member relative to the syringe body. The plunger member includes a needle retention feature disposed in the plunger interior, an energy-storage member disposed in the plunger interior, and an energy-storage member latching member disposed in the plunger interior. The system further includes a needle hub assembly coupled to the distal needle interface of the syringe body. The needle hub assembly includes a needle having a needle proximal end feature, a hub, and a needle latching member configured to couple the needle to the hub. The needle proximal end feature is configured to penetrate the distal stopper member into the drug chamber when the system is in an injection configuration. The needle is at least partially retractable into plunger interior upon manipulation of the plunger member relative to the syringe body to transform the energy-storage member latching member from a latched state to an unlatched state.

In one or more embodiments, the drug chamber contains a drug that is sensitive to degradation during storage by contact with the metal material of the needle. The proximal and distal stoppers may include respective first and second polymer coatings on respective distal and proximal surfaces thereof, such that the drug chamber is defined by the syringe body and the first and second polymer coatings.

In one or more embodiments, the system has a transport configuration wherein the needle proximal end feature is not disposed inside the drug chamber. The needle proximal end feature may have pierced through the distal stopper and is disposed in the drug chamber, thereby providing a drug exit pathway to inject the drug into the patient when the system is in the injection configuration.

In one or more embodiments, the needle includes a distal end opening, a middle opening disposed in the drug chamber when the system is in the transport and injection configurations, and a proximal opening disposed in the drug chamber when the system is in the injection configuration.

In yet another embodiment, a method for mixing and injecting medicine into a patient includes providing a system. The system includes a syringe body defining a proximal opening and a distal needle interface at a distal end thereof. The system also includes proximal and distal stopper members disposed in the syringe body, forming a proximal medicine chamber between the proximal and distal stopper members and a distal medicine chamber between the distal stopper member and the distal end of the syringe body. The system further includes a plunger member defining a plunger interior and configured to be manually manipulated to insert the proximal stopper member relative to the syringe body. Moreover, the system includes a needle member having a distal needle tip, a medicine passage, a plurality of transfer openings, and a proximal end. The method also includes advancing the plunger member to pierce the proximal end of the needle member through the distal stopper to allow the passage of a first medicine component from the proximal medicine chamber through the medicine passage, and into the distal medicine chamber to allow mixing of the first medicine component with a second medicine component in the distal medicine chamber to form a mixed medicine.

In another embodiment, a method for mixing and injecting medicine into a patient includes providing a system. The system includes a cartridge body defining a proximal opening and a distal needle interface at a distal end thereof. The system also includes proximal and distal stopper members disposed in the cartridge body, forming a proximal medicine chamber between the proximal and distal stopper members and a distal medicine chamber between the distal stopper member and the distal end of the cartridge body. The system further includes a plunger member defining a plunger interior and configured to be manually manipulated to insert the proximal stopper member relative to the cartridge body. Moreover, the system includes a needle member having a distal needle tip, a medicine passage, a plurality of transfer openings, and a proximal end. The method also includes advancing the plunger member to pierce the proximal end of the needle member through the distal stopper to allow the passage of a first medicine component from the proximal medicine chamber through the medicine passage, and into the distal medicine chamber to allow mixing of the first medicine component with a second medicine component in the distal medicine chamber to form a mixed medicine.

In one or more embodiments, the method also includes advancing the plunger member to inject the mixed medicine into a patient. The method may include automatically retracting the distal needle tip into the syringe body when the mixed medicine has been injected into the patient.

In still another embodiment, a method for injecting medicine into a patient includes providing a system. The system includes a syringe body defining a proximal opening and a distal needle interface at a distal end thereof. The system also includes proximal and distal stopper members disposed in the syringe body, forming a medicine chamber between the proximal and distal stopper members and a distal medicine chamber between the distal stopper member and the distal end of the syringe body. The system further includes a plunger member defining a plunger interior and configured to be manually manipulated to insert the proximal stopper member relative to the syringe body. Moreover, the system includes a needle member having a distal needle tip, a medicine passage, a plurality of transfer openings, and a proximal end. The method also includes advancing the plunger member to pierce the proximal end of the needle member through the distal stopper to allow the passage of a medicine from the proximal medicine chamber through the medicine passage, and into the distal medicine chamber.

In one or more embodiments, the method also includes advancing the plunger member to inject the medicine into a patient. The method may include automatically retracting the distal needle tip into the syringe body when the mixed medicine has been injected into the patient.

In yet another embodiment, a system for mixing drug products and injecting includes a syringe body defining a proximal opening and a distal needle interface at a distal end thereof. The system also includes proximal and distal stopper members disposed in the syringe body, forming a proximal drug chamber between the proximal and distal stopper members and a distal drug chamber between the distal stopper member and the distal end of the syringe body. The system further includes a plunger member defining a plunger interior and configured to be manually manipulated to insert the proximal stopper member relative to the syringe body. The plunger member includes a needle retention feature disposed in the plunger interior, an energy-storage member disposed in the plunger interior, and an energy-storage member latching member disposed in the plunger interior. Moreover, the system includes a needle hub assembly coupled to the distal needle interface of the syringe body. The needle assembly includes a needle having a needle proximal end feature, a hub, and a needle latching member configured to couple the needle to the hub. First and second sizes of the respective proximal and distal drug chambers can be modified by movement of the proximal and distal stopper members relative to the syringe body. The needle is at least partially retractable into plunger interior upon manipulation of the plunger member relative to the syringe body to transform the energy-storage member latching member from a latched state to an unlatched state. The distal drug chamber contains a partial vacuum.

In one or more embodiments, the distal stopper member includes a proximal gate having a closed configuration where the needle proximal end feature cannot pass through the proximal gate, and an open configuration where the needle proximal end feature can pass through the proximal gate. The proximal gate may include a pair of movable arms operatively coupled to a pair of spring elements. The pair of spring elements may bias the proximal gate in the closed configuration. The needle proximal end feature may include a proximal shoulder that cannot past through the proximal gate in the closed configuration, but can pass through the proximal gate in the open configuration. The needle may include a distal shoulder that cannot past through the proximal gate in the closed configuration, but can pass through the proximal gate in the open configuration, and where the distal shoulder is distal of the proximal shoulder. The proximal gate may include a pair of movable arms operatively coupled to a pair of self-energizing hinges.

In another embodiment, a method for mixing and injecting medicine into a patient includes providing a system. The system includes a syringe body defining a proximal opening and a distal needle interface at a distal end thereof. The system also includes proximal and distal stopper members disposed in the syringe body, forming a proximal medicine chamber between the proximal and distal stopper members and a distal medicine chamber between the distal stopper member and the distal end of the syringe body. The system further includes a plunger member defining a plunger interior and configured to be manually manipulated to insert the proximal stopper member relative to the syringe body. Moreover, the system includes a needle member having a distal needle tip, a medicine passage, a plurality of transfer openings, and a proximal end. The distal medicine chamber contains a partial vacuum. The method also includes advancing the plunger member to pierce the proximal of the needle member through the distal stopper member to allow the partial vacuum in the distal drug chamber to draw a first medicine component from the proximal medicine chamber through the medicine passage, and into the distal medicine chamber to allow mixing of the first medicine component with a second medicine component in the distal medicine chamber to form a mixed medicine.

In one or more embodiments, the method also includes moving the distal stopper member distally to collapse a space in the distal medicine chamber such that an injection can be given with the system without purging the system. The method may also include advancing the plunger member to inject the medicine into a patient. The method may further include automatically retracting the distal needle tip into the syringe body when the medicine has been injected into the patient.

The aforementioned and other embodiments of the invention are described in the Detailed Description which follows.

BRIEF DESCRIPTION OF THE DRAWINGS

The foregoing and other aspects of embodiments are described in further detail with reference to the accompanying drawings, in which the same elements in different figures are referred to by common reference numerals, wherein.

Figure 1A:
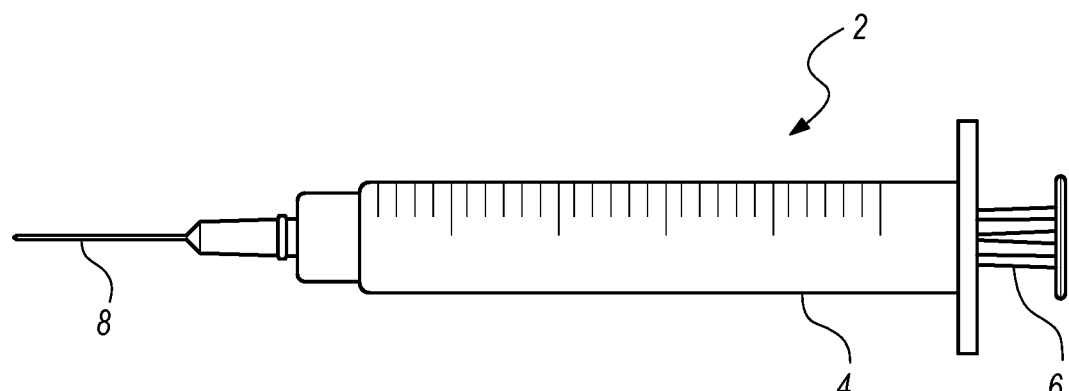
FIGS. 1A-5C illustrate various aspects of conventional injection syringe configurations.
Figure 1B:
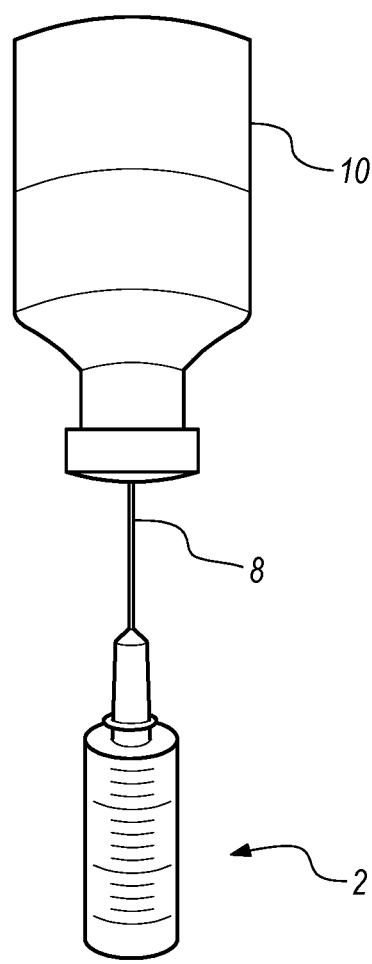
Figure 2A:
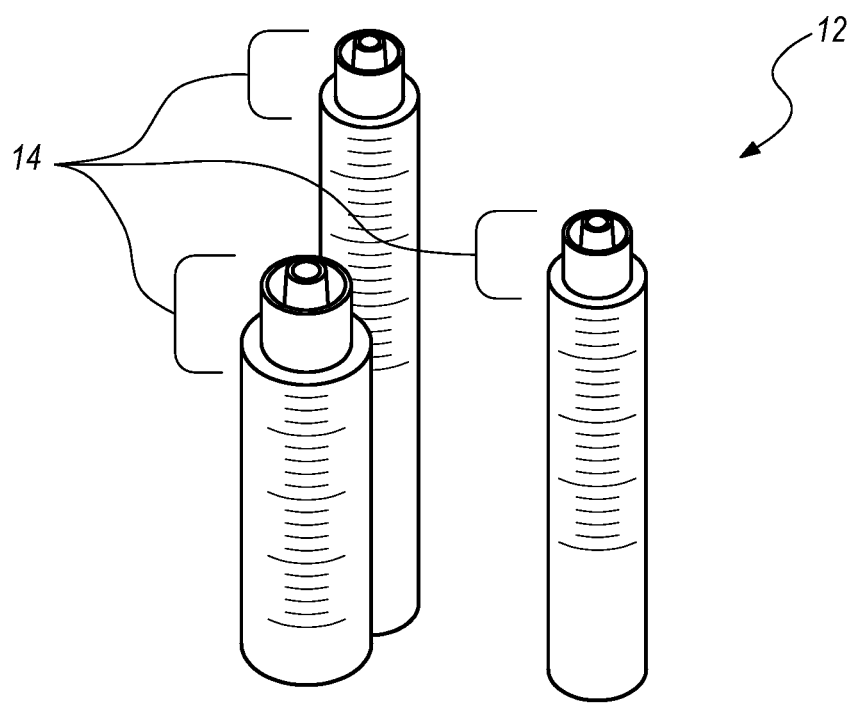
Figure 2B:
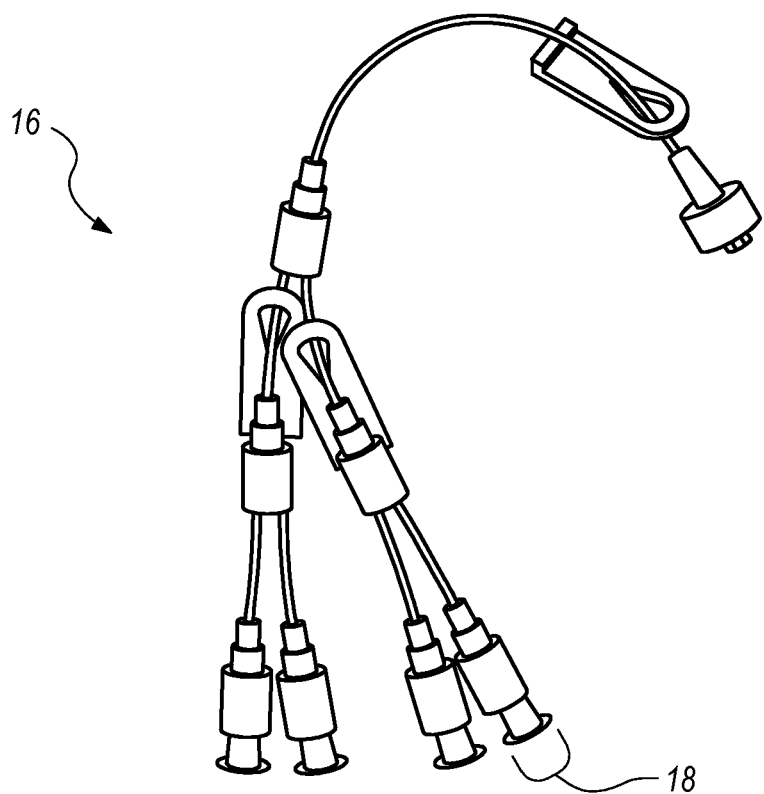
Figure 3:
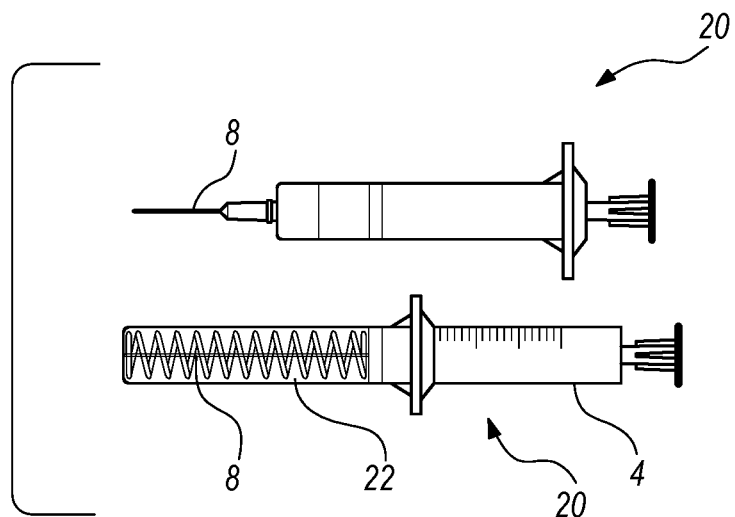
Figure 4A:
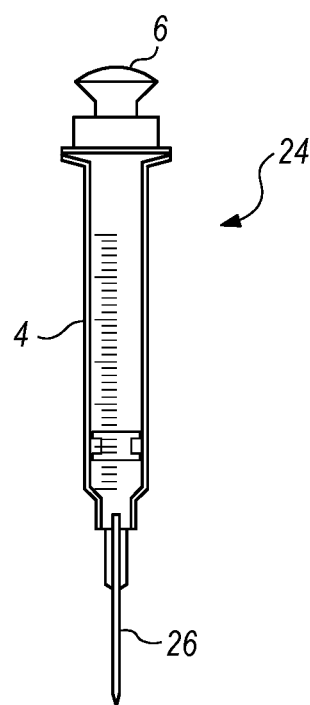
Figure 4B:
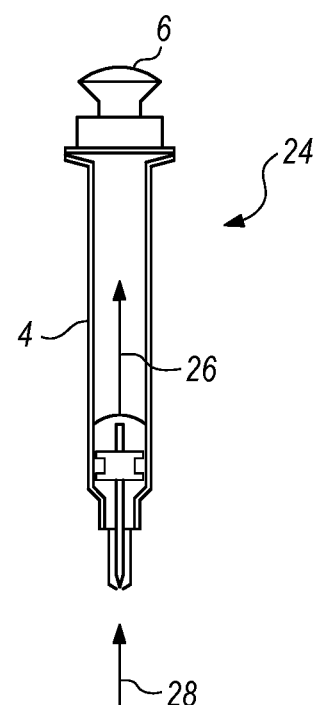
Figure 5A:
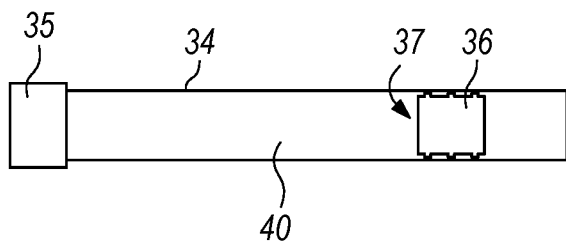
Figure 5B:
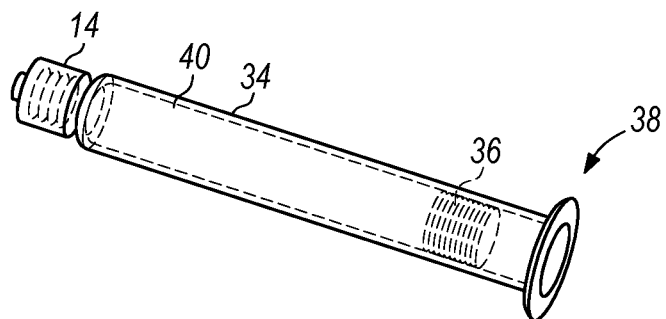
Figure 5C:
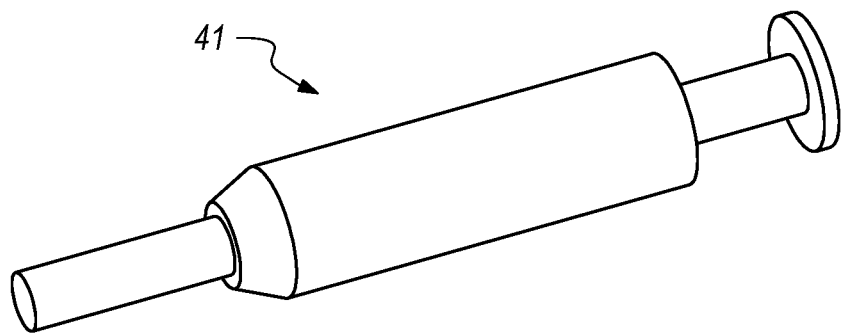

In order to better appreciate how to obtain the above-recited and other advantages and objects of various embodiments, a more detailed description of embodiments is provided with reference to the accompanying drawings. It should be noted that the drawings are not drawn to scale and that elements of similar structures or functions are represented by like reference numerals throughout. It will be understood that these drawings depict only certain illustrated embodiments and are not therefore to be considered limiting of scope of embodiments.

DETAILED DESCRIPTION OF ILLUSTRATED EMBODIMENTS

Exemplary Dual Chamber Safe Syringe Systems

Referring to FIGS. 6A-6B, a perspective and a longitudinal cross section view of a dual chamber safe injection system are shown, with a conventional off-the-shelf pre-filled syringe body (34) with conventional proximal and distal stopper members (32, 36) disposed therein. The proximal and distal stopper members (32, 36) together with the syringe body (34) define proximal and distal medicine chambers (40, 42). The proximal and distal stopper members (36, 37) occlude the proximal and distal ends of the proximal medicine chamber (40). The distal stopper member (36) occludes a proximal end of the distal medicine chamber (42). A needle coupling assembly (606) is disposed at the distal end of the distal medicine chamber (42) with a needle cover member (63) installed for storage. The dual chamber safe injection system controls transfer of a first medicine component from the proximal medicine chamber (40) to the distal medicine chamber (42) and exit of a mixed/combined medicine from the distal medicine chamber (42) distally subject to sequential insertion of a plunger assembly relative to the syringe body (34) to various degrees by a user. The plunger assembly includes the proximal stopper member (32), a plunger housing member (69) and a plunger manipulation interface (128). The first medicine component located in the proximal medicine chamber (40) may be a liquid such as aqueous or oil based medicine solutions, a gel, or the first medicine component may be a diluent for mixing with the second medicine component in the distal medicine chamber (42). The second medicine component in the distal medicine chamber (42) may be a dry form medicine such as a powder, microspheres, emulsion, lyophilized or freeze dried medicine, or a cake like solid medicine. The second medicine component in the distal medicine chamber (42) may also be a liquid that mixes with the first medicine component from the proximal medicine chamber (40).

The dual chamber safe injection system has a staked needle configuration wherein upon presentation to the user, a needle assembly, comprising a needle coupling assembly (606), a needle distal end/tip (48), a needle joining member (83—see, for example, FIG. 6E), and a needle proximal end (50) are mounted in position ready for injection after removal of a needle cover member (63) which may comprise an elastomeric sealing material on its internal surface to interface with the needle distal end (48) or the distal housing portion (610) during storage. Alternatively, the needle cover member (63) may comprise a vent (not shown) for allowing pressure resulting from the transfer and mixing of the medicine components to escape from inside the syringe body (34) while preventing contamination from entering the syringe body (34). While, the staked needle is depicted as mounted in position, the staked needle may be removably coupled to the syringe body (34) using a Luer interface (not shown), with the proximal end (50) of the needle member extending through the Luer interface and into the distal medicine chamber (42). In the embodiments depicted in FIGS. 6A-22D, a significant portion of the safe needle retraction hardware resides within a plunger housing.

Figure 6C:
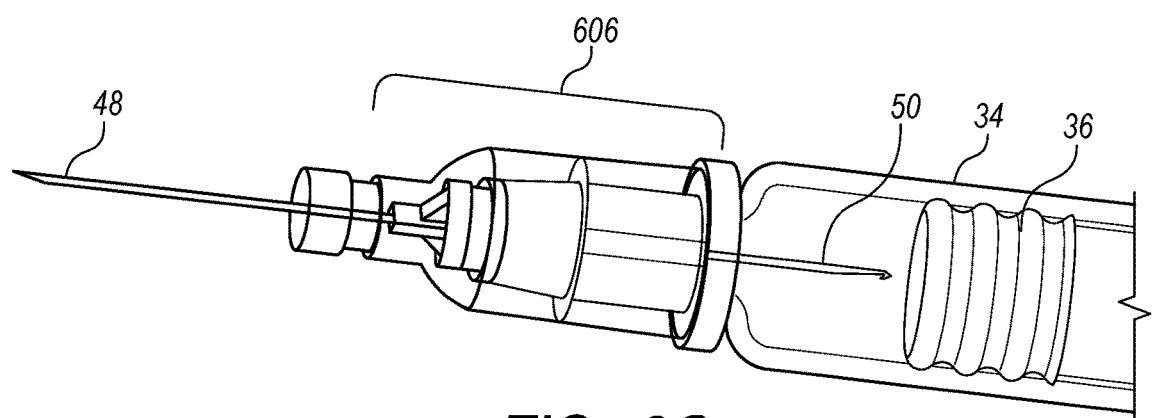
FIGS. 6A-7P illustrate various aspects of syringe based dual chamber safe injection systems wherein a distal needle end/tip may be withdrawn into a protected configuration after use according to various embodiments.
Figure 6D:
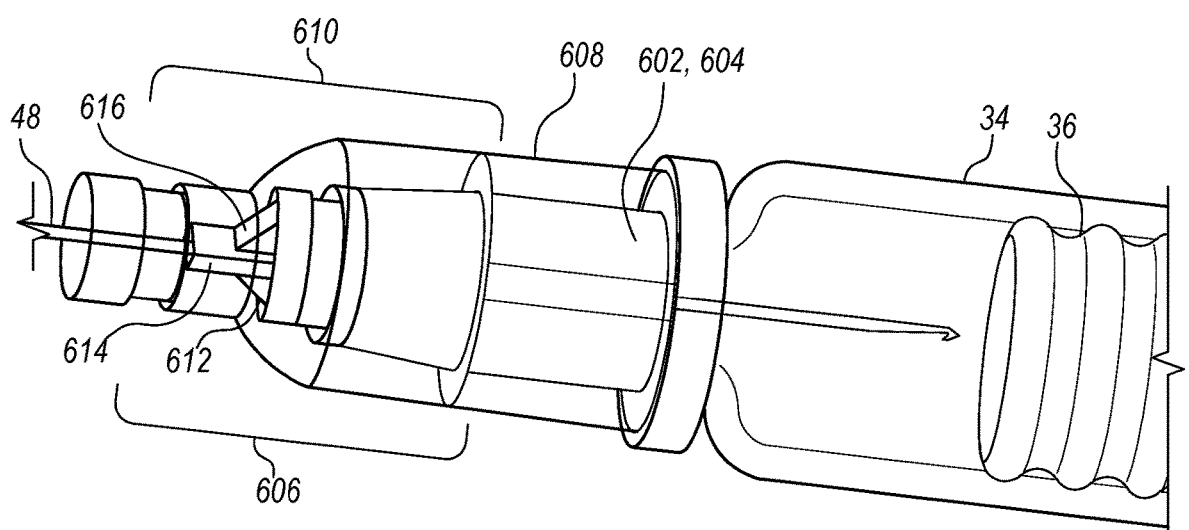

Referring to FIGS. 6C and 6D, at initial assembly time (i.e., in the factory or processing facility—not in the field in a "staked needle" configuration), the proximal housing assembly (608) is configured to snap-fit (i.e., using a snap ring element 604 comprising or coupled to the proximal housing assembly) over a slightly recessed radial portion (602) of the syringe body which is formed into the syringe body upon manufacture of the syringe body.

Referring to FIGS. 6E and 6F, the needle spine assembly (76) includes an injection member having a distal needle end (48), and a needle proximal end (50) coupled to a needle joining member (83). The needle joining member (83) is configured to have a necked-down or radially-reduced portion (111) that is configured to interface with a latching member (612) and movable block member (614) such that during injection, the needle distal end (48), needle joining member (83), and needle proximal end (50) remain fixed in position relative to the syringe body (34) during injection, but after complete insertion of the plunger assembly relative to a small diameter flange (33—see, for example, FIG. 7N) (i.e., near or after full expulsion of the medicine which may be contained within the distal medicine chamber 42 of the syringe body 34), the movable block member (614) is advanced relative to the distal housing portion (610) such that the plurality (two are illustrated) of cantilevered latch members (616) of the latch member (612) are urged out of the way by the movable block member (614). In particular, the needle spine assembly (76) is forced distally by complete advancement of the plunger assembly, advancing the movable block member (614) to move the cantilevered latch members (616). Moving the cantilevered latch members (616) allows the needle distal end (48), joining member (83), and proximal end (50) to be retracted through their coupling, thereby placing the needle distal end (48) safely within the plunger housing member (69). Alternatively, the needle distal end (48) may be retracted to a position below the outer surface of the distal housing portion (610) to safely protect the sharp point from the user. In other words, the cantilevered latch members (616) retain the position of the needle distal end (48) during injection and needle/syringe assembly, until they are pushed out of the way by the movable block member (614) at full plunger insertion, after which the needle is free to be automatically withdrawn when triggered by further distal movement of the needle spine assembly (76) as described in U.S. patent application Ser. Nos. 14/696,342 and 62/416,102, which were previously incorporated by reference herein.

In one embodiment, the plunger assembly includes a coupling member that creates a gap in the plunger assembly, which allows the plunger manipulation interface to continue to move distally after the distal stopper member has reached the distal end of the syringe body to eject substantially all of the mixed medicine from the syringe body. In this embodiment, the plunger manipulation interface is pushed distally a small distance after full injection to collapse the coupling member and the gap, release the cantilevered latch members, couple the needle spine assembly to an energy storage member, and release the energy storage member to retract the coupled needle spine assembly at least into the syringe body. This embodiment is described in further detail in U.S. patent application Ser. No. 62/416,102, which was previously incorporated by reference herein.

Figure 6G:
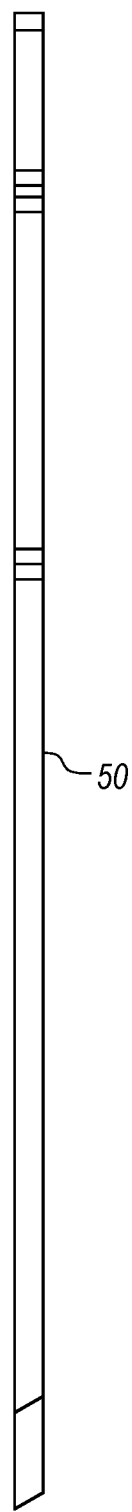
Figure 6H:
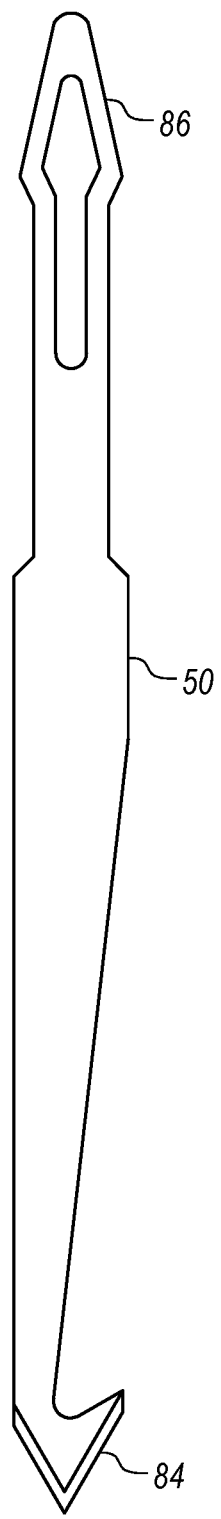
Figure 6I:
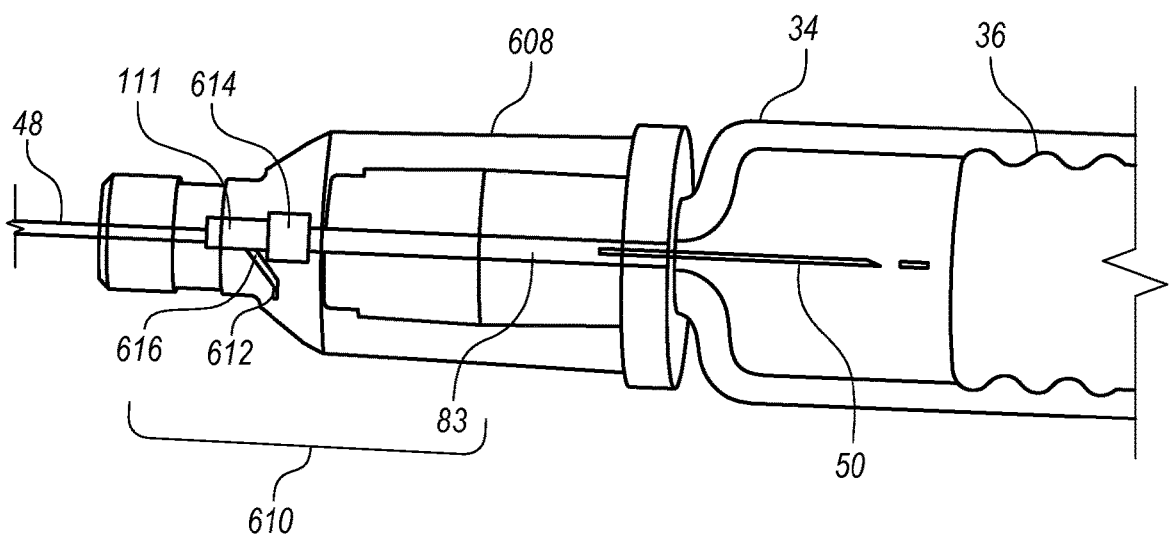
Figure 6J:
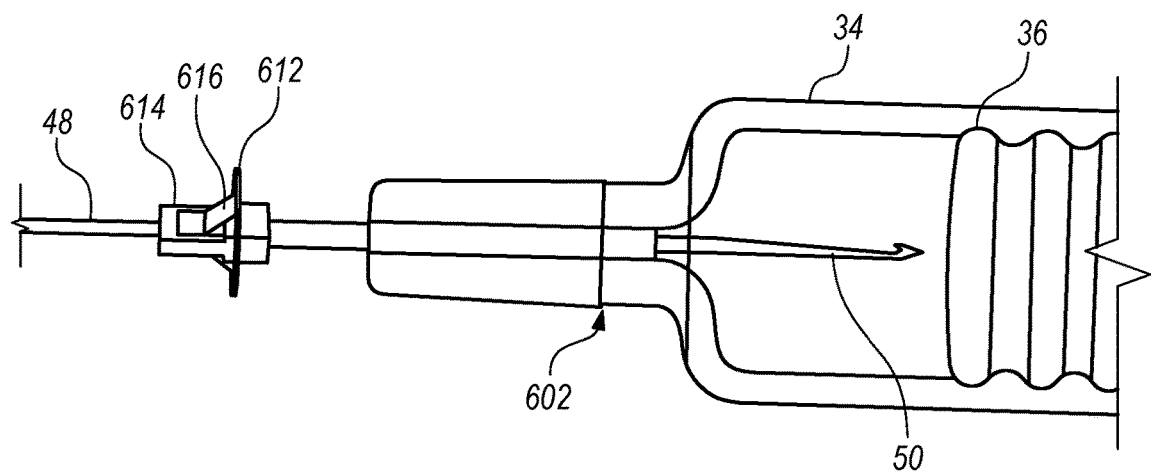
Figure 6K:
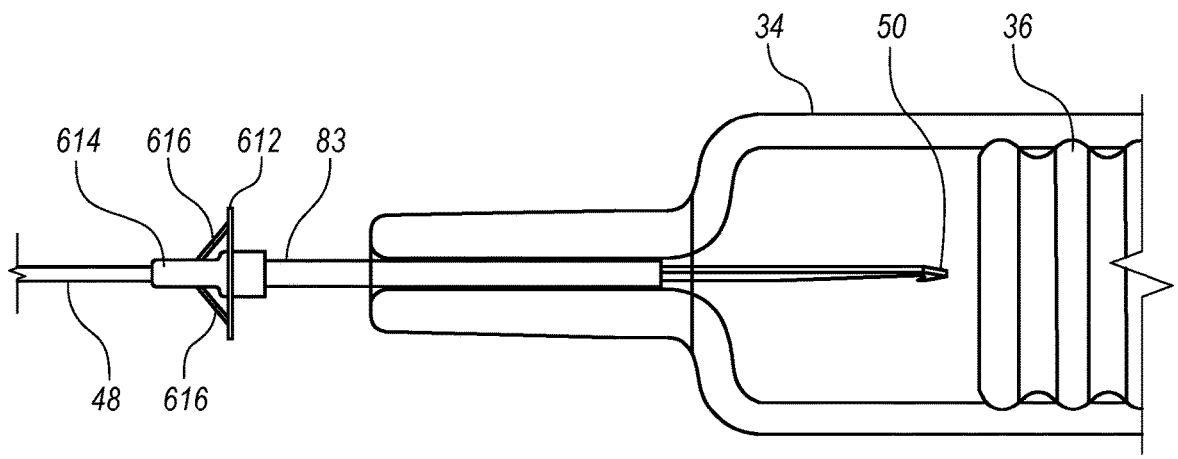
Figure 6L:
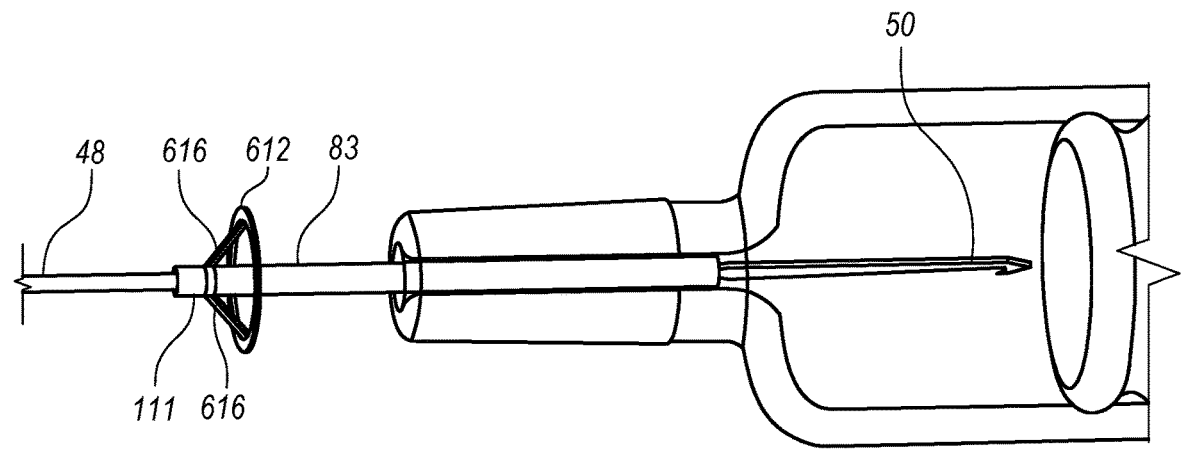

FIG. 6E illustrates aspects of a needle spine assembly (76), comprising the elements of a needle assembly without the needle coupling assembly (606). The distal portion (48) of the needle spine assembly (76) comprises a sharpened hypodermic needle tip formed on an injection member (78). As shown in FIGS. 6G and 6H, the needle proximal end (50) also comprises a sharped tip (86) that is formed into a coupling member that forms the distal portion. A generally hollow joining member (83) couples the coupling member to the tubular injection member (78). The injection member (78), sharpened tip (86) on the needle proximal end (50), and hollow joining member (83) may be held together with interference fits, welds, and/or adhesives. The most proximal end (84) of the needle proximal end (50) in the depicted embodiment comprises a "harpoon" style geometry configured to stab into and hold onto a compliant member to which it may be interfaced, as described in further detail below, for withdrawal of the needle spine assembly (76) into the plunger housing member (69). The needle proximal end (50) may be formed from a thin sheet metal component using laser cutting, etching, stamping, and/or machining techniques, for example. Other aspects of the needle spine assembly (76), such as flow paths therethrough and flow blockages, are depicted in at least FIGS. 6M-6O and described below.

Figure 6M:
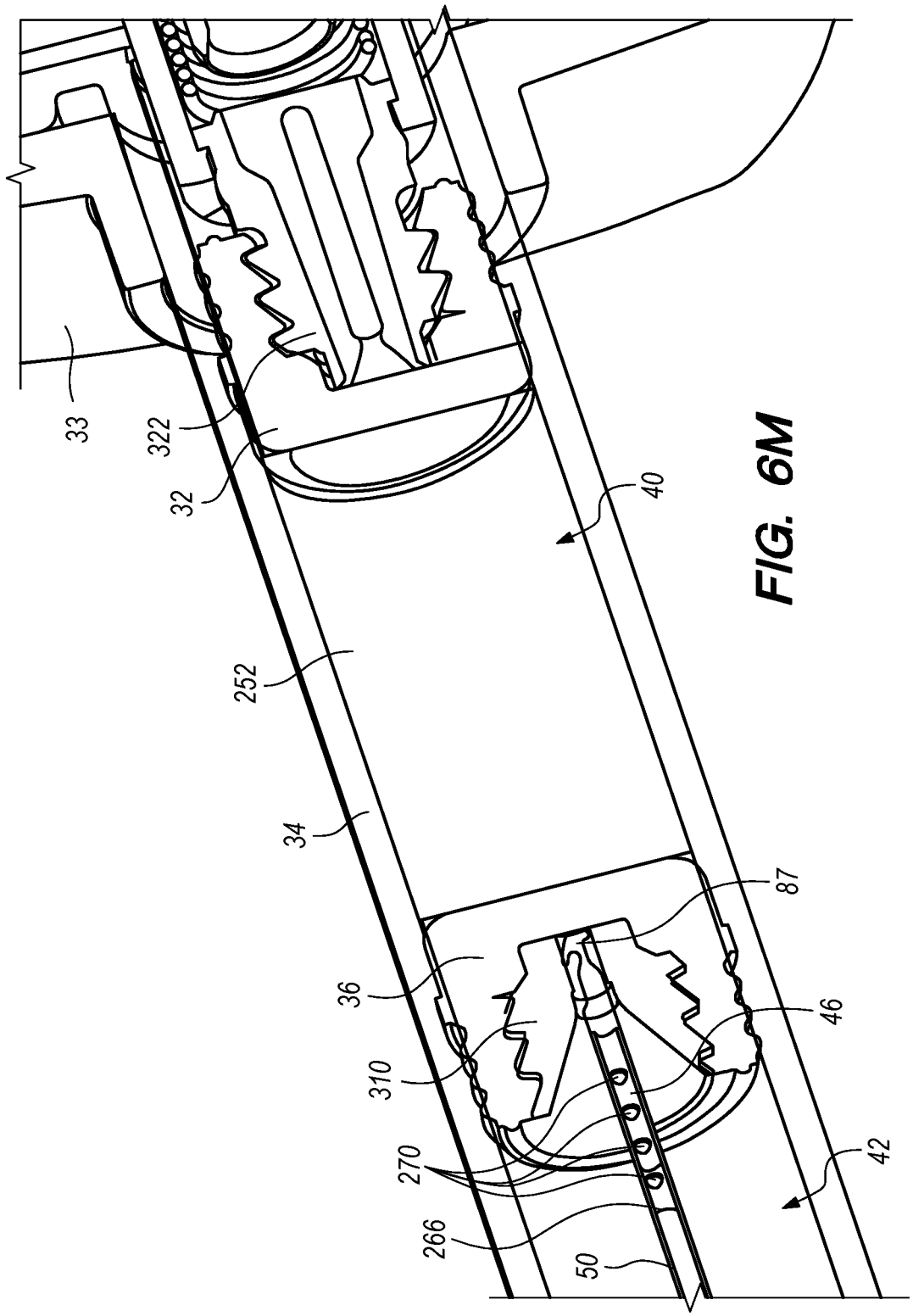
Figure 6N:
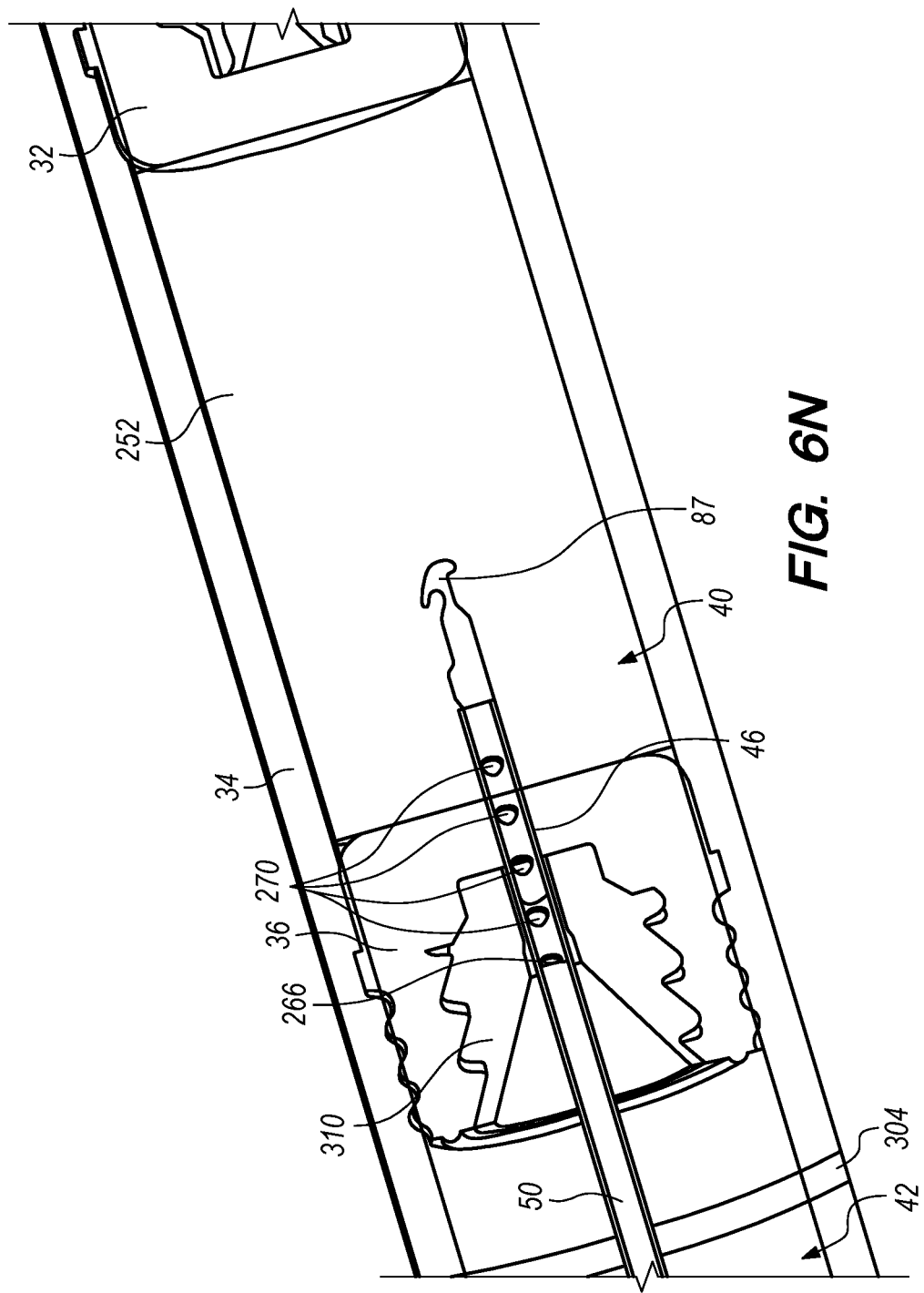
Figure 60:
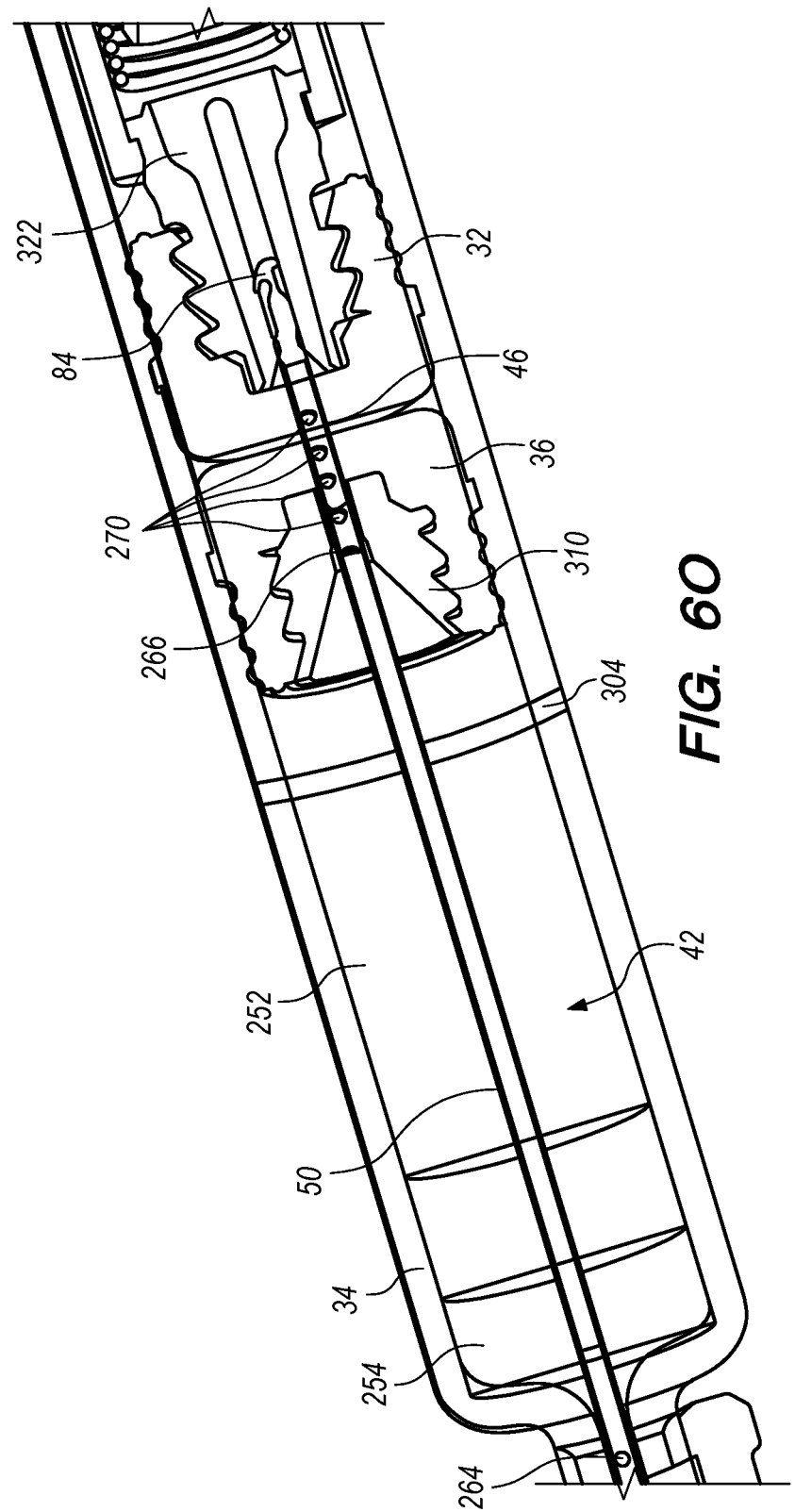
Figure 6P:
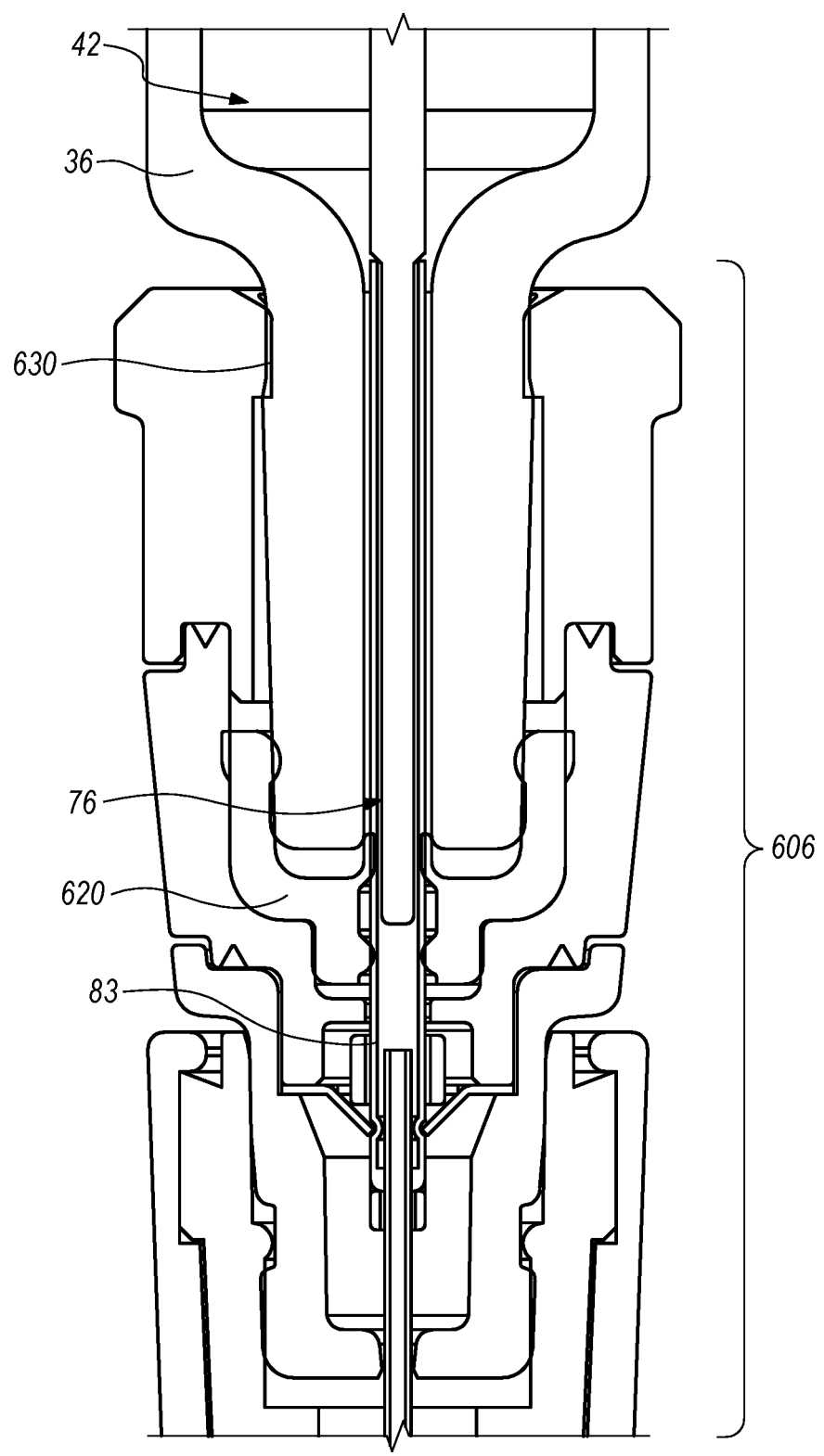

FIG. 6P illustrates a detailed cross sectional view of a needle coupling assembly (606) snapped onto a syringe body (34). FIGS. 6I-6L illustrate partial perspective wireframe views to more directly visualize the latching member (612) and cantilevered latch members (616) relative to the needle portions (48, 83, 50, 111). The function of the latching member (612) and cantilevered latch members (616) in needle retraction are described in U.S. patent application Ser. Nos. 14/696,342 and 62/416,102, which were previously incorporated by reference herein.

FIG. 6P also illustrates a distal seal (620) configured to provide a seal between the distal medicine chamber (42) in a medicine container (e.g., syringe body (34)) and the exterior surfaces of the needle spine assembly (76). Preferably, the distal seal (620) is configured to provide a seal around the outside of the needle joining member (83). This seal is further configured to provide a seal between the distal medicine chamber (42) and the interior surfaces of the needle coupling assembly (606). FIG. 6P also shows a snap fit (630) between a distal end of the medicine container (e.g., syringe body (34)) and a proximal end of the needle coupling assembly (606).

Returning to FIGS. 6A-6B, for example, a dual chamber safe injection system comprises a conventional syringe body (34), fitted with proximal and distal plunger tips (32, 36) configured to be pierced by proximal needle end (50) at an appropriate time to assist with medication transfer and needle retraction; the proximal plunger tip (32) is coupled to a plunger manipulation interface (128) by a plunger housing member (69) defining an inner volume occupied by various other portions of the assembly, as described below, which are configured to retract the needle at an appropriate time in the sequence of use. A needle coupling assembly (606) described above is included in the illustrated embodiment; other embodiments may comprise Luer type needle assembly coupling to the syringe body (34). The depicted version of the syringe body (34) comprises a small diameter flange (33) coupled to the conventional integral syringe flange (38), which has a geometry that may be manipulated or interfaced between the index and middle fingers of the operator, for example, while a thumb of the operator is interfaced with the plunger manipulation interface (128). FIGS. 6A and 6B illustrate pre-utilization assemblies with a needle cover (63) in place to mechanically isolate the distal needle end (48). The needle cover (63) may be removed and the assembly readied for injection into a patient.

As shown in FIG. 6M, the proximal and distal stopper members (32, 36), together with the syringe body (34) define a proximal medicine chamber (40) with the dual chamber safe injection system in a transport configuration. In particular, because the distal end of the proximal stopper member (32) and the proximal end of the distal stopper member (36) are each coated with a lubricious polymer coating (e.g., PTFE), the first and second polymer coatings of the proximal and distal stopper members (32, 36), together with the syringe body (34) define the proximal medicine chamber (40). The lubricious polymer coating also serves to isolate the rubber of the proximal and distal stopper members (32, 36) from the medicine and medicine components. The proximal and distal stopper members (32, 36)

may be oriented as shown in FIG. 6M or the distal stopper may be flipped so the lubricious coating faces the distal medicine chamber (42) such that the second drug component in the distal medicine chamber (42) contacts the lubricious coating for storage. In the case of the flipped stopper, the needle guide assembly may be held in place by a centering guide disc shown in FIG. 12F and described below. In an alternative embodiment, the proximal and distal stopper members (32, 36) are rubber without a lubricious polymer coating.

Because the proximal stopper member (32) is coupled to the plunger housing member (69) and the plunger manipulation interface (128), distally directed force applied to the plunger manipulation interface (128) will move the proximal stopper member (32) in a distal direction relative to the syringe body (34). Because the proximal medicine chamber (40) is prefilled with a substantially incompressible liquid and because in the transport configuration depicted in FIG. 6M there is no path for the incompressible liquid to escape the proximal medicine chamber (40), distal movement of the proximal stopper member (32) results in distal movement of the distal stopper member (36).

As shown in FIG. 6N, after the distal stopper member (36) has been moved distally relative to the syringe body (34) to place the dual chamber safe injection system into a transfer configuration, the needle proximal end (50) has pierced the distal stopper member (36) and partially entered the proximal medicine chamber (40). Indeed transfer configuration depicted in FIG. 6N, a transfer pipe (46) portion of the needle proximal end (50) forms a fluid path between the proximal and distal medicine chambers (40, 42). The transfer pipe (46) includes a plurality of proximal openings (270) and a middle opening (266). The transfer pipe (46) is hollow and forms the fluid path between the proximal most proximal opening (270), which is disposed in the proximal medicine chamber (40) and the middle opening (266), which is disposed in the distal medicine chamber (42). While the transfer pipe (46) depicted in FIGS. 6M-6O includes four proximal openings (270) and a middle opening (266), other embodiments may have more or fewer proximal and middle openings.

Increasing the number of proximal and middle openings increases the tolerance for positioning of the transfer pipe (46)/needle proximal end (50) relative to the distal stopper member (42) while maintaining an open fluid path between the proximal and distal medicine chambers (40, 42).

After the dual chamber safe injection system is in the transfer configuration as depicted in FIG. 6N, as more force is applied to the plunger manipulation interface (128), the proximal stopper member (32) can move proximally relative to the distal stopper member (36), because liquid in the proximal medicine chamber (40) can move to the distal medicine chamber (42) via the transfer pipe (46). As the liquid in the proximal medicine chamber (40) is transferred to the distal medicine chamber (42), the liquid can mix with the contents of the distal medicine chamber (42). In the embodiment depicted in FIGS. 6A and 6B, the liquid in the proximal medicine chamber (40) in the transport configuration (FIGS. 6A, 6B, and 6M) is a first, liquid component of a medicine. The content of the distal medicine chamber (42) is a second component of the medicine. Transferring the liquid from the proximal medicine chamber (40) to the distal medicine chamber (42) mixes the first and second components to form a ready to inject medicine.

As shown in FIG. 6O, continued force applied to the plunger manipulation interface (128) from the transfer configuration completes the transfer of liquids from the proximal medicine chamber (40) to the distal medicine chamber (42) and places the dual chamber safe injection system into a mixed configuration. In the mix configuration the first and second components are mixed and the medicine is ready to inject into a patient. The mixed medicine is disposed in the distal medicine chamber (42). Distal movement of the proximal stopper member (32) relative to the distal stopper member (36) has placed the proximal and distal stopper members (32, 36) into contact and reduced the volume of the proximal medicine chamber (40) to substantially zero. Accordingly, continued force applied to the plunger manipulation interface (128) moves the proximal and distal stopper members (32, 36) together and ejects the mixed medicine through a distal opening/outflow port at the distal end of the transfer pipe (46) and out of the distal medicine chamber (42) through the needle and into the patient. The transfer pipe (46) also contains a lumen plug (268) disposed between the proximal end and the distal end of the interior lumen. The lumen plug (268) blocks the mixed medicine from being forced retrograde through the flow channels during injection of the mixed medicine into the patient.

Referring to FIGS. 7A-7L, various aspects of configurations designed to facilitate injection of multi-part medications and retractions of a needle into a syringe body are illustrated, wherein two or more medication components are combined to form an injection combination or solution shortly before delivery into the patient. In one variation, a liquid first medicine component/diluent (252) may be combined with a substantially non-liquid second medicine component (254), such as a powdered form, of a drug agent, such as a freeze-dried or lyophilized drug component, shortly before injection. The configurations described herein in reference to FIGS. 7A-7L relate to dual-chamber configurations, wherein two or more chambers within the same syringe body (34) are utilized to carry, mix, and inject an injection solution.

Figure 7A:
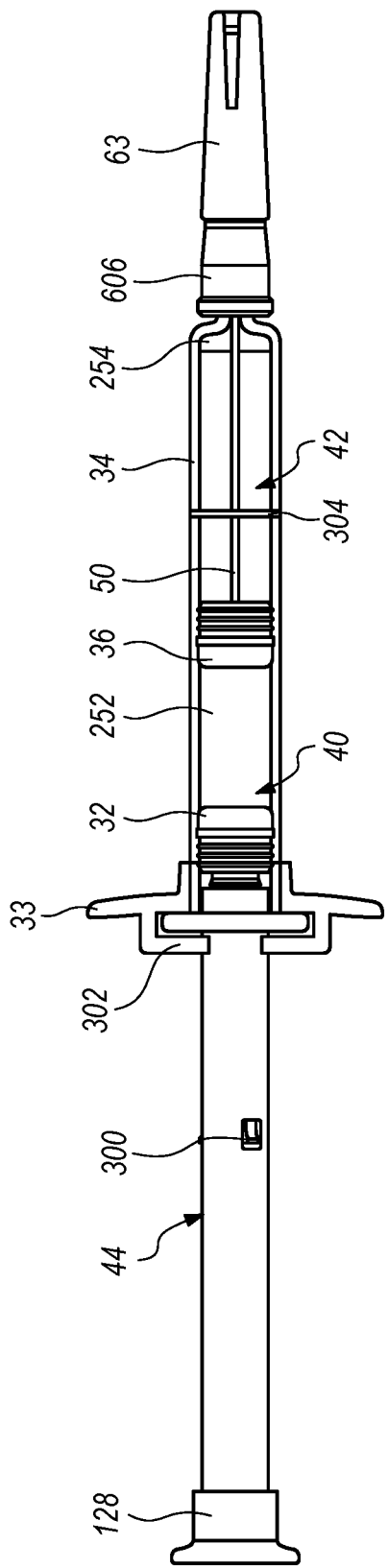
Figure 7B:
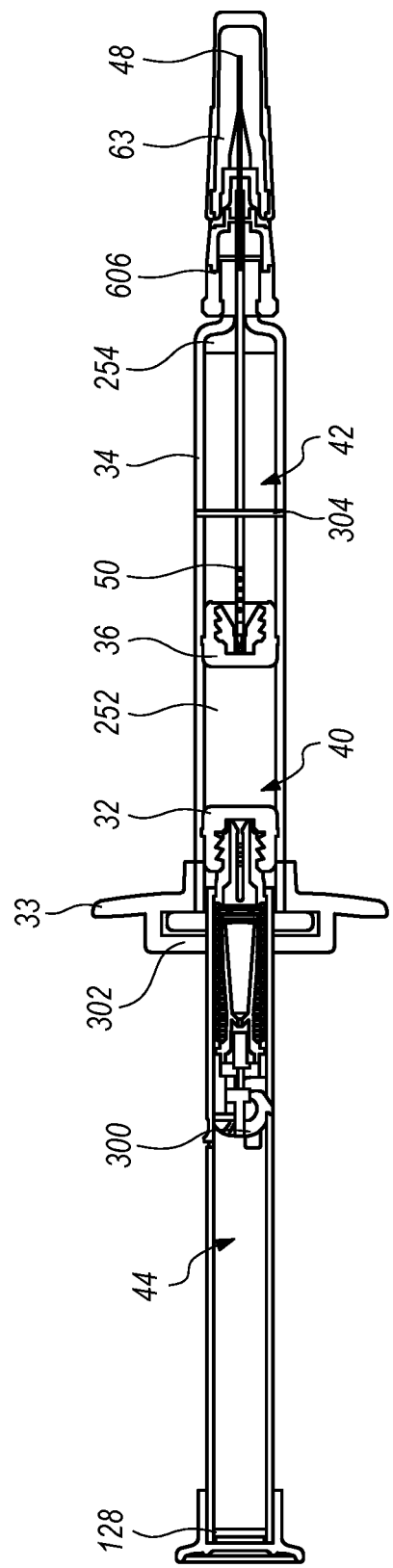

Referring to FIGS. 7A and 7B, proximal and distal medicine chambers (40, 42) are formed by a distal stopper member (36) in between two portions of the interior of a syringe body (34), such that the distal medicine chamber (42) contains an air or gas gap, as well as a non-liquid medication (254); a proximal medicine chamber (40), on the opposite side of the distal stopper member (36) contains a liquid diluent (252), which is proximally contained by a proximal stopper member (32). The liquid diluent (252) is a first component of a medicine and the non-liquid medication (254) is a second component of the medicine.

Figure 7C:
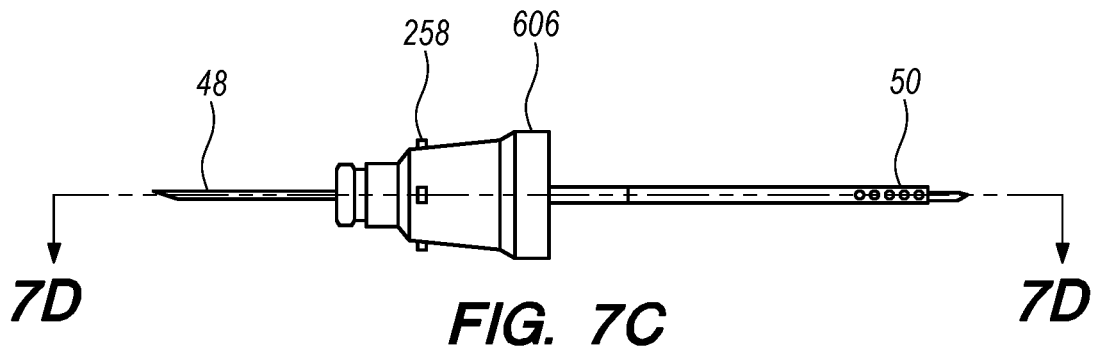
Figure 7D:
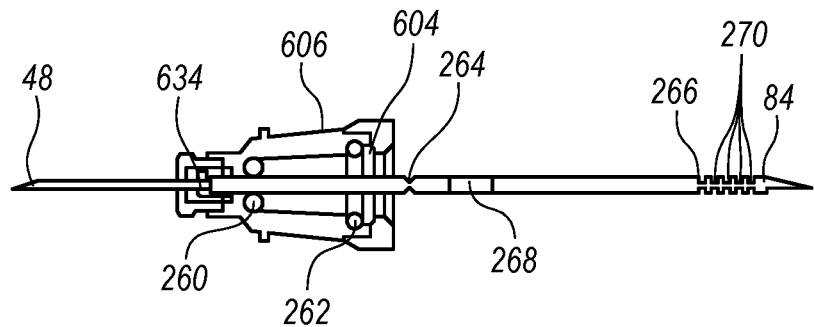

Referring to FIG. 7C, and the associated cross sectional view in FIG. 7D, various components of a needle coupling assembly (here a so-called "staked" needle coupling assembly (606) is illustrated, but other needle assemblies as described below, including Luer-coupled as well as staked configurations, may be utilized). Lug features (258) are configured to assist with coupling the needle coupling assembly (606) to a needle cover member (63), as shown in FIG. 7A, for example. A small O-ring may be utilized as a sealing member (260) around the needle shaft, while a larger O-ring may be utilized as a sealing member (262) at the syringe body (34)/needle coupling assembly (606) interface. Alternatively, the small O-ring (260) and the large O-ring (262) may be combined into a single seal that performs both of the O-ring sealing functions. Also, the small O-ring (260) may be used to seal both around the needle shaft and to the syringe body (34).

The needle includes a plurality (e.g., four) of proximal openings/ports (270) configured to allow for entry of a liquid diluent, to be expelled out of a more distally-located middle opening/aperture (266); a lumen plug (268) occludes the needle lumen to create the flow path from the proximal openings (270) to the middle opening (266) under conditions such as those described above in reference to FIGS. 6N and 7H. The needle also includes a distal opening (264) on the opposite side of the lumen plug (268) from the middle opening (266). The distal opening (264) is fluidly coupled to the needle distal end (48) through the needle to inject liquid into a patient.

Figure 7E:
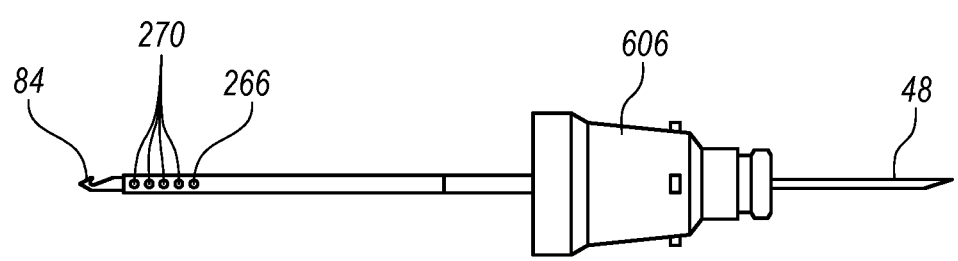
Figure 7F:
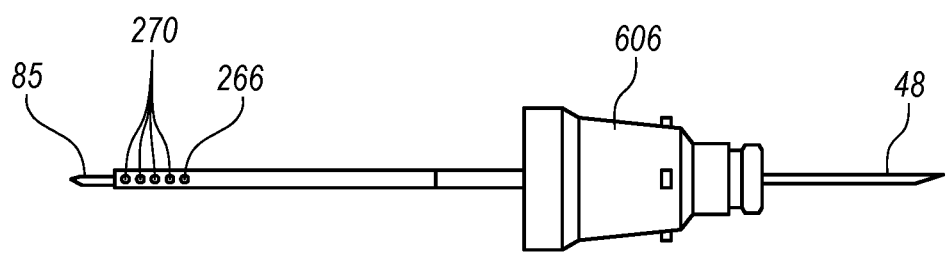

Referring to FIG. 7E, a proximal harpoon interface (84) is configured to serially penetrate proximal and distal stopper members (32, 36), and couple with a coupling feature (such as a needle retention feature are illustrated, for example, in FIGS. 7N and 7P, element 712) in the plunger rod. FIG. 7F illustrates a spike style harpoon coupling interface (85) that is configured to serially pierce both proximal and distal stopper members (32, 36) and couple with a coupling feature in the plunger rod to retract the needle member at least partially into the plunger rod after the injection has been given to the patient.

FIGS. 7A, 7B, and 7G-7P illustrate a sequence of actions for an injection procedure utilizing a dual chamber safe injection system such as that described above. Referring to FIGS. 7A and 7B, an injection assembly is in a stable configuration wherein it may be shipped or brought to an injection patient care scenario; a first drug component/liquid diluent (252) is isolated from a second non-liquid drug component (254), both within a syringe body on opposite sides of a distal stopper member (36).

FIGS. 7G and 7H illustrate initial insertion movement of the plunger assembly (44), advancing the distal (36) and proximal (32) stopper members together relative to the syringe body (34). Referring to FIG. 7H, with advancement sufficient to stab the proximal end (50) of the needle assembly across the distal stopper member (36), a fluid pathway is formed between the two previously isolated chambers (40, 42) of the syringe body (34), such that the liquid first drug component (252) in the proximal medicine chamber (40) may flow into at least one of the proximal openings (270), through the transfer pipe (46), and exit the more distal middle opening (266), to reach the non-liquid second drug component (254) in the distal medicine chamber (42).

Figure 7I:
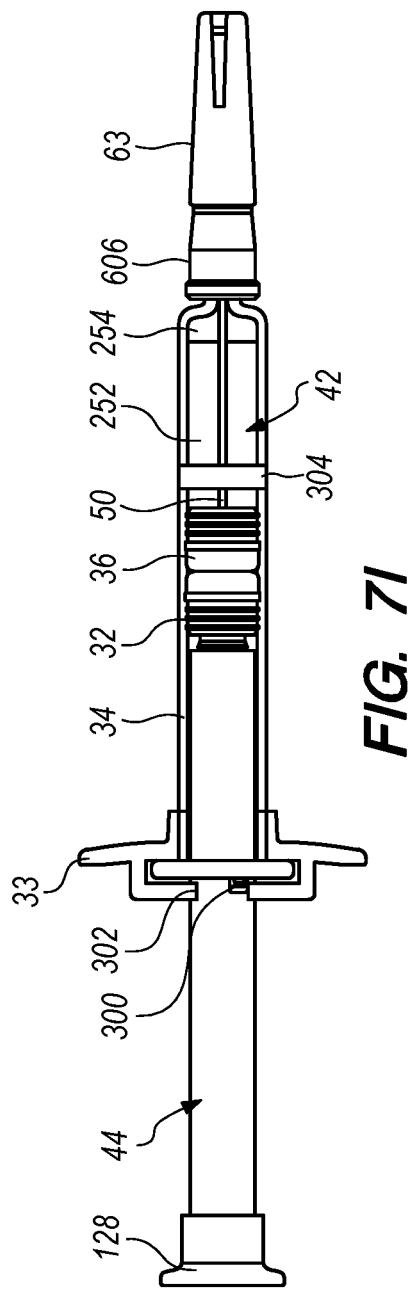
Figure 7J:
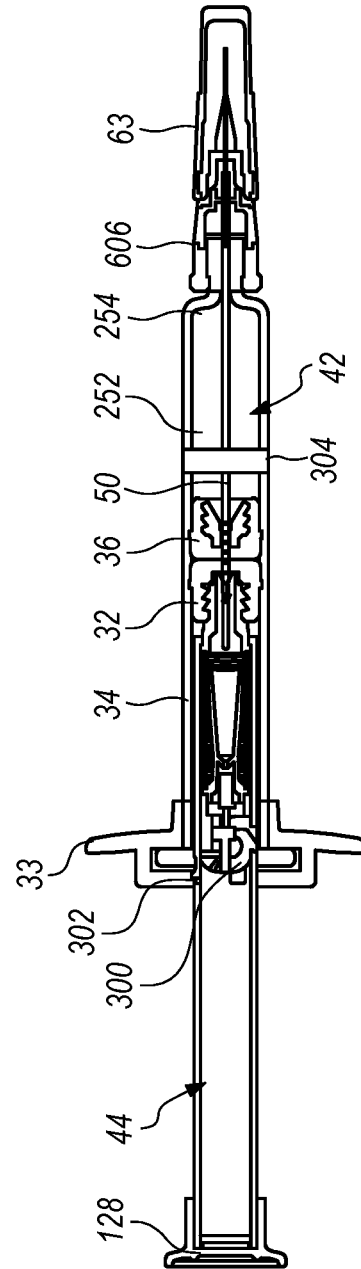

FIGS. 7I and 7J illustrate that with further insertion until the stopper members (36, 32) are immediately adjacent each other, the liquid first drug component/diluent (252) has moved into the distal medicine chamber (42) to join the non-liquid second drug component (254). FIGS. 7K and 7L illustrate that with time and/or manual agitation, the liquid first drug component/diluent (252) and previously non-liquid second drug component (254) become mixed to form a mixed medication solution (272).

In some embodiment, especially with lyophilized non-liquid second drug components, the mixed medication solution (272) may be formed with minimal or no agitation or time passage. In another embodiment, especially with drugs which are held in suspension or emulsified drugs, vigorous shaking may be necessary to facilitate mixing. In the case of vigorous shaking it is useful to the user to be able to remove their thumb from the plunger manipulation interface (128). During transfer of liquid first medicine component (252) from the proximal to the distal medicine chambers (40, 42) pressure may build up in the distal medicine chamber (42). This pressure acts upon the proximal and distal stopper members (32, 36) to resist stopper motion. The pressure buildup may also move the stopper members (32, 36) and plunger manipulation interface (128) proximally if the user does not have their thumb restraining the plunger assembly (44). Mixed configuration latches or "mix clicks" in the plunger assembly (44) (depicted in FIGS. 9A and 9B and described below) may be utilized to provide resistance to plunger manipulation interface (128) motion due to pressure buildup and allow the user to release their thumb from the plunger manipulation interface (128) for shaking or mixing of the drug. The mix clicks may also provide an audible and/or tactile indication that the transfer of liquid first medicine component (252) has been completed. The distal medicine chamber (42) may also include an agitation device, which assists in mixing of the medicine components.

With the assembly ready for injection of the mixed solution (272), the needle cover member (63) may be removed and the patient may be injected with the exposed needle distal end (48) with depression/insertion of the plunger assembly (44) and associated stopper members (36, 32) as shown in FIGS. 7M and 7N. Referring to FIGS. 7O and 7P, with full depression/insertion of the plunger assembly (44) and associated stopper members (32, 36), the sharp needle distal end/point (48) may automatically retract at least partially through the distal and proximal stopper members (36, 32) to a safe position within either the syringe body (34), the needle coupling assembly (606), or at least partially within the plunger assembly (44). Automatic retraction of the needle at least partially within the plunger is described in U.S. patent application Ser. Nos. 14/696,342 and 62/416,102, which were previously incorporated by reference herein.

Existing lyophilization manufacturing processes perform the lyophilization (freeze-drying) of the solution (e.g., a liquid drug) inside of the syringe chamber which is sealed proximal to the drug with a stopper. The distal tip of the syringe is left open during lyophilization, exposing the drug to the lyophilization process through the inside diameter ("ID") of the tip of the syringe. This existing process generally does not allow for the use of traditional glued-in staked needles, as the needle would have to be in place prior to lyophilization due to the glue curing process. The ID of the traditional 25 gauge to 34 gauge staked needles are around 0.010" to 0.003". This range of ID is generally too small to allow lyophilization of the drug in a reasonable amount of time. The staked needle assembly shown in FIGS. 6A-7P uses a Luer taper tip syringe with a tip ID of about 0.040" that allows for lyophilization. The staked needle of FIGS. 6A-7P is attached to the syringe via a snap-fit after lyophilization has taken place, sealing the drug container, and allowing for the use of existing lyophilization manufacturing processes.

While the embodiments depicted in FIGS. 6A-7P transfer liquid through a transfer pipe (46), in other dual chamber embodiments, liquid may be transferred through a bypass channel/passageway formed into a syringe body. The bypass channel may be formed in or adjacent to the wall of a glass syringe using a mandrel during syringe formation. The bypass channel may have openings into the syringe body that may be selectively occluded by the proximal and distal stopper members to control liquid transfer. Such embodiments are described in further detail in U.S. patent application Ser. No. 14/696,342, which was previously incorporated by reference herein.

A. Exemplary Harpoon Coupling Interfaces

Figure 8A:
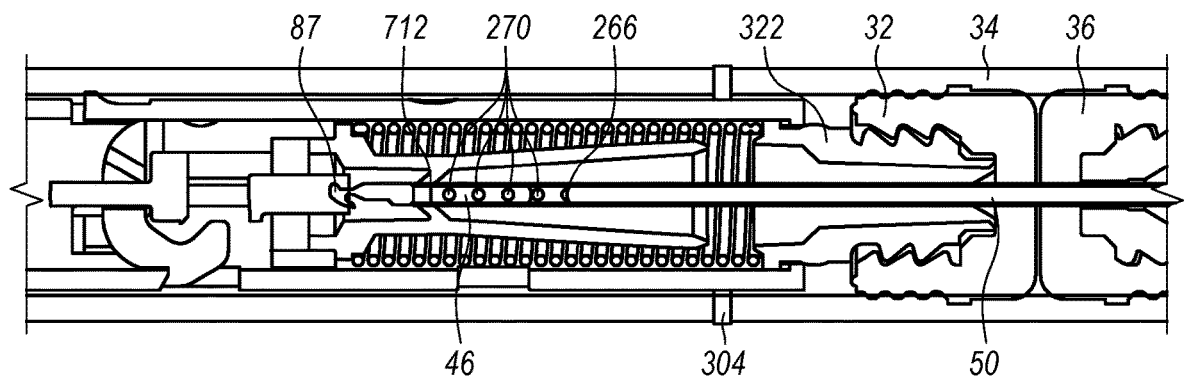
FIGS. 8A and 8B illustrate harpoon coupling interfaces according to two embodiments that can be used with dual chamber safe injection systems according to various embodiments.
Figure 8B:
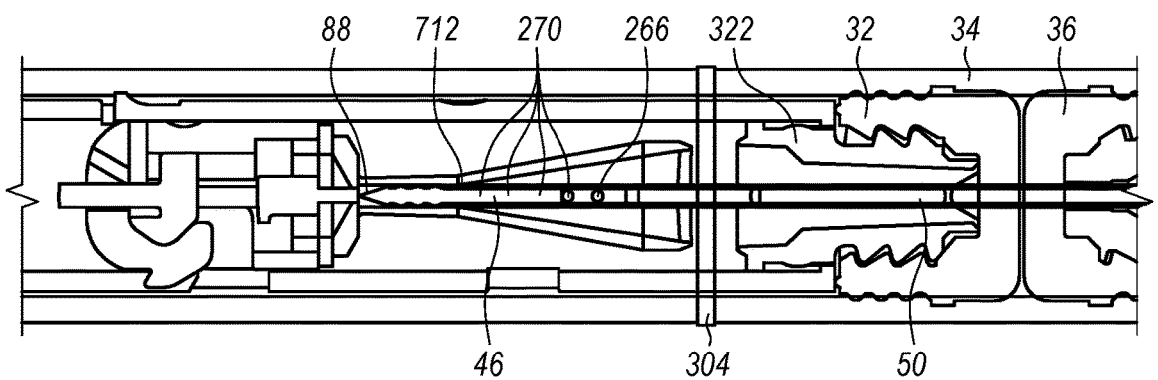

FIGS. 8A and 8B depict two embodiments of dual chamber safe syringe systems having different harpoon coupling interface (87, 88). The embodiment depicted in FIG. 8A has an articulated needle harpoon coupling interface (87). The embodiment depicted in FIG. 8B has a tree-shaped harpoon coupling interface (88). The spring has been omitted from FIG. 8B for clarity. These coupling interfaces (87, 88), their corresponding needle retention features (712), and their use to selectively retract a needle are described in in U.S. patent application Ser. No. 62/416,102, which was previously incorporated by reference herein. The different harpoon coupling interfaces (87, 88) can be used with the depicted in FIGS. 6A-7P.

B. Mixed Configuration Latch

Figure 9A:
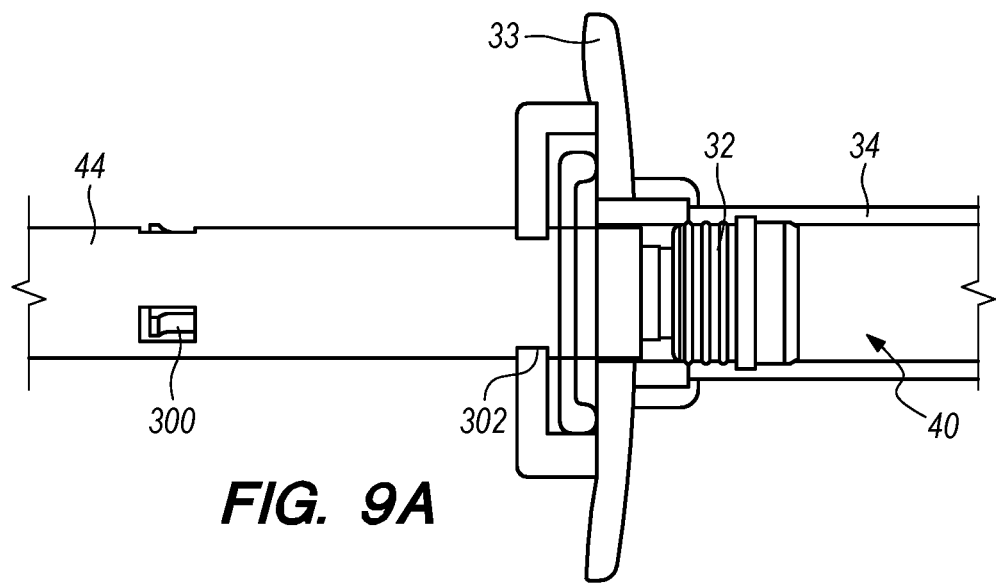
FIGS. 9A and 9B illustrate various aspects of a mixed configuration latch according to one embodiment that can be used with dual chamber safe injection systems according to various embodiments.
Figure 9B:
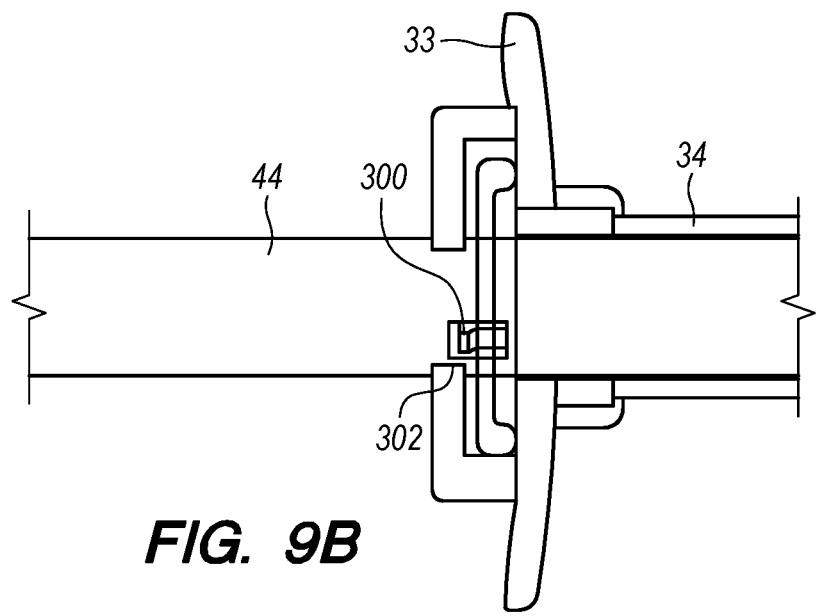

FIGS. 9A and 9B depict a mixed configuration latch (300) on a plunger assembly (44) usable with the embodiments depicted in FIGS. 6A-8B. The mixed configuration latch (300) tapers distally and is biased (e.g., by a spring) to extend radially from the plunger assembly (44). The mixed configuration latch (300) is configured such that, when the dual chamber safe syringe system is in the mixed configuration (i.e., wherein the proximal and distal stopper members are in contact with each other) the mixed configuration latch (300) moves distally beyond a detent (302) on the small diameter flange (33) coupled to the syringe body (34), as shown in FIG. 9B. At that point, the mixed configuration latch (300) extend radially from the plunger assembly (44), preventing proximal movement of the plunger assembly (44) relative to the syringe body (34).

Preventing proximal movement of the plunger assembly (44) allows a user to release pressure on the plunger manipulation interface (128) without allowing the plunger assembly (44) to be driven proximally by the pressure built up in the distal medicine chamber (42) as the liquid first medicine component is forced from the proximal medicine chamber (40) into the distal medicine chamber (42).

Radial extension of the mixed configuration latch (300) after radial compression by the tapered portion passing the detent (302) generates an audible or tactile signal (i.e., click). The audible or tactile signal indicates to a user that the dual chamber safe syringe system is in the mixed configuration, and that the user may release pressure on the plunger manipulation interface (128). The user may also agitate and/or invert the dual chamber safe syringe system to mix the medicine components (252, 254) after hearing or feeling the audible or tactile signal.

C. Mixed Configuration Indicator

Figure 10A:
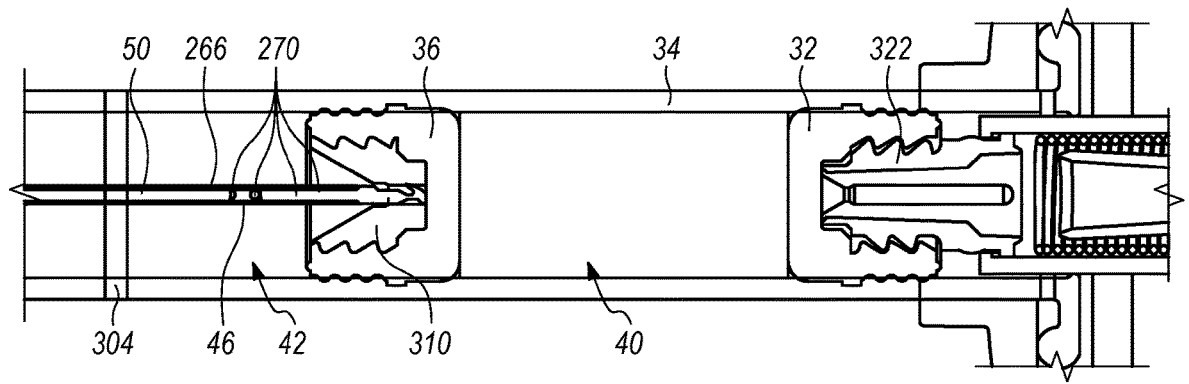
FIGS. 10A and 10B illustrate various aspects of a mixed configuration indicator according to one embodiment that can be used with dual chamber safe injection systems according to various embodiments.
Figure 10B:
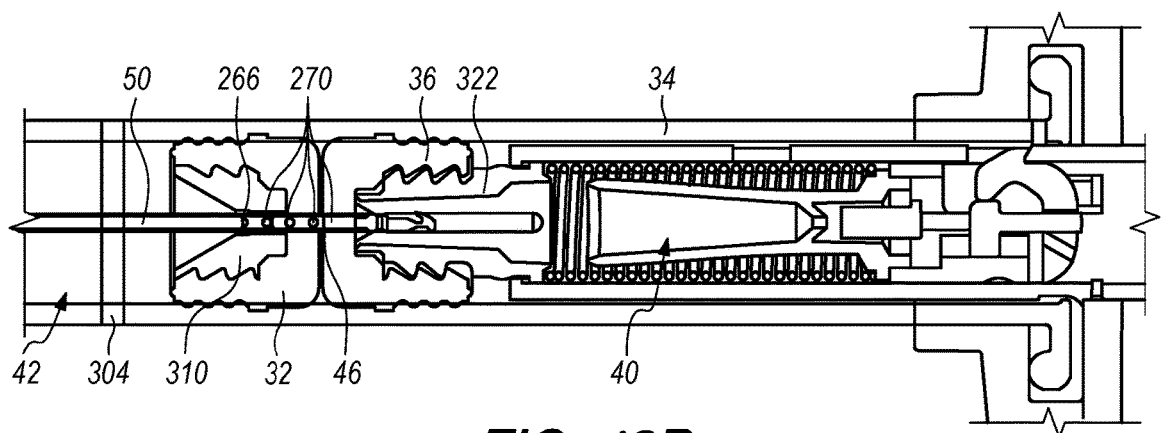

FIGS. 10A and 10B depict a portion of the dual chamber safe injection systems depicted in FIGS. 6A-9B including proximal and distal stopper members (32, 36) with a system in transport configuration (FIG. 10A) and mixed configuration (FIG. 10B). Comparing FIGS. 10A and 10B shows that the proximal medicine chamber (40) in a system in the transport configuration is collapsed when the system is moved to the mixed configuration. As described above, the liquid first medicine component (252) in the proximal medicine chamber (40) in a system in the transport configuration is transferred to the distal medicine chamber (42) through at least one proximal opening (270), the transfer pipe (46) and the middle opening (266).

For optimal performance, the pressure applied to the plunger manipulation interface (128) by a user to move the proximal stopper member (32) distally relative to the distal stopper member (36) should not exceed the pressure required to transfer liquid through the transfer pipe (46) at a maximal rate ("max transfer pressure"). The max transfer pressure is determined by various system parameters, including but not limited to, transfer tube cross-sectional area and length and liquid viscosity. If the applied pressure exceeds the max transfer pressure, the remaining incompressible liquid in the proximal medicine chamber (40) will transfer the applied pressure to the distal stopper member (36), moving the distal stopper member (36) distally relative to the syringe body (34) and the needle spine assembly (76) coupled thereto.

Moving the distal stopper member (36) relative to the needle spine assembly (76) before reaching the mixed configuration can prematurely halt liquid transfer by moving distal stopper member (36) over the middle opening (266) before all of the liquid in the proximal medicine chamber (40) is transferred to the distal medicine chamber (42). Because the lumen plug (268) prevents liquid from traveling from the proximal and middle openings (270, 266) to the distal opening (264), closing the middle opening (266) with the distal stopper member (36) effectively stops liquid transfer before completion. With even more applied pressure, the distal stopper member (36) may move even more distally, placing the middle opening (266) in the proximal medicine chamber (40) before liquid transfer is complete. This also stops liquid transfer before completion. Accordingly, applying more pressure than the max transfer pressure will result in incomplete liquid transfer, which will affect the dissolving of the substantially non-liquid second medicine component (254), and/or the concentration of the mixed medication solution (272).

In order to address the problem of the user applying more pressure than the max transfer pressure, the embodiment depicted in FIGS. 10A and 10B includes a mixed configuration indicator (304), which is a visual indicator disposed on the syringe body (34). The mixed configuration indicator (304) in FIGS. 10A and 10B is a ring disposed (e.g., painted, etched, etc.) on the syringe body (34) that indicate the approximate optimal location of the distal edge of the distal stopper member (36) when the system is in the mixed configuration. This visual indicator/cue allows a user to visually detect when the distal stopper member (36) is moving too far distally relative to the syringe body (34) before the system reaches its mixed configuration. When the user detects such movement, the user can reduce the pressure applied to the plunger manipulation interface (128) to stop/slow the distal movement of the distal stopper member (36). In some embodiments, an audible or tactile signal from the mixed configuration latch (300) indicates to the user when the system has reached the mixed configuration and it is safe to push the distal stopper member (36) distally past the mixed configuration indicator (304).

Dual chamber safe injection systems with mixed configuration indicators (304) may include directions for use that instruct a user to "not allow the front/distal stopper to pass the mixed line until you hear a click." The mixed configuration indicator (304) allows the user to vary applied pressure to allow the system to transfer liquid with minimal movement of the distal stopper member (36). The mixed configuration indicator (304) can eliminate the need for various friction increasing features previously used to control stopper movement during the liquid transfer phase of the mixing process.

D. Distal Stopper Bushing and Proximal Stopper Screw

Figure 11A:
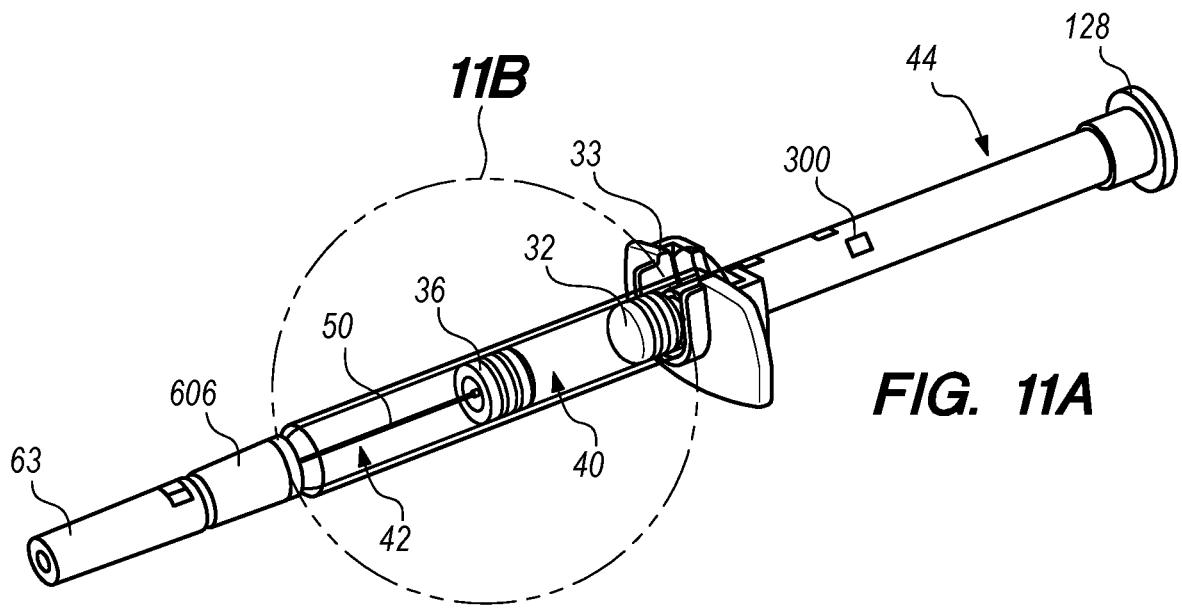
FIGS. 11A-11E illustrate various aspects of the dual chamber safe injection systems depicted in FIGS. 6A-10B in increasing detail to demonstrate various aspects of the systems.
Figure 11B:
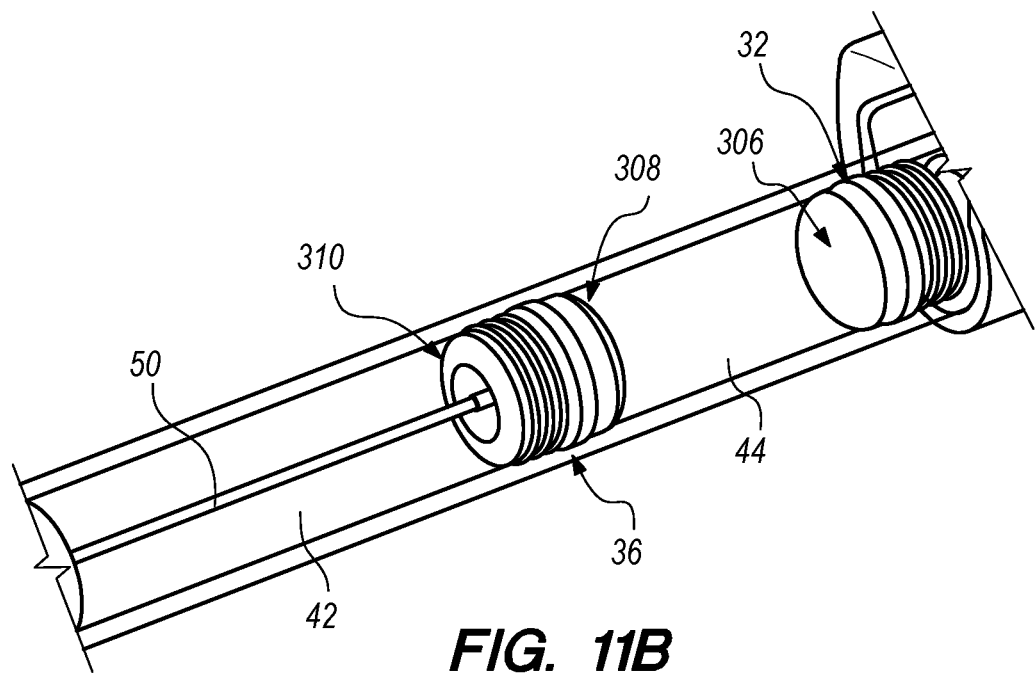
Figure 11C:
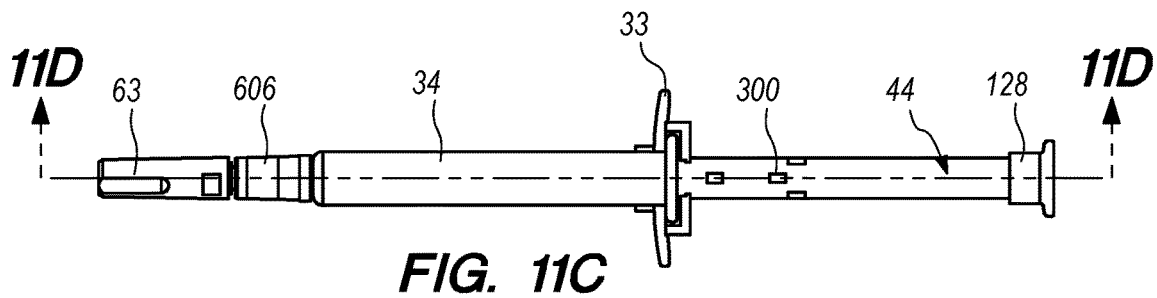
Figure 11D:
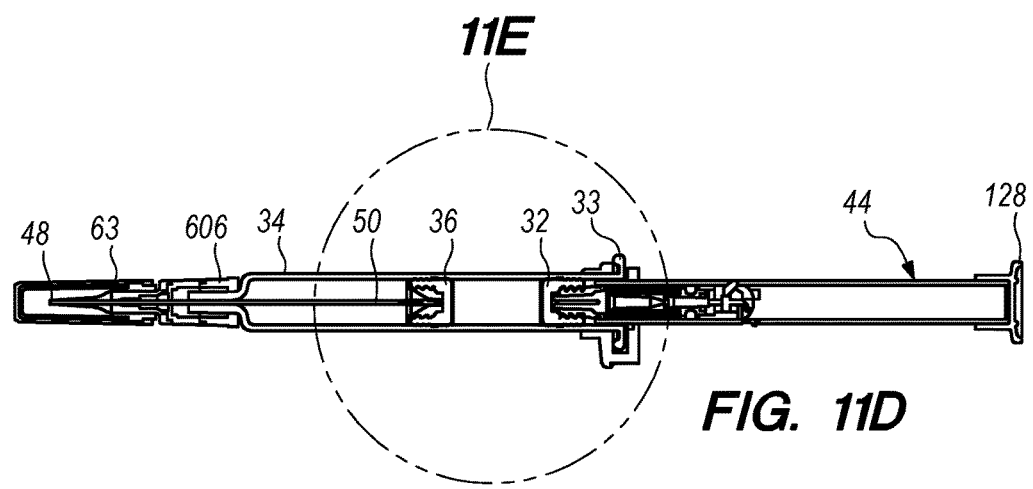
Figure 11E:
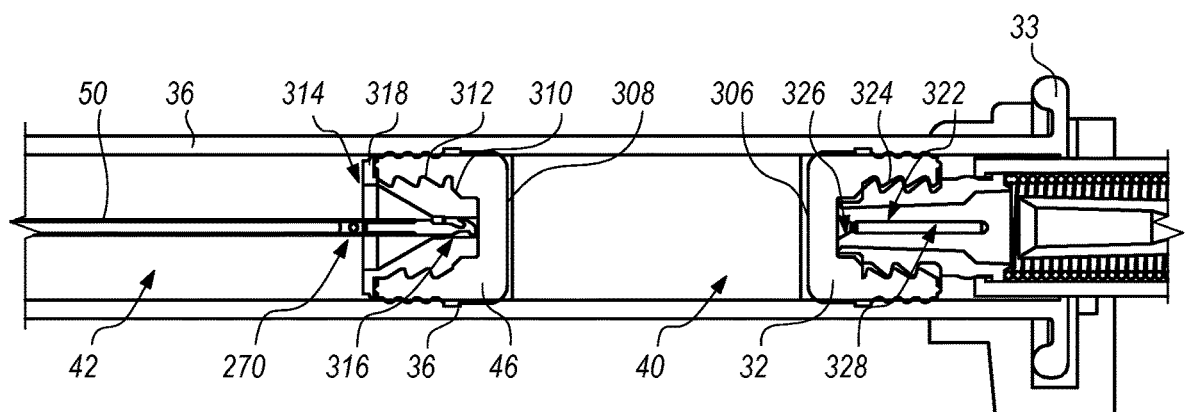

FIGS. 11A-11E illustrate the dual chamber safe injection systems depicted in FIGS. 6A-10B in increasing detail to demonstrate various features of the systems. As best shown in FIG. 11E, while the proximal and distal stopper members (32, 36) start as conventional, off-the-shelf stoppers for injection systems, each of the proximal and distal stopper members (32, 36) are modified with additional components to optimize the performance of the dual chamber safe injection system.

FIG. 11E shows that the distal stopper member (36) is disposed in the syringe body (34) in an orientation that is the opposite of the typical orientation for a stopper. In this reverse orientation, the lubricious coating (308) on the distal stopper member (36) is facing the proximal medicine chamber (40), and the female threads on an inner surface of the distal stopper member (36) are facing the distal medicine chamber (42). On the other hand, the proximal stopper member (32) is disposed in the syringe body (34) in the typical orientation, such that its lubricious coating (306) is facing the proximal medicine chamber (40), and its female threads are facing the plunger assembly (44). The respective female threads of the proximal and distal stopper members (32, 36) are configured for attachment. Typically the female threads are used to attach a plunger assembly. However, the dual chamber safe injection systems described herein take advantage of the female threads to attach additional components to optimize performance. The lubricious coatings (306, 308) may be PTFE, which acts as a fluid barrier to protect the (e.g., butyl-rubber) proximal and distal stopper members (32, 36) from the first medicine component in the proximal medicine chamber and (40) or vice versa.

Figure 12A:
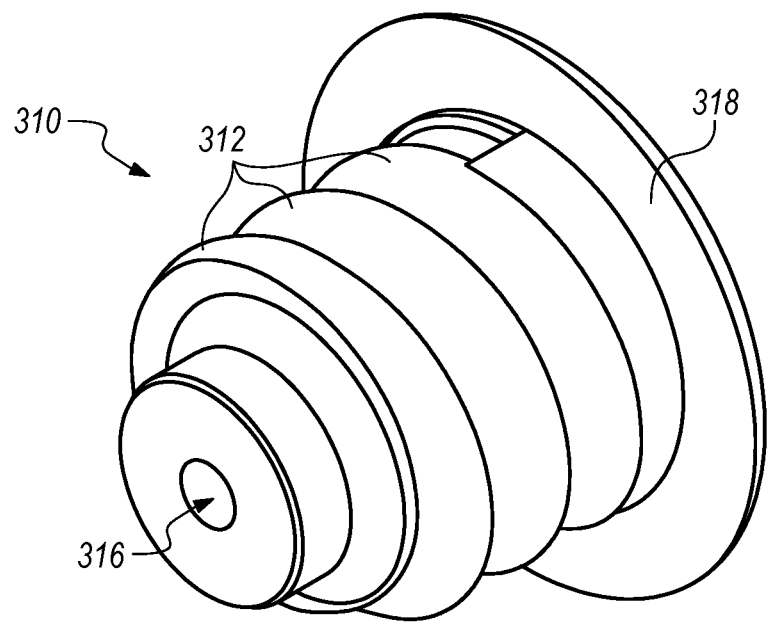
FIGS. 12A-12D illustrate various aspects of a distal stopper bushing according to one embodiment that can be used with dual chamber safe injection systems according to various embodiments.
Figure 12B:
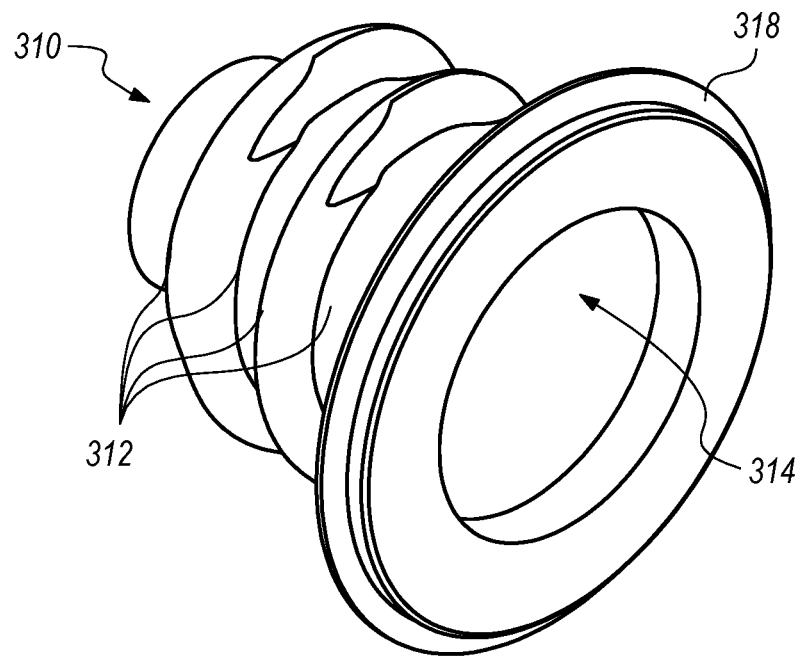
Figure 12C:
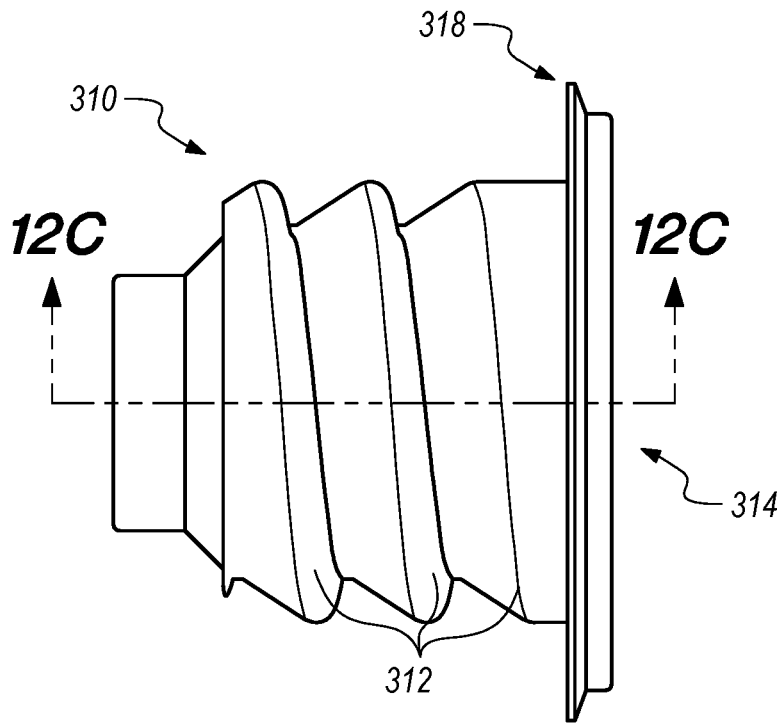
Figure 12D:
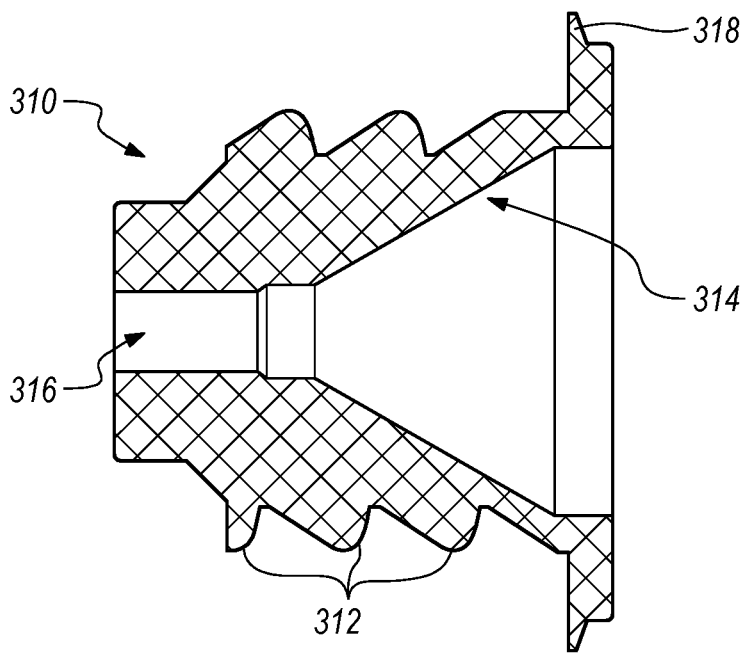

A distal stopper bushing (310) is secured to the distal stopper member (36) using an interaction between male threads (312) on the distal stopper bushing (310) and the distally facing female threads on the distal stopper member (36). The distal stopper bushing (310) is shown in isolation in FIGS. 12A-12D. As shown in FIGS. 11E and 12D, the distal stopper bushing (310) defines an alignment funnel (314) that is distally facing when the distal stopper bushing (310) installed in the distal stopper member (36) that is in turn installed in the dual chamber safe injection system. The distally facing alignment funnel (314) is configured to guide a needle proximal end (50) into position when assembling the dual chamber safe injection system. As also shown in FIGS. 11E and 12D, the distal stopper bushing (310) also defines a receiving space (316) configure to receive the needle proximal end (50) when the dual chamber safe injection system is assembled in the transport configuration. The receiving space (316) is located adjacent to a "pierce through" section of the rubber distal stopper bushing (310) which is configured to be pierced by the needle proximal end (50) to expose at least one proximal opening (270) into the proximal medicine chamber (40) to allow liquid transfer. During assembly, the distally facing alignment funnel (314) guides the needle proximal end (50) into the receiving space (316), which secures the needle proximal end (50) during transportation and storage of the dual chamber safe injection system. The alignment funnel (314) also guides the needle proximal end (50) during liquid transfer and/or needle retraction to ensure that the needle proximal end (50) enters a plunger rod funnel for needle retraction (as described in U.S. patent application Ser. No. 62/416,102, which was previously incorporated by reference herein). The distal stopper bushing (310) also defines a bushing flange (318), which seals against a distally facing surface of the distal stopper member (36) to limit contact between the second medicine component in the distal medicine chamber (42) and the distal stopper member (36) during transportation and storage of the dual chamber safe injection system. The bushing flange (318) also prevents liquid from leaking between the distal stopper bushing (310) and the distal stopper member (36) under pressure. In an alternative embodiment, the distal stopper bushing (310) and distal stopper member (36) are integrated into one solid rubber stopper member with the "pierce through" section and the funnel geometry molded in. A lubricious coating may be applied to the distal, proximal and/or circumferential sides of the distal stopper member (36) and/or the alignment funnel (314).

Figure 12E:
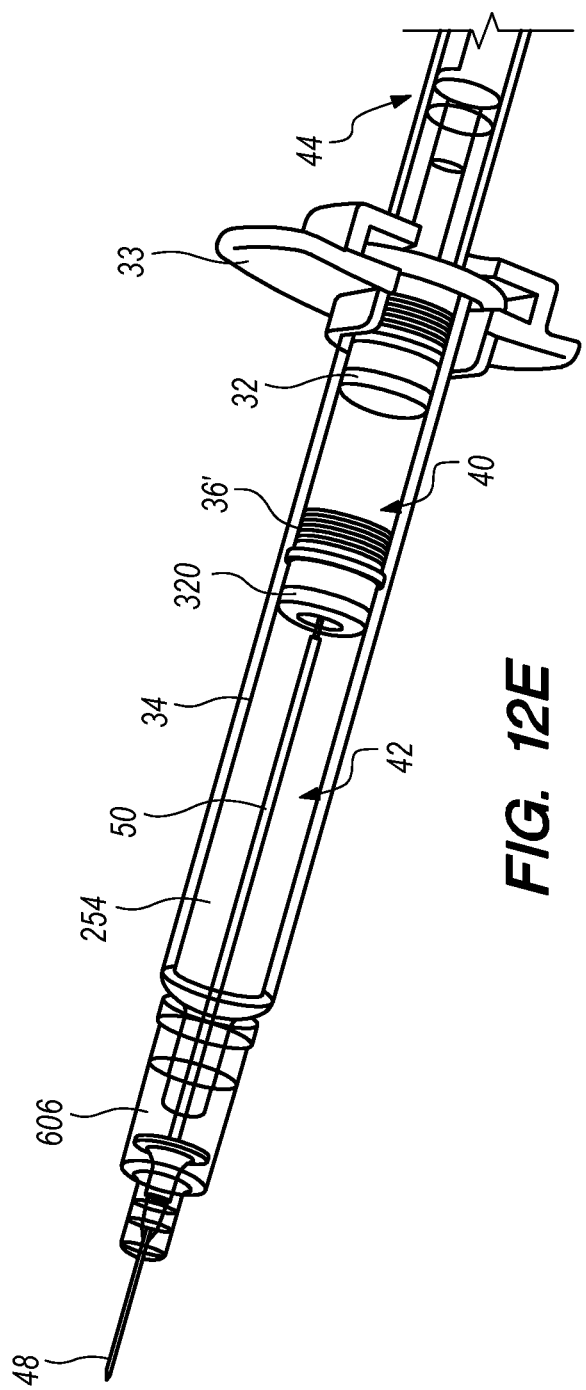
FIGS. 12E-12F illustrate various aspects of a guide disc according to one embodiment that can be used with dual chamber safe injection systems according to various embodiments.
Figure 12F:
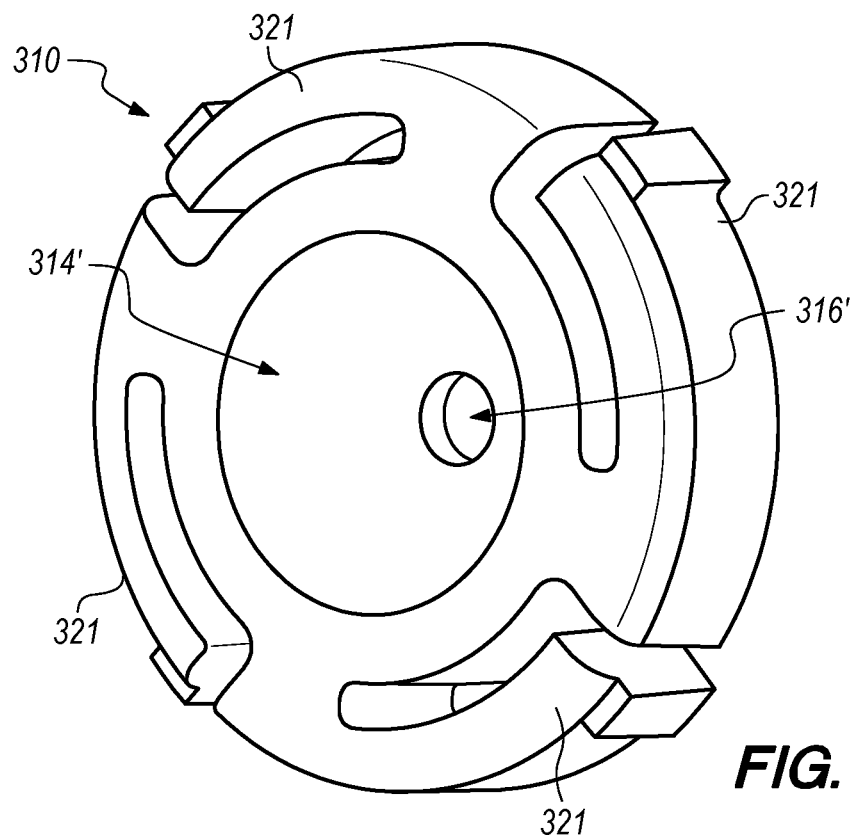

FIGS. 12E and 12F depict a guide disc (320) according to another embodiment with similar features to the distal stopper bushing (310) described above. The guide disc (320) also defines an alignment funnel (314') that papers proximally down to a receiving space (316'). The guide disc (320) also defines radial spring arms (321) which interface with the inner surface of the syringe body (34) to center the guide disc (320) and guide the needle proximal end (50) during piercing through the distal stopper member (36) and into the plunger rod assembly (44) for needle unlatching and/or retraction (as described in U.S. patent application Ser. No. 62/416,102, which was previously incorporated by reference herein). As shown in FIG. 12E, the guide disc (320) can be used with distal stopper members (36') that are installed in the conventional manner (i.e., facing distally).

Figure 13A:
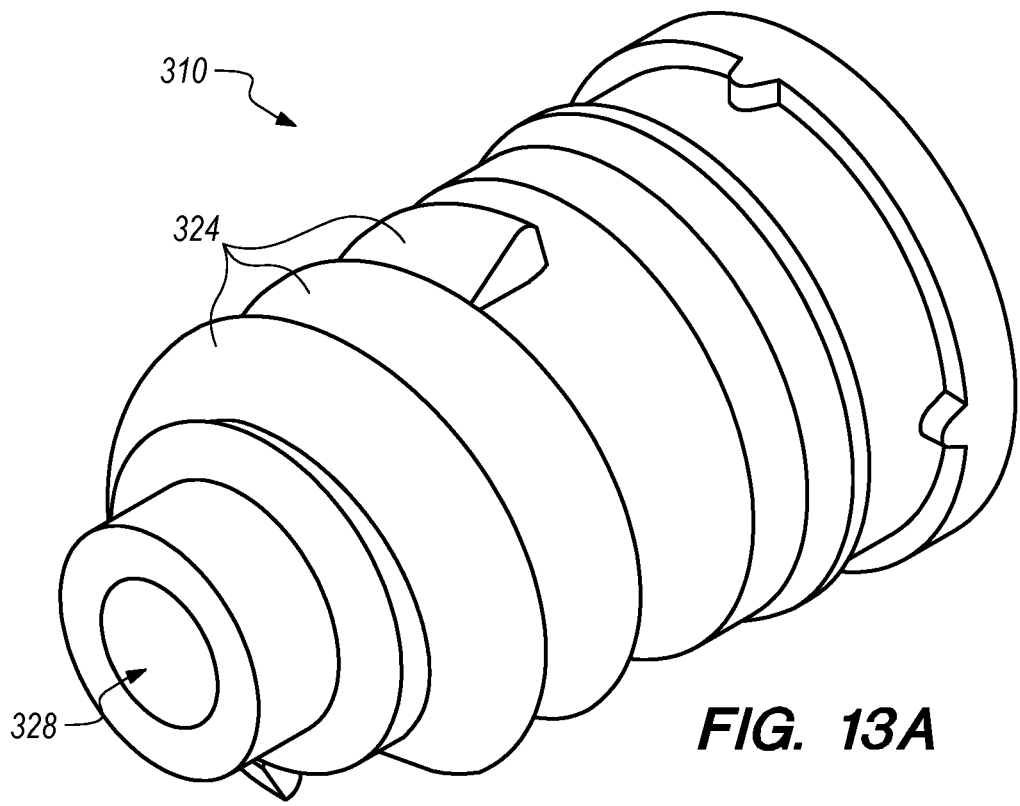
FIGS. 13A-13C illustrate various aspects of a proximal stopper screw according to one embodiment that can be used with dual chamber safe injection systems according to various embodiments.
Figure 13B:
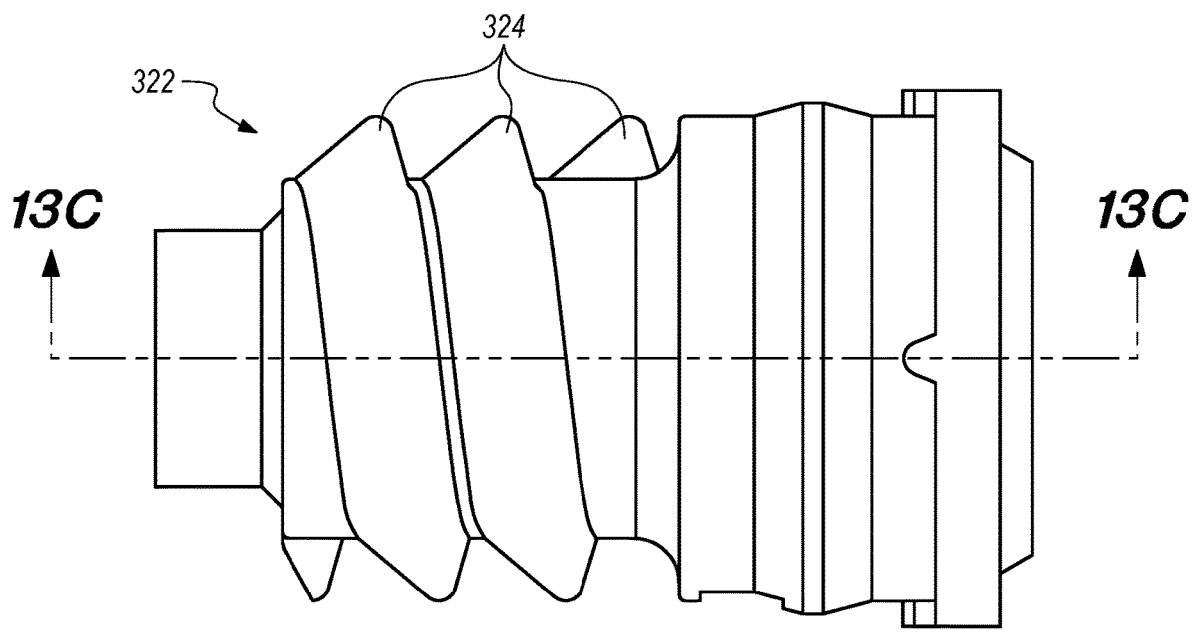
Figure 13C:
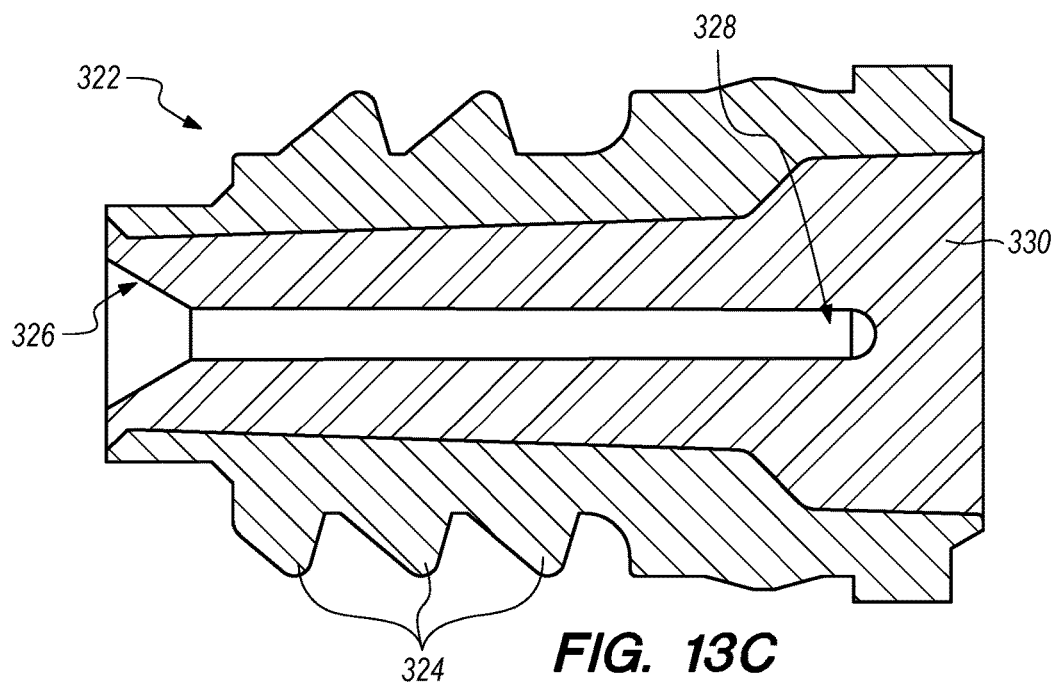
Figure 14E:
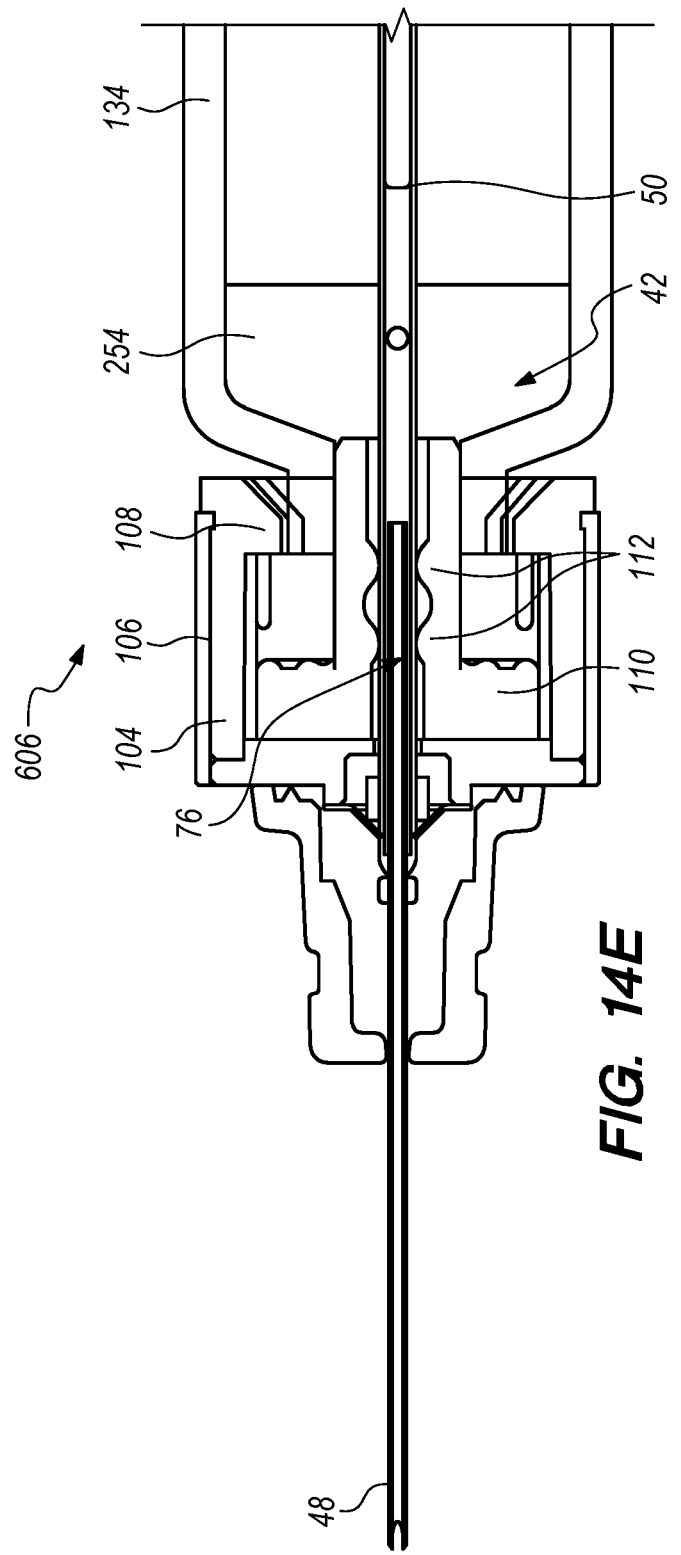
FIGS. 14A-16H illustrate various aspects of cartridge based dual chamber safe injection systems wherein a distal needle end/tip may be withdrawn into a protected configuration after use according to various embodiments.
Figure 15A:
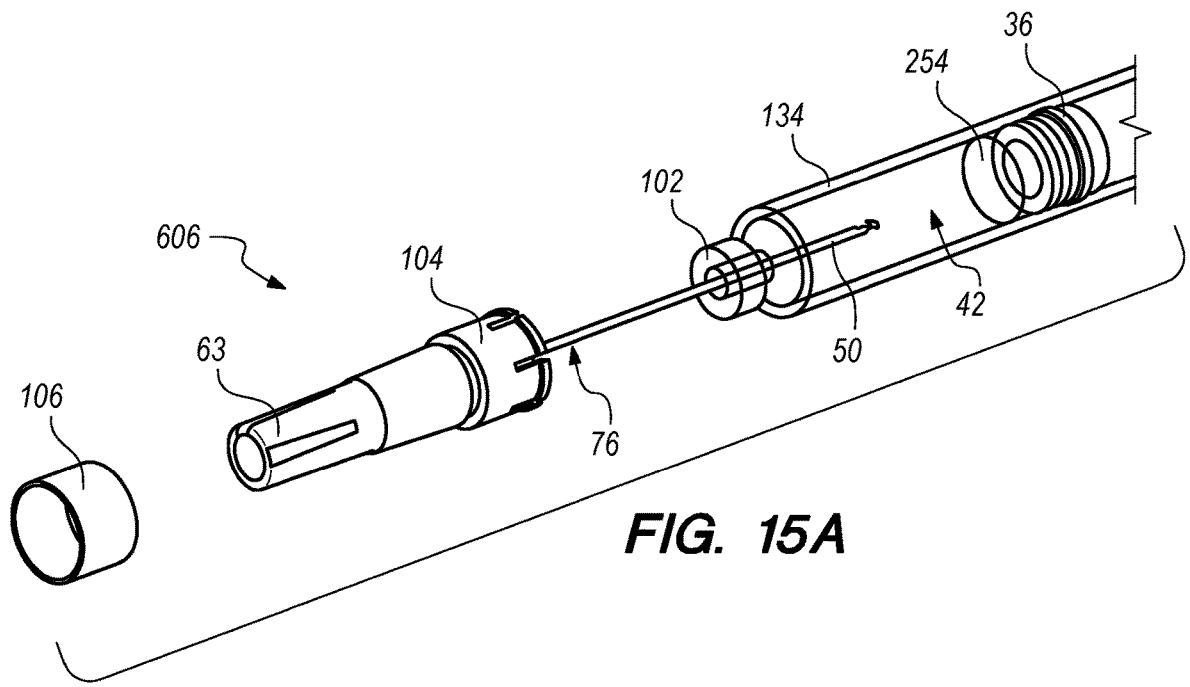
Figure 15B:
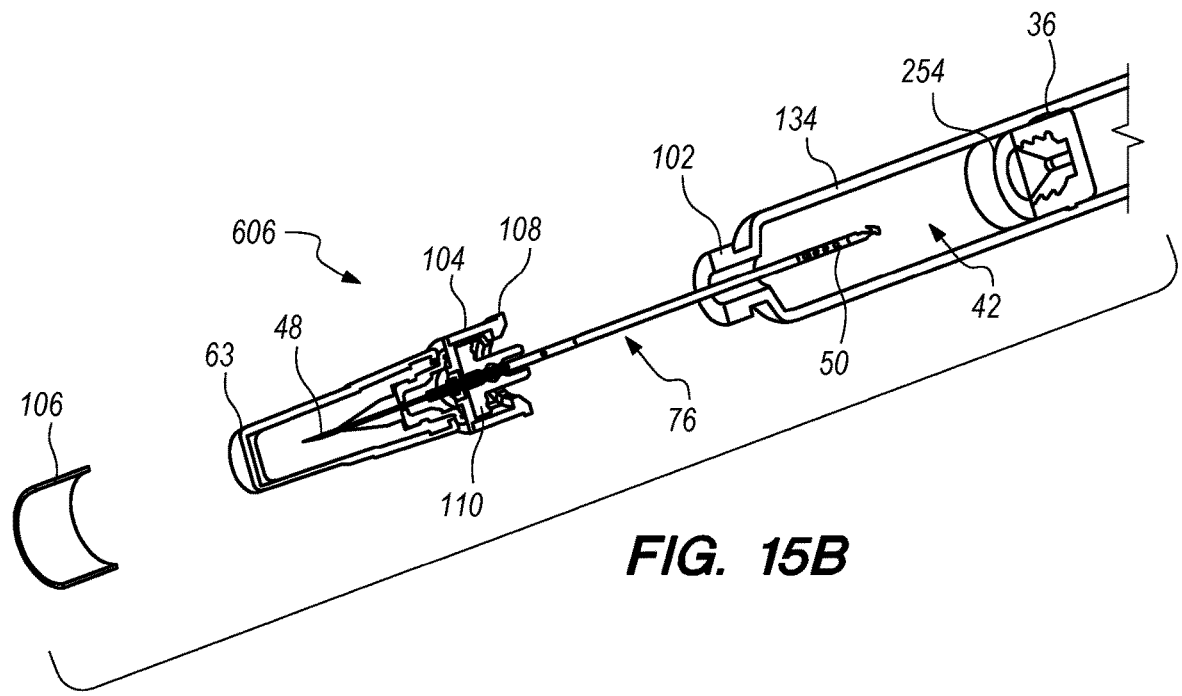
Figure 15C:
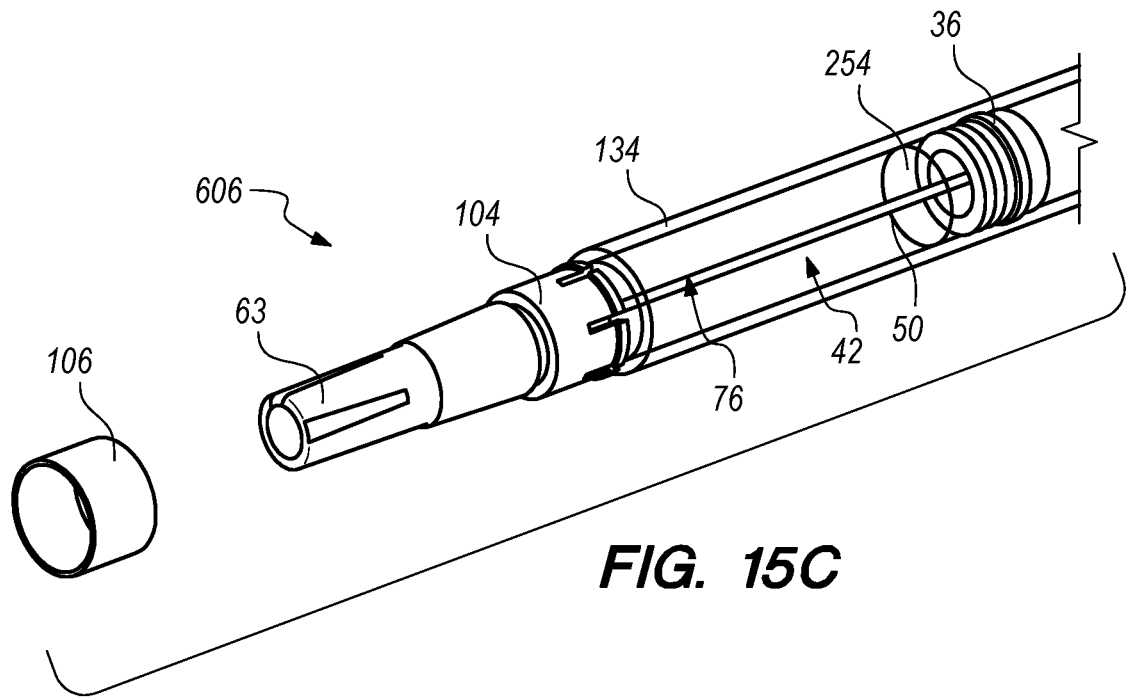
Figure 15D:
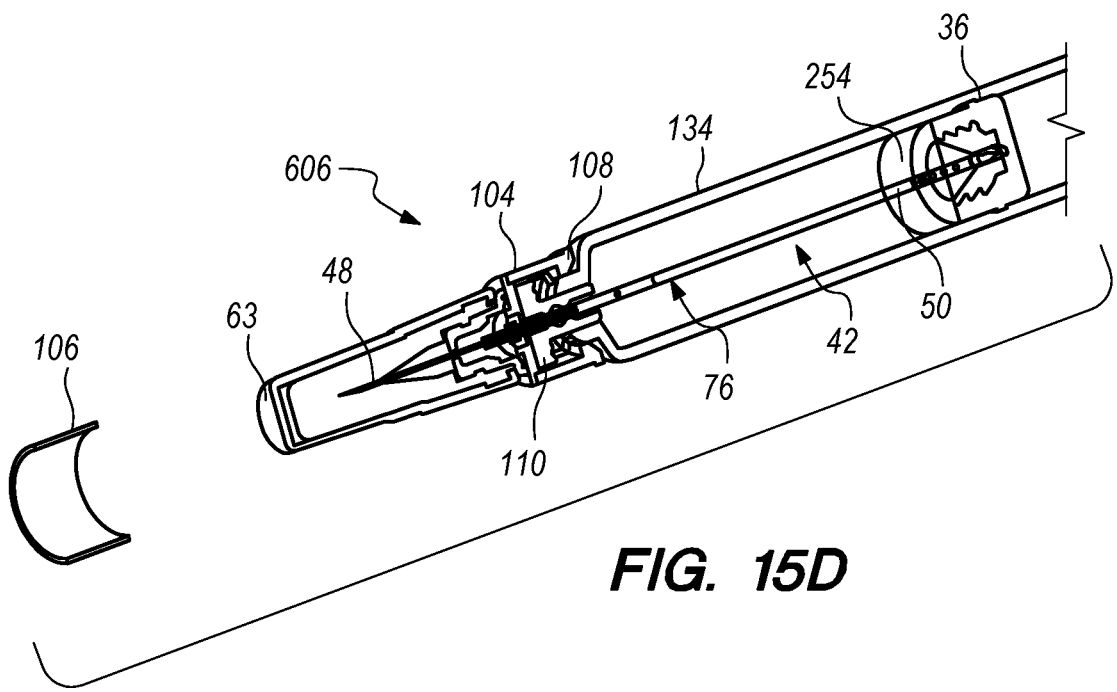
Figure 15E:
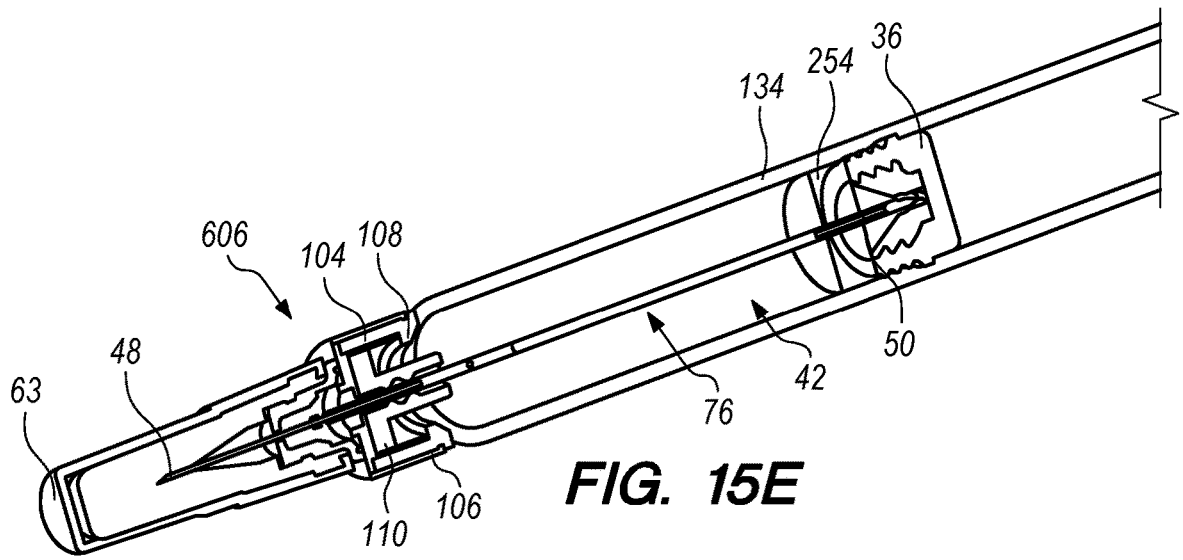
Figure 15F:
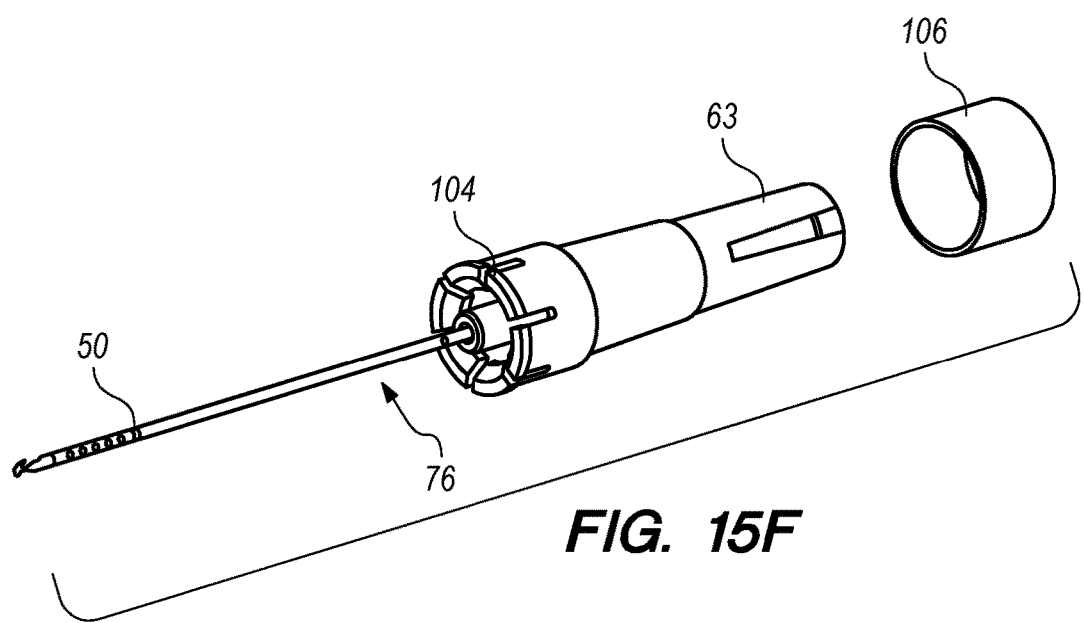

A proximal stopper screw (322) is secured to the proximal stopper member (32) using an interaction between male threads (324) on the proximal stopper screw (322) and the proximally facing female threads on the proximal stopper member (32). The proximal stopper screw (322) is shown in isolation in FIGS. 13A-13C. As shown in FIGS. 11E and 13C, the proximal stopper screw (322) defines an alignment funnel (326) and a sealing space (328). The sealing space (328) has a length greater than or equal to the distance between the most proximal opening (270) and the middle opening (266) (see FIGS. 6N and 6O).

After the needle proximal end (50) has pierced both the distal and proximal stopper members (36, 32), the alignment funnel (326) is configured to guide the needle proximal end (50) into the sealing space (328). During the early injection phase, the middle opening (266) remains in the distal medicine chamber (42), providing a fluid path through the transfer pipe (46) into the plunger assembly (44). The sealing space (328) of the proximal stopper screw (322) is configured to prevent liquid (e.g., mixed medication solution (272)) from traveling retrograde in the middle opening (266) through the transfer pipe (46) and out the proximal openings (270). The proximal stopper screw (322) has a proximal septum (330) that maintains the seal preventing retrograde liquid travel until the middle opening (266) is disposed in the proximal stopper screw (322) and sealed thereby. The proximal stopper screw (322) may be made with a rigid plastic portion (including the male threads (324)) and a rubber or elastomer portion defining the alignment funnel (326) and the sealing space (328), and including the proximal septum (330).

Exemplary Dual Chamber Safe Cartridge Systems

FIGS. 14A and 14B respectively depict similar sized cartridge (134) and syringe body (34). Both the cartridge (134) and the syringe body (34) may be made from glass. While the syringe body (34) is configured for use in an injection system, the cartridge (134) is configured for storage of substances (e.g., medications). This results in several differences between cartridges (134) and syringe bodies (34). For instance, while the proximal end of the syringe body (34) includes a conventional integral syringe flange (38), the proximal end of the cartridge (134) does not include an integral flange. Further, while the distal end of the syringe body (34) includes a Luer taper configured to allow snapping engagement of a needle coupling assembly (606), the distal end of the cartridge (134) includes a flange (102) configured for securing a conventional cartridge seal (not shown). Conventional cartridge seals include an elastically compressible sealing member at least partially surrounded by an elastically deformable closure (e.g., an aluminum ring). As shown in FIGS. 14A and 14B, the distal opening of the cartridge (134) is significantly larger than the corresponding distal opening of the syringe body (34). This provides more airflow for lyophilization as described above.

FIGS. 14C and 14D depict a dual chamber safe injection system built around a cartridge (134) instead of a syringe body (34). The substitution of a cartridge (134) for a syringe body (34) results in two changes to the dual chamber safe injection system. The first is that the small diameter flange (33) is glued or press fit onto the cartridge (134) instead of being coupled to a syringe flange.

The second difference for dual chamber safe injection systems built around a cartridge (134) involves connection of the needle coupling assembly (606) to the distal end of the cartridge (134) as shown in FIGS. 14C-16H. As shown in FIG. 14E, the needle coupling assembly (606) is coupled to the distal end of the cartridge (134) using a collet (104) and a sleeve (106). The collet (104) may be welded onto a base plate of the needle coupling assembly (606). FIGS. 15A and 15B show a system assembly step in which a needle distal portion (50) of a needle coupling assembly (606) is inserted into a distal medicine chamber (42). As shown in FIGS. 15B and 15D, the collet (104) is expandable to partially pass proximally over the flange (102) on the distal end of the cartridge (134). As shown in FIGS. 15D and 15E after a proximal end (108) of the collet (104) has passed proximally of the flange (102), the sleeve (106) can be slid proximally over the collet (104) to prevent the collet (104) from opening and releasing from the flange (102). Securing the sleeve (106) over the collet (104) on the flange (102) secures the needle coupling assembly (606) to the distal end of the cartridge (134).

Figure 16A:
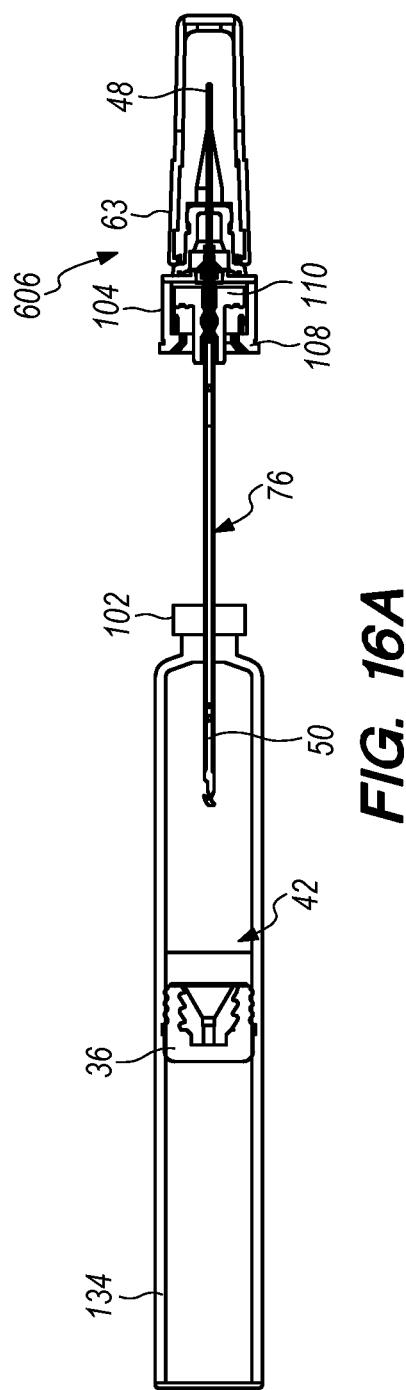
Figure 16B:
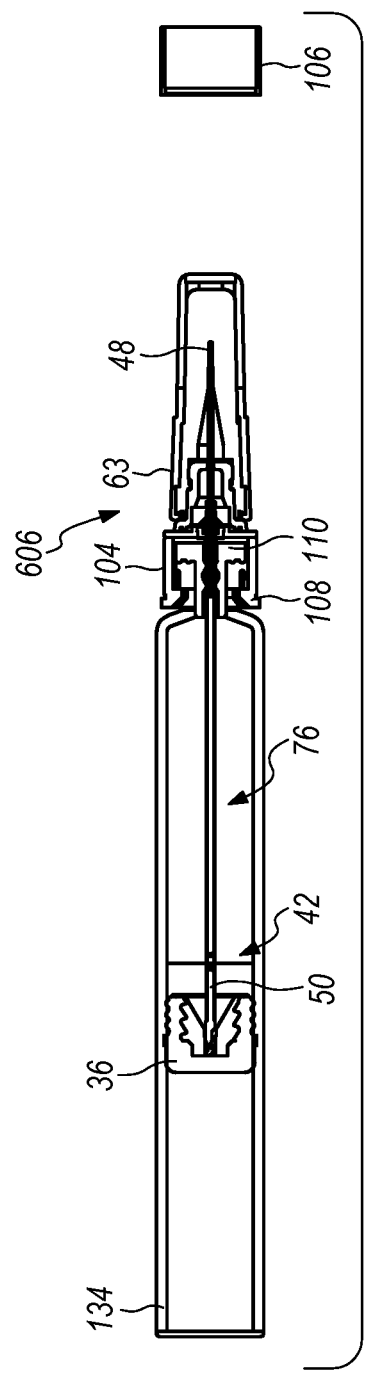
Figure 16E:
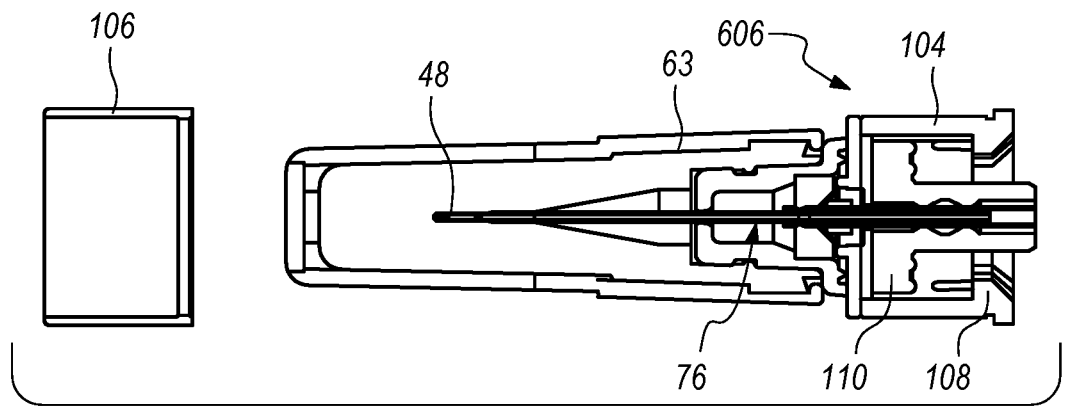
Figure 16F:
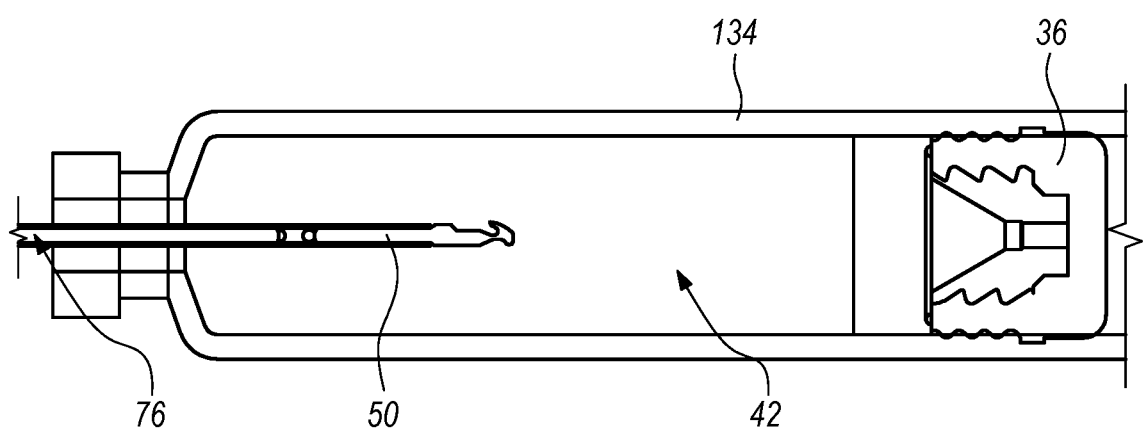

FIGS. 16A-16C again show the attachment of the coupling assembly (606) to the distal end of the cartridge (134). FIGS. 16A and 16B also depict the needle proximal end (50), showing the alignment funnel (314) on the distal stopper bushing (310) guiding the needle proximal and (50) into the receiving space (316) during assembly of the dual chamber safe injection system. FIG. 16D shows the attachment of the small diameter flange (33) to the proximal end of the cartridge (134), and insertion of the plunger assembly (44) and the proximal stopper member (32) secures thereto into the cartridge (134). The dual chamber safe injection system with the cartridge (134) depicted in FIG. 16D is ready to transport, store, and use (i.e., mixing, injecting and automatic retraction) following steps exactly identical to those depicted for the dual chamber safe injection system with the syringe in FIGS. 7A-7P.

Figure 16G:
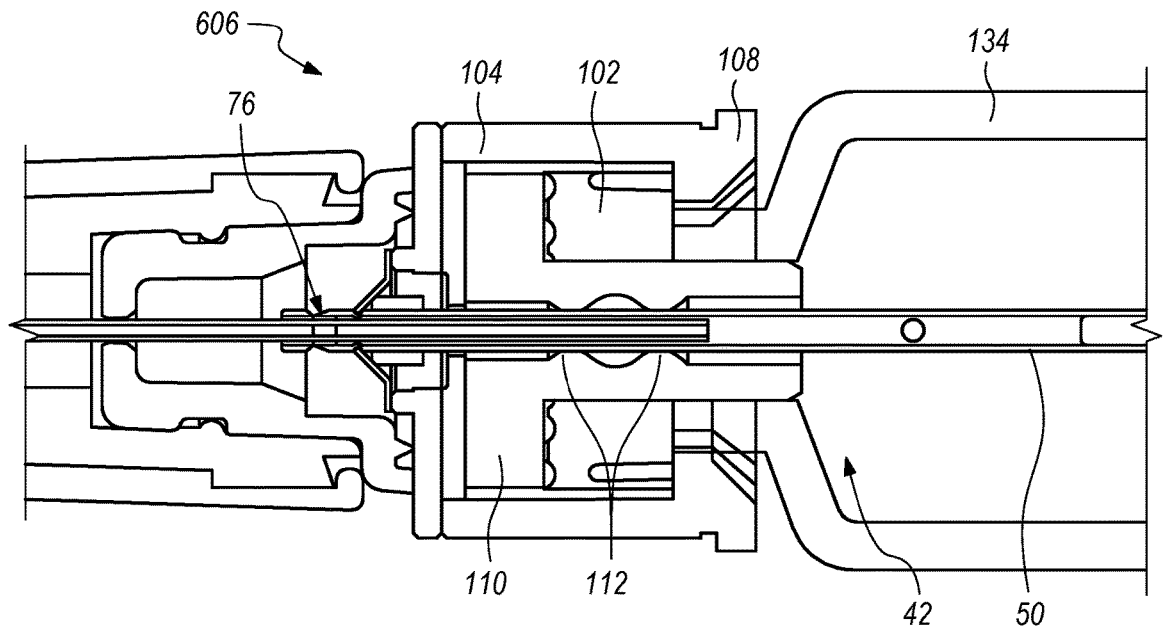
Figure 16H:
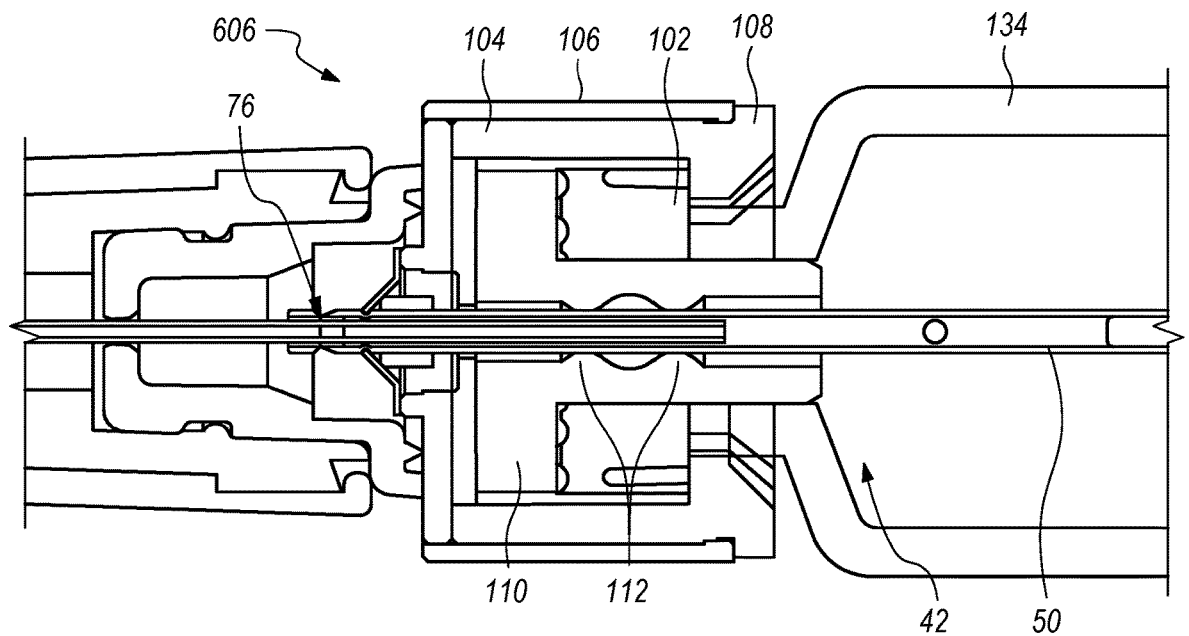
Figure 17C:
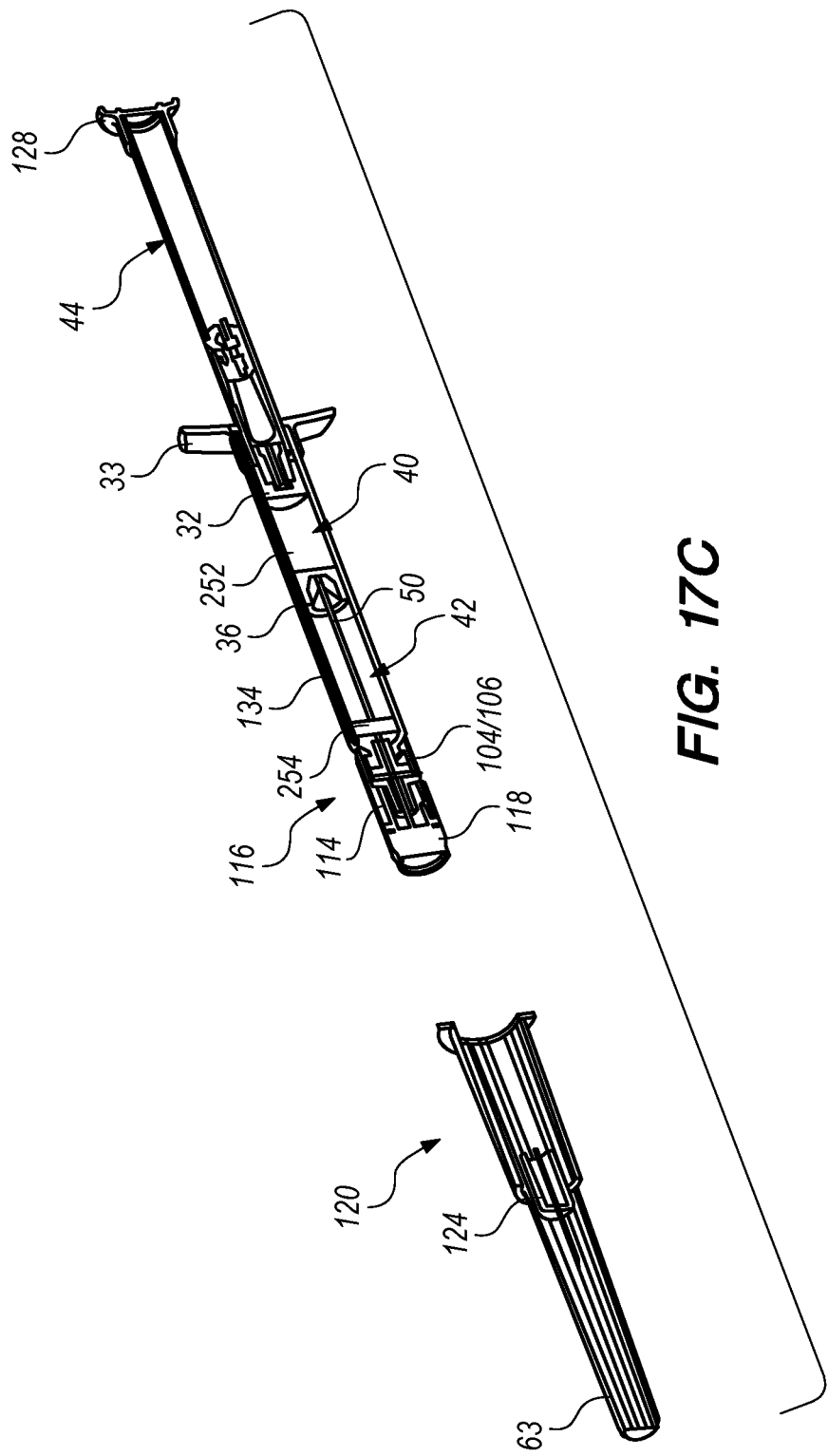
FIGS. 17A-18G illustrate various aspects of dual chamber safe injection systems configured to have a user attachable needle which utilizes a Luer type coupling according to various embodiments.
Figure 17D:
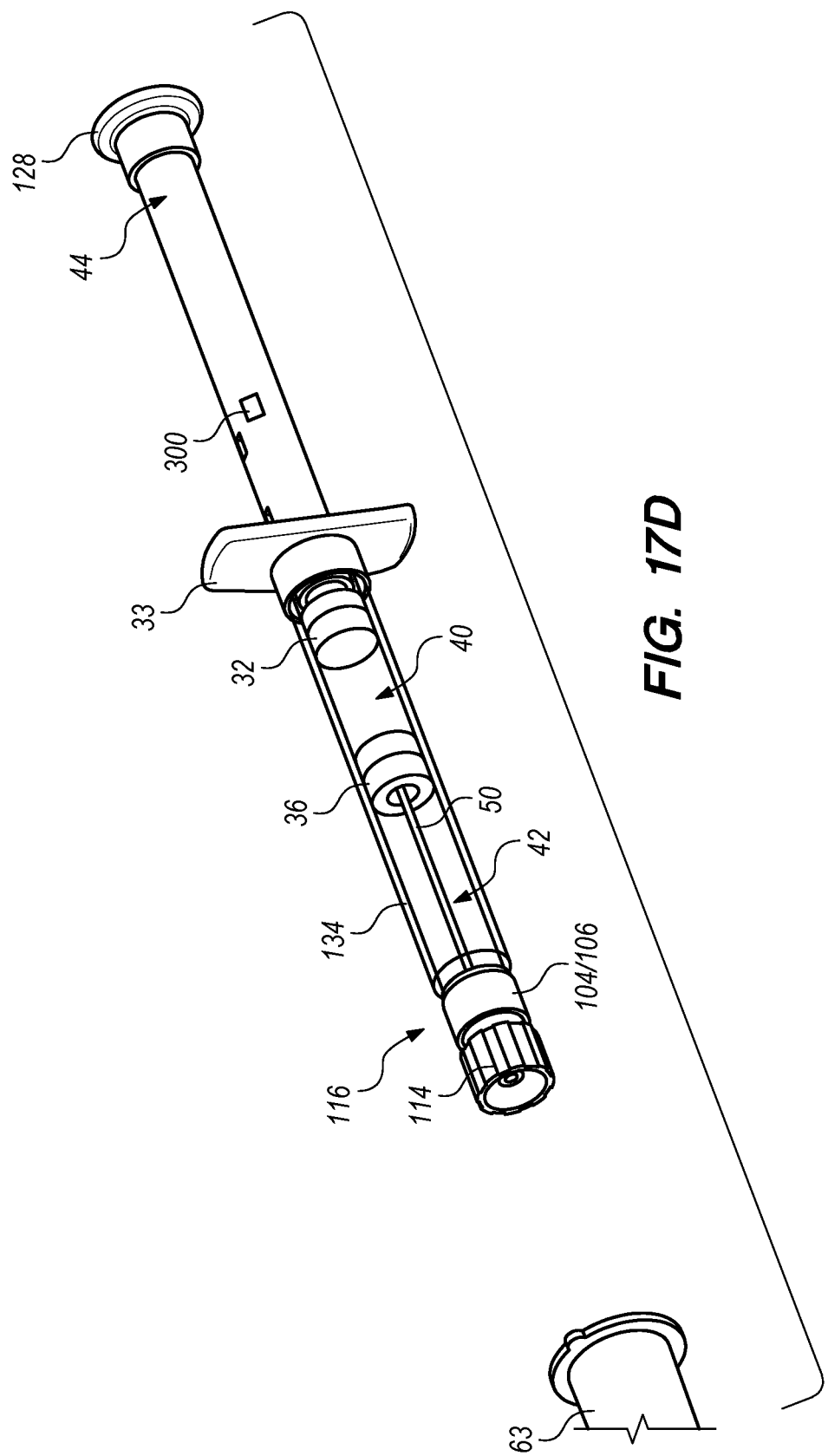
Figure 17G:
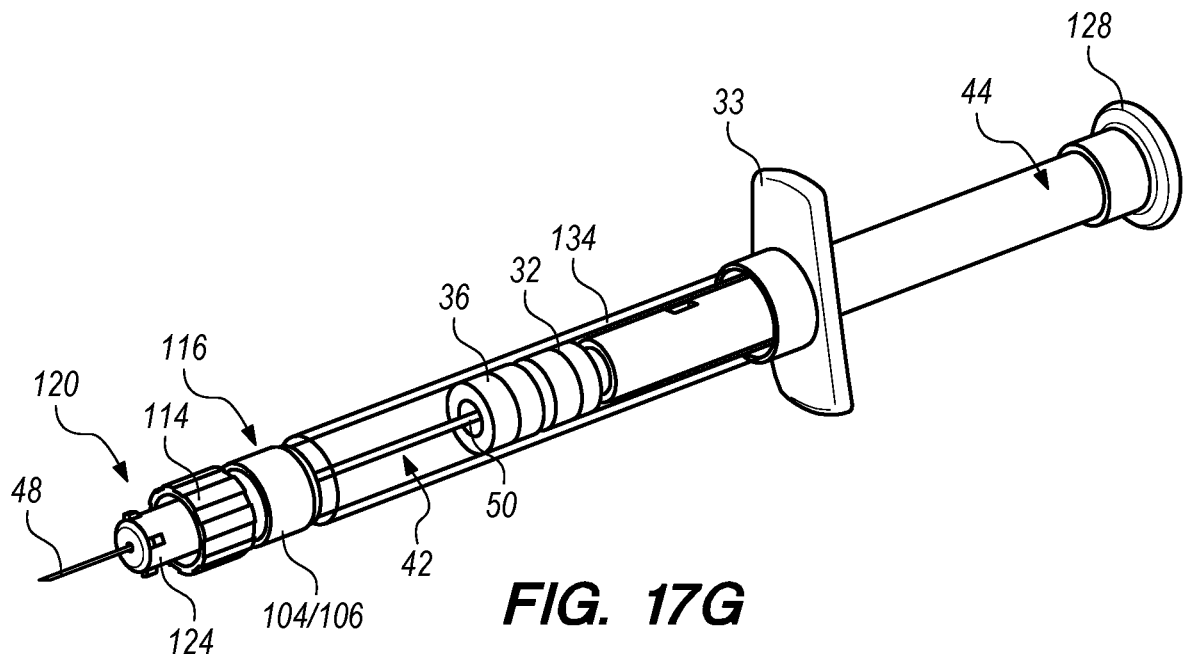
Figure 17H:
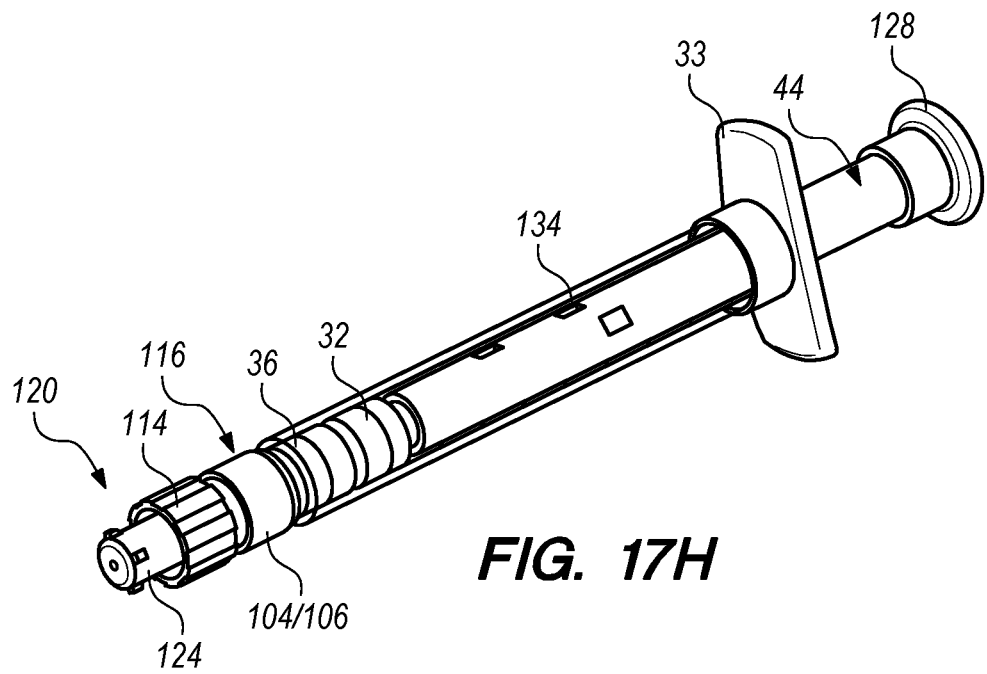
Figure 17I:
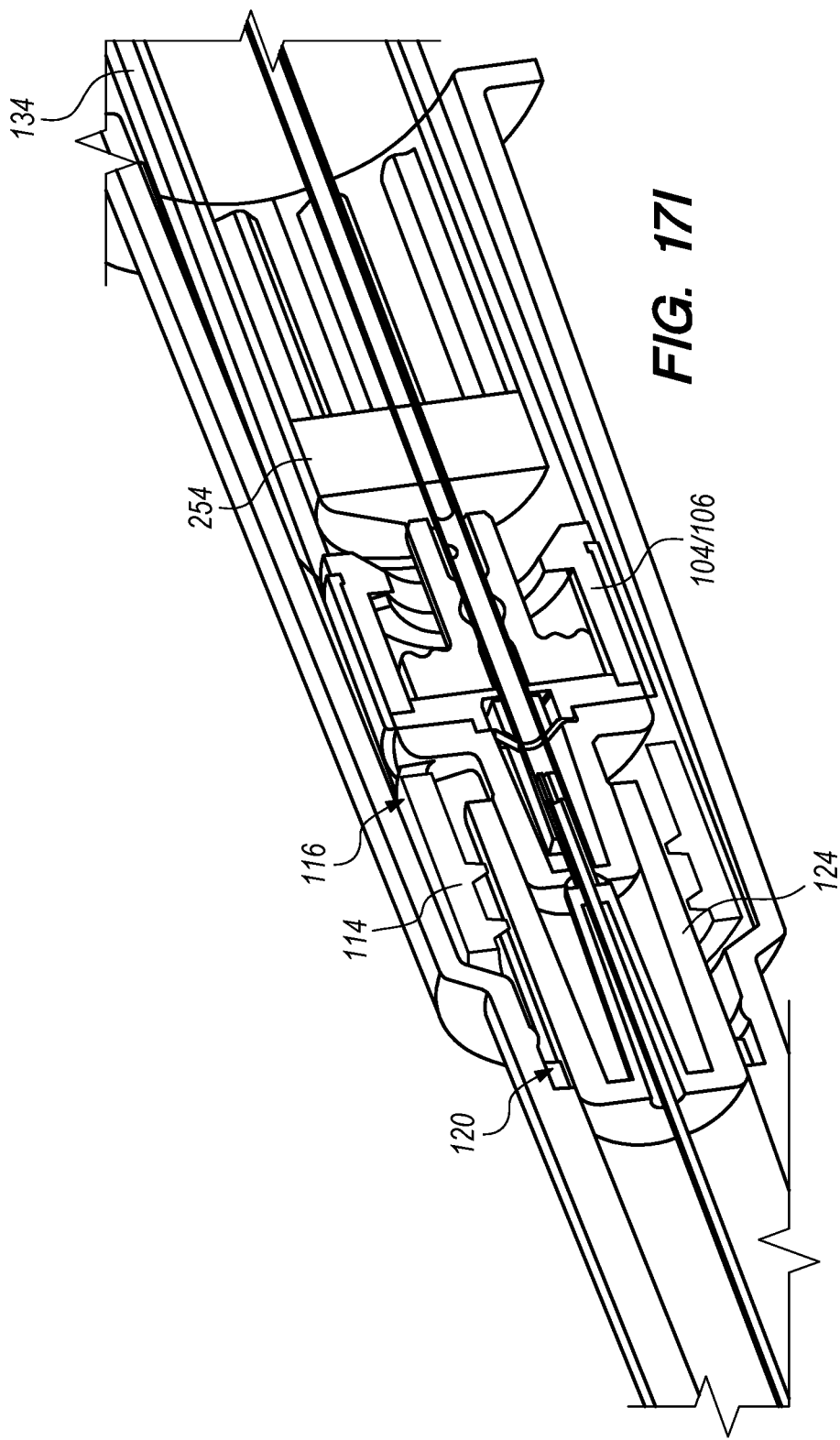
Figure 17J:
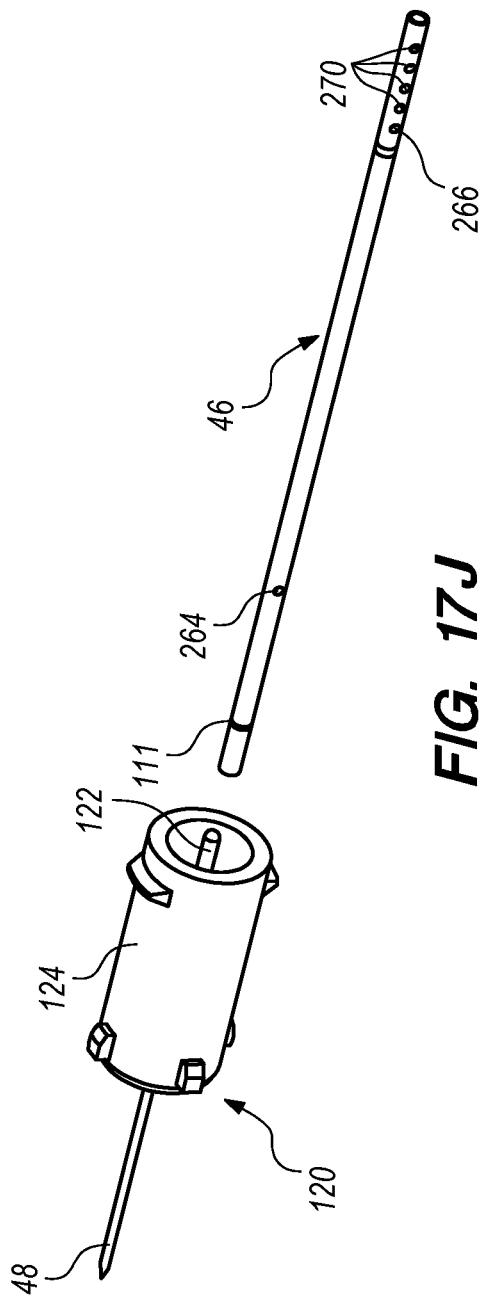
Figure 17K:
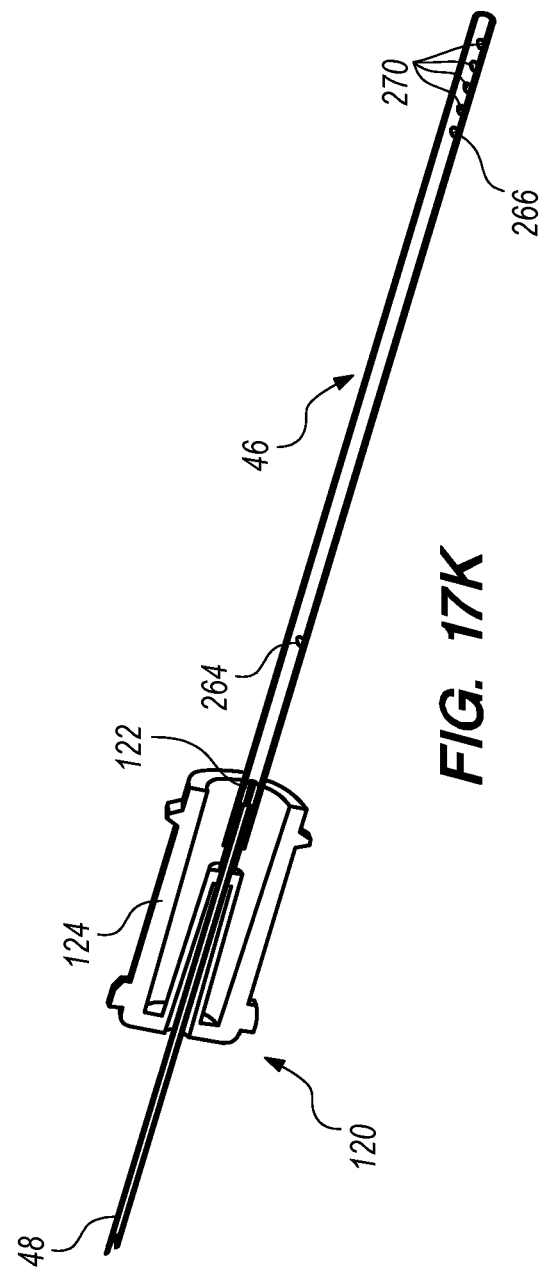
Figure 18A:
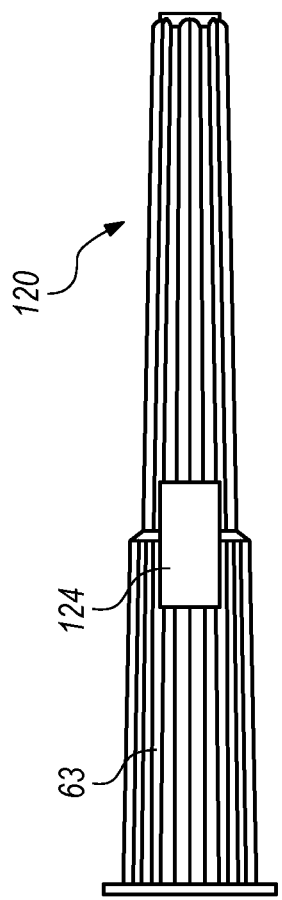
Figure 18B:
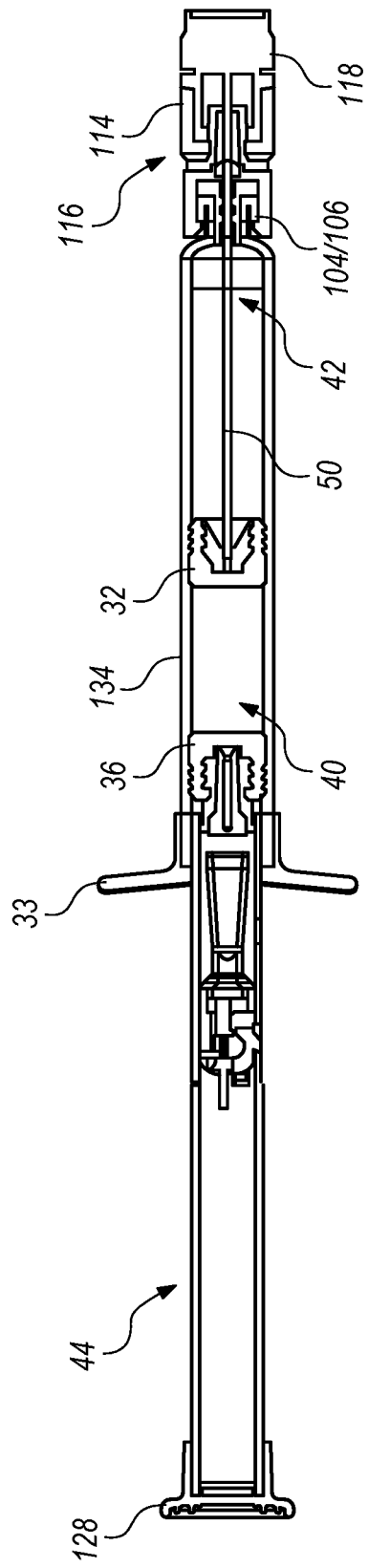
Figure 18C:
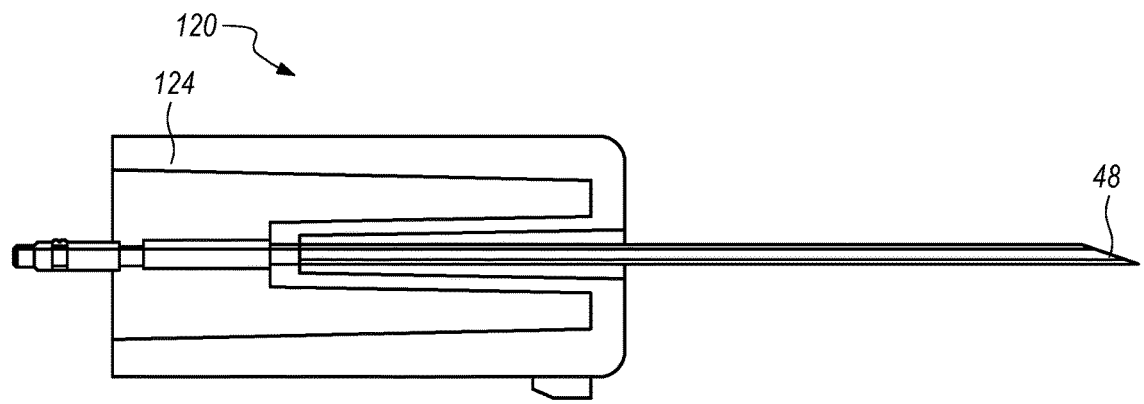
Figure 18D:
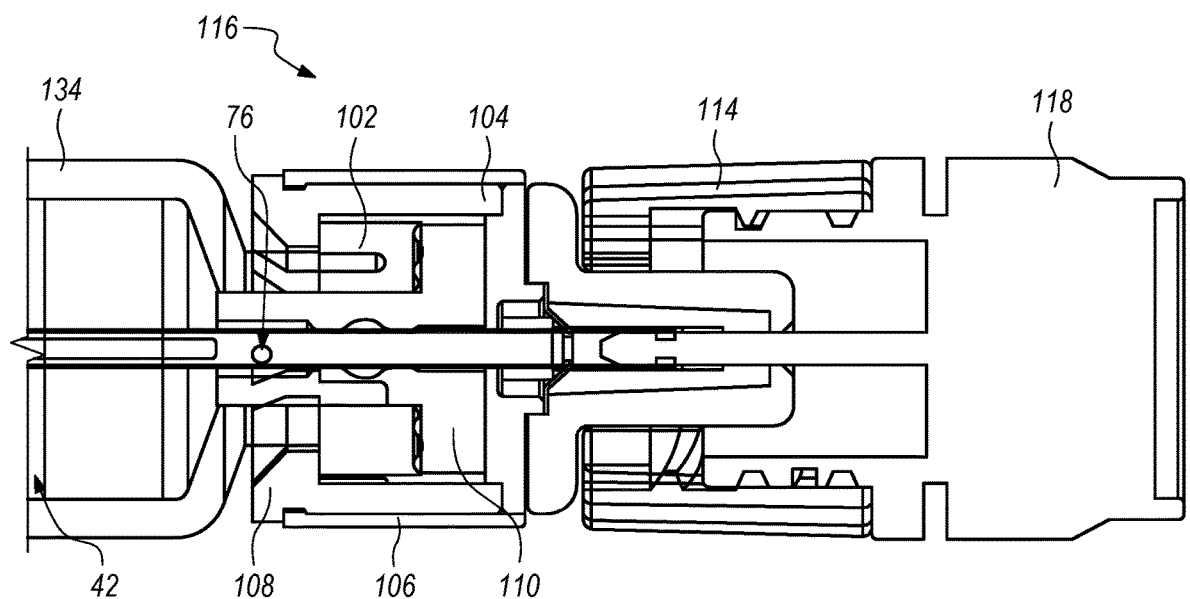
Figure 18E:
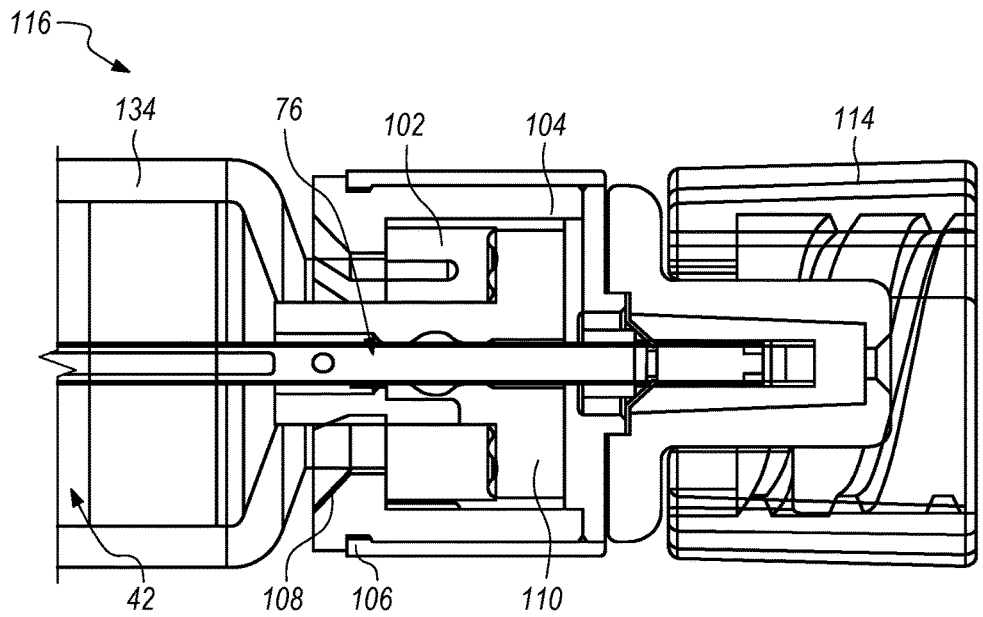
Figure 18F:
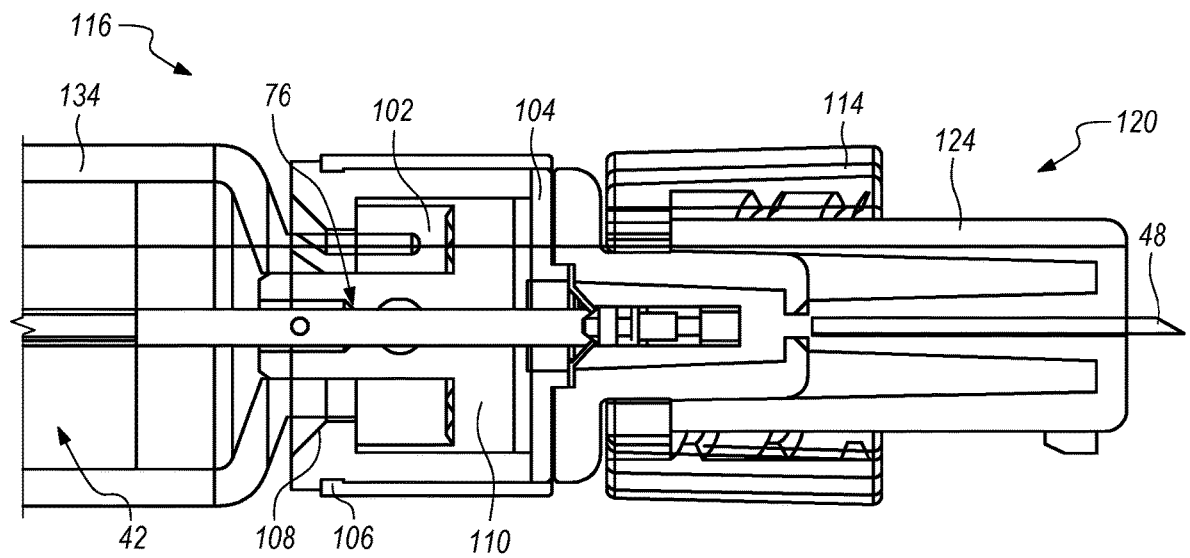
Figure 18G:
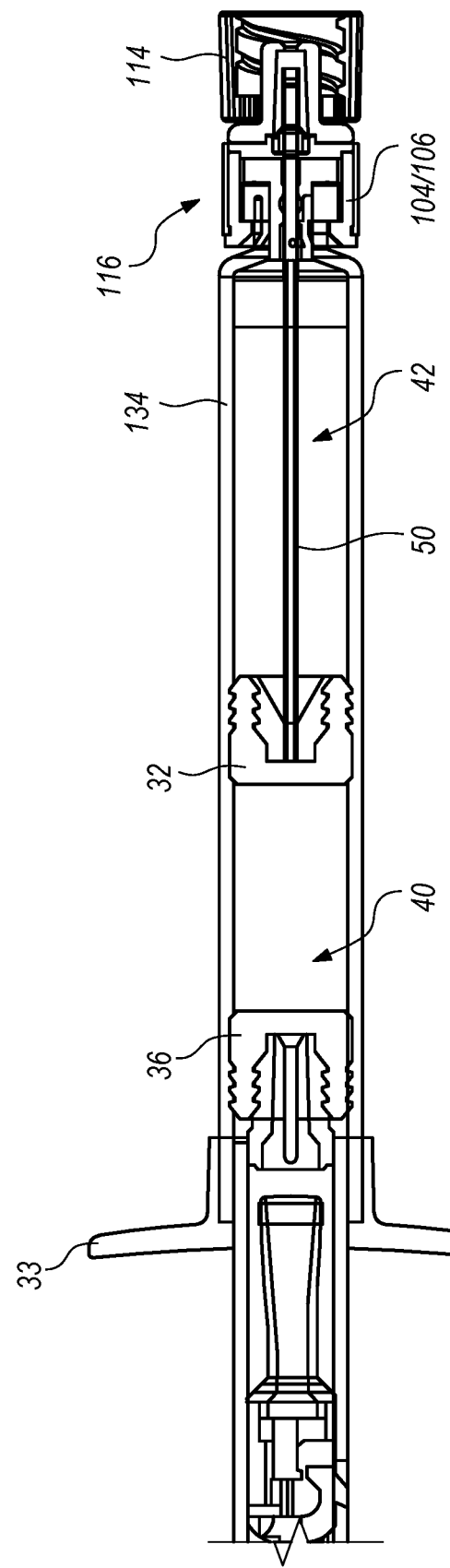

FIGS. 16G and 16H depict in detail the interface between the collet (104) and the flange (102) both without (FIG. 16G) and with (FIG. 16H) the sleeve (106). FIGS. 16G and 16H also depict a needle seal (110) disposed in the needle coupling assembly (606) and configured to fluidly seal the annular space between the inner diameter of the opening in the distal end of the cartridge (134) and the outer diameter of the needle spine assembly (76). The needle seal (110) may be made from an elastically deformable material such as rubber. The needle seal (110) also includes a pair of glands (112) that extend into an inner diameter of the needle seal (110). The glands (112) function like two O-rings that seal against the needle spine assembly (76).

Various features of the dual chamber safe injection system built around a cartridge (134) can also be used with auto injectors or pen injectors. The cartridges of these systems may also incorporate an integral glass or plastic finger flange similar to what is employed on the syringe based systems.

Exemplary Dual Chamber Safe Injection Systems with Luer Connectors

FIGS. 17A-19D depict various dual chamber safe injection systems with Luer connectors (114) at their distal ends. For use with a cartridge (134), as shown in FIGS. 17A-17H, a female Luer lock connector (114) with internal threads is attached to a collet (104) and a sleeve (106) like the ones depicted in FIGS. 14A-16H and described above to form a needle hub (116). The collet (104) and the sleeve (106) can be used to attach the needle hub (116) to the distal end of the cartridge (134) as described above for attaching the needle coupling assembly (606) to the cartridge (134) depicted in FIGS. 14A-16H. The distal end of the female Luer lock connector (114) is temporarily sealed with a removable Luer cap (118). Once the needle hub (116) is attached to the cartridge (134), the Luer cap (118) can be removed and a Luer needle (120) may be attached to the needle hub (116) and the dual chamber safe injection system using the female Luer lock connector (114) as shown in FIG. 17E.

After the Luer needle (120) is attached to the needle hub (116) and the dual chamber safe injection system, the system with is ready to transport, store, and use (i.e., mixing, injecting and automatic retraction) following steps exactly identical to those depicted for the dual chamber safe injection system with the syringe in FIGS. 7A-7P. Mixing, injection and retraction steps similar to those depicted in FIGS. 7A-7P are depicted for a dual chamber safe injection system with a female Luer lock connector (114) in FIGS. 17A-17H.

Using a female Luer lock connector (114) and a replaceable Luer needle (120) leads to one additional complication. A proximal end (122) of the Luer needle (120) must be connected to a transfer pipe (46) while connecting the Luer needle (120) to the female Luer lock connector (114) on the needle hub (116). During attachment of the Luer needle (120), a needle cover member (63) is configured to guide the Luer needle (120) into the needle hub (116), thereby aligning the proximal end (122) of the Luer needle (120) with the transfer pipe (46) to improve connection between the Luer needle (120) and the transfer pipe (46). Guiding needle cover members are described in U.S. patent application Ser. No. 14/696,342, which was previously incorporated by reference herein. FIGS. 17J-17K and 18C-18F show the connection between the Luer needle (120) and the transfer pipe (46). As seen in these figures, the male Luer lock connector (124) with external threads on the Luer needle (120) guide the proximal end (122) of the Luer needle (120) into the transfer pipe (46) for a secure connection there between. The threads on the Luer lock connectors (114, 124) force the proximal end (122) of the Luer needle (120) into the transfer pipe (46) for a hermetic press fit or snap fit. The distal end of the transfer pipe (46) also includes a latch groove (111) configured to interact with one or more cantilevered latch members (616) to prevent the transfer pipe from being forced proximally into the cartridge (134) during attachment of the Luer needle (120), as described below.

Figure 19A:
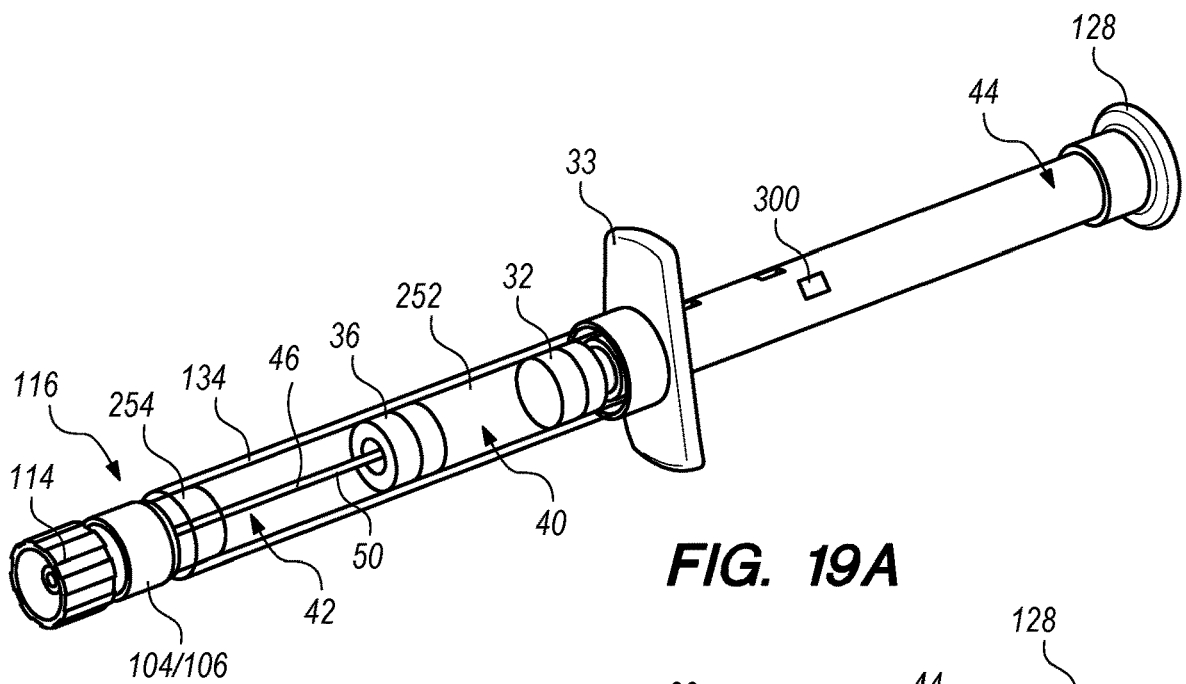
FIGS. 19A-19D illustrate a dual chamber medicine mixing and delivery system for delivering a medicine to a patient via an IV port or other delivery method not involving an injection into the patient.
Figure 19B:
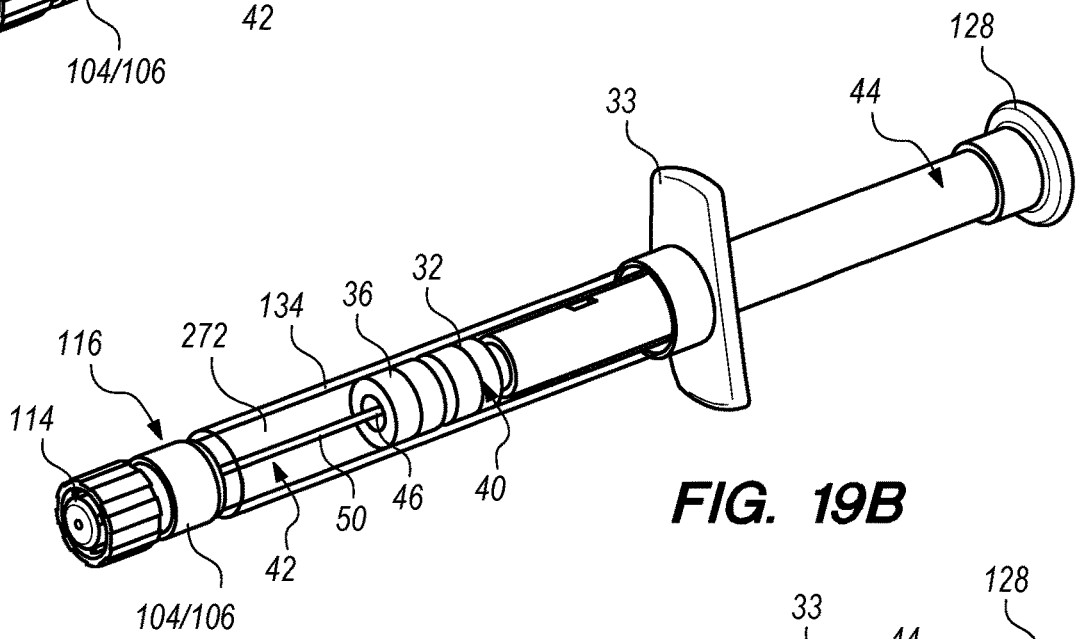
Figure 19C:
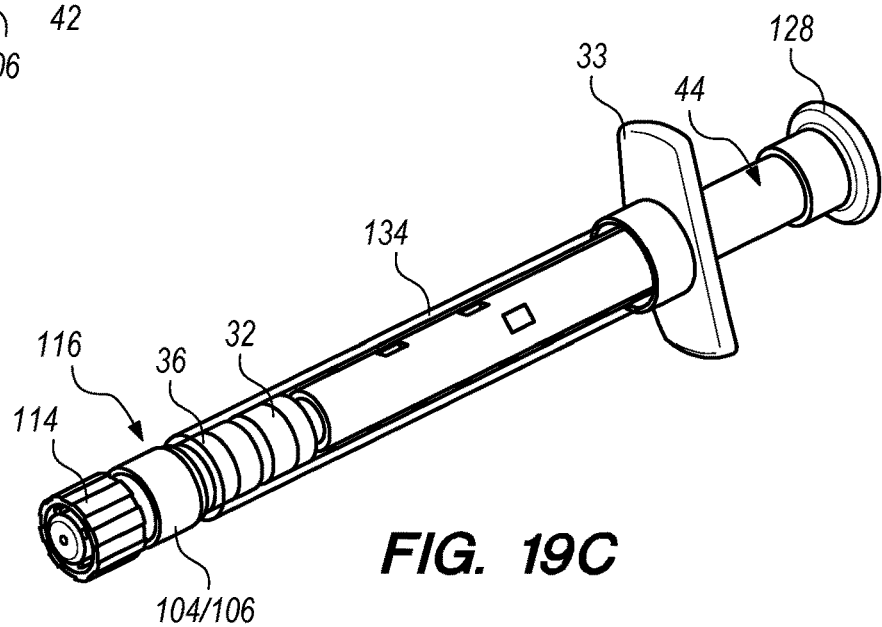
Figure 19D:
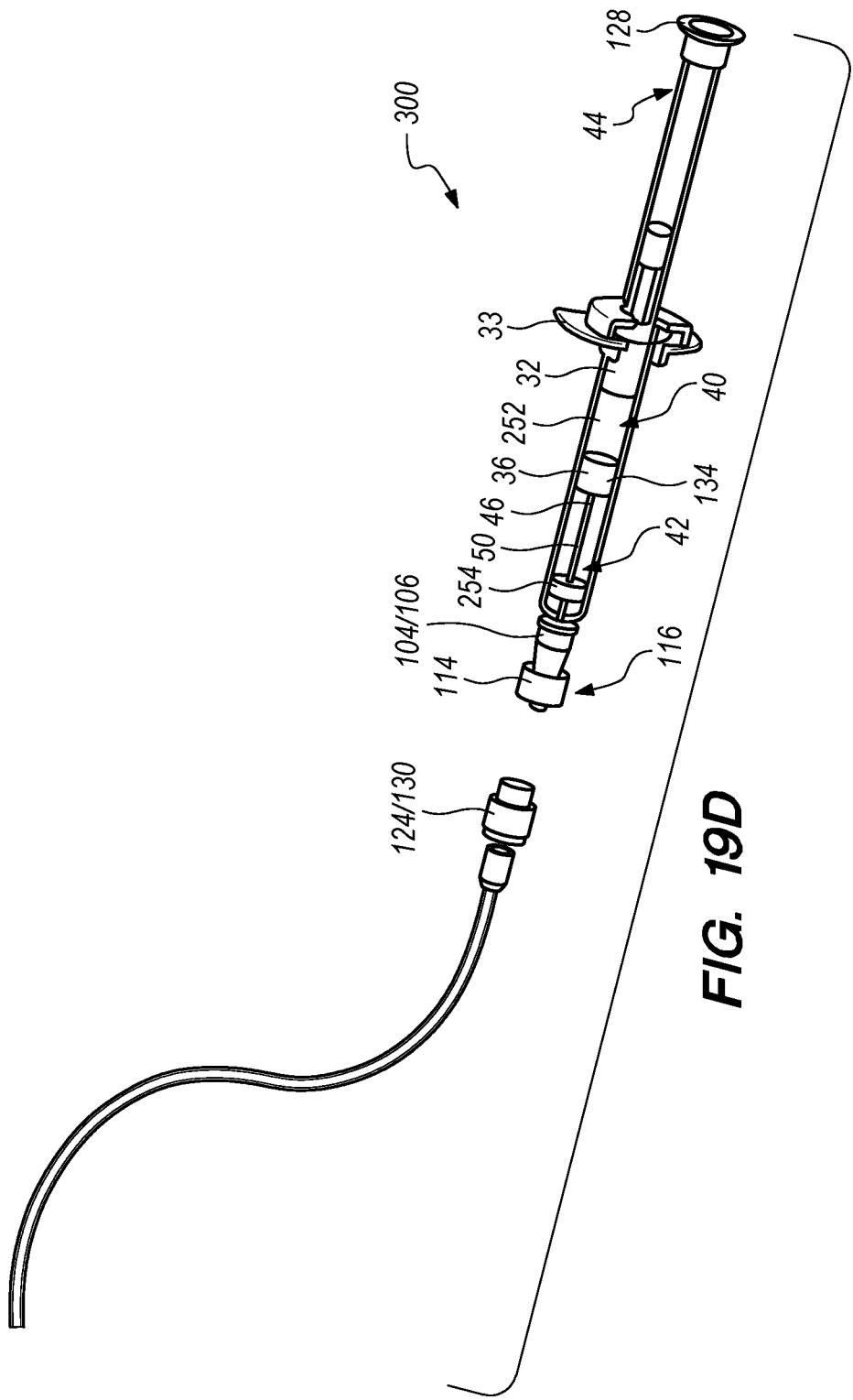

FIGS. 19A-19D illustrate an embodiment wherein a dual chamber safe injection system with a female Luer lock connector (114) at its distal end is used for mixture (with or without a Luer cap (118) on) and injection without a Luer needle. The connector (114) may also be a Luer taper or Luer slip, or other fluid connector. As shown in FIG. 19D, the dual chamber safe injection system can be connected to any Luer lock access port (130) such as that connected to an IV tube and an IV bag. In such an embodiment, the dual chamber safe injection system does not retract because the retraction mechanism is not necessary as there is no sharp needle. In this case, the transfer pipe (46) may be stationary to allow for transfer of the liquid from the proximal medicine chamber (40) to the distal medicine chamber (42), and then allow for the injection of the mixed medicine (272) into the IV tube or other injection systems.

While the dual chamber safe injection system with Luer connector embodiments depicted in FIGS. 17A-19D involve cartridges, Luer connectors can also be used with syringes and other dual chamber safe injection systems.

Exemplary Safe Injection Systems for Metal Sensitive Medicines

Figure 20A:
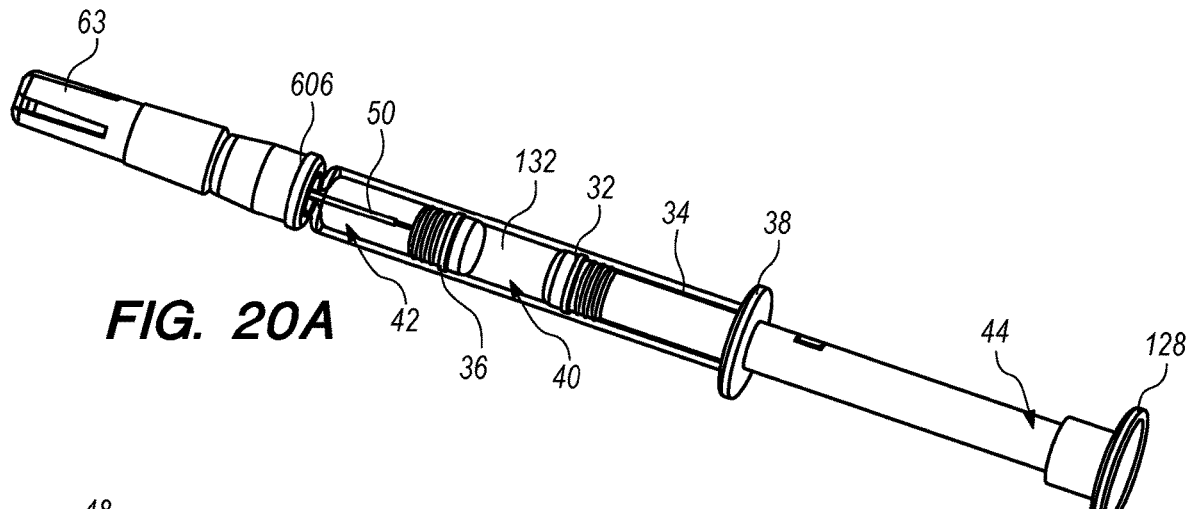
FIGS. 20A-20D illustrate a safe injection system according to one embodiment for storage and delivery of a drug which is sensitive to contact with stainless steel.

An increasing number of injectables (e.g., medicines) are sensitive to degradation during storage by contact with metals, such as that found on a needle. FIGS. 20A-20D depict use of a prefilled dual chamber safe injection system to minimize the exposure of such sensitive medicines to metal during storage. For instance, the sensitive medicine (132) can be prefilled in the system and stored in the proximal medicine chamber (40) as shown in FIG. 20A, which depicts a transport configuration for the dual chamber safe injection system. As such the sensitive medicine (132) is only exposed to the glass of the syringe body (34) and the hydrophilic or lubricious coatings (e.g., PTFE) on the proximal and distal stopper members (32, 36) during transportation and storage. The distal medicine chamber (42) contains only the needle proximal end (50) and does not contain any injectable. In effect, the distal stopper member (36) separates the sensitive medicine (132) from the metal needle proximal end (50) to which it is sensitive.

Figure 20B:
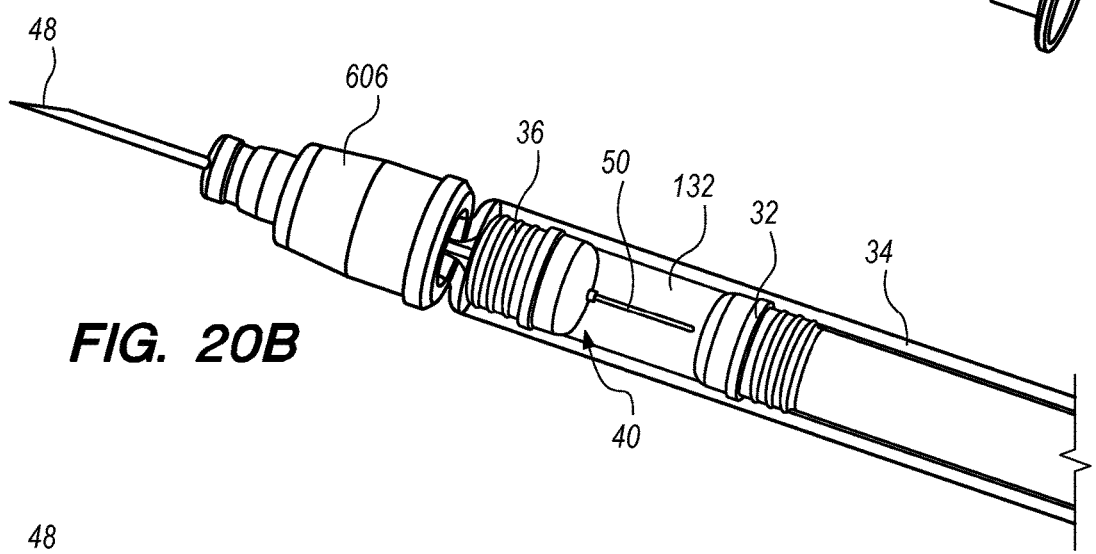
Figure 20C:
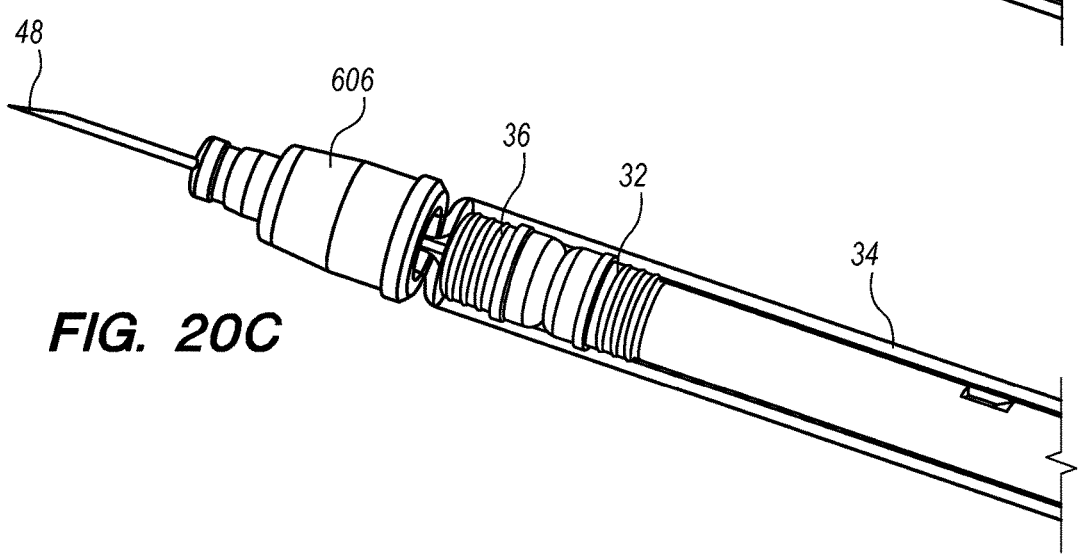
Figure 20D:
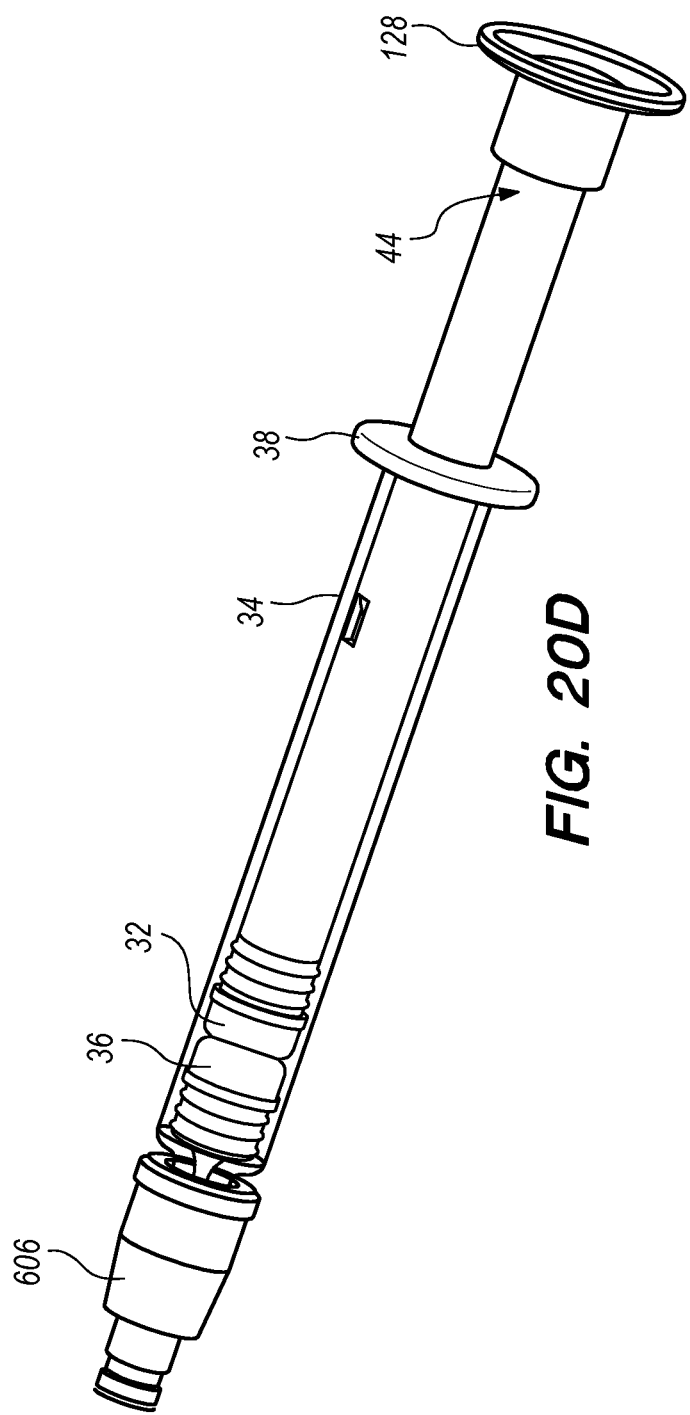

Directly before injection, a user applies pressure to the plunger manipulation interface (128), thereby pushing the proximal and distal stopper members (32, 36) and the sensitive medicine (132) contained there between distally. The needle proximal end (50) is configured such that it has a single opening located just proximal of the distal stopper member (36) when the distal stopper member (36) is positioned at a distal end of the syringe body (34), as shown in FIG. 20B. Accordingly, the dual chamber safe injection system is ready to inject as depicted in FIG. 20B. From the configuration depicted in FIG. 20B, further user pressure on the plunger manipulation interface (128) injects the sensitive medicine (132) through the needle distal end (48) and collapses the proximal medicine chamber (42), as shown in FIG. 20C. Moving from FIG. 20C to FIG. 20D, the needle spine assembly (76) is retracted into the syringe body (34) and at least partially into the plunger assembly (44) as described in U.S. patent application Ser. Nos. 14/696,342 and 62/416,102, which were previously incorporated by reference herein. Therefore, time of the exposure of the sensitive medicine (132) to the metal of the needle spine assembly (76) is minimized to the time it takes to complete an injection.

While the dual chamber safe injection system depicted in FIGS. 20A-20D is configured for use with the syringe, similar systems can be configured for use with a cartridge containing sensitive medicine. While the dual chamber safe injection system depicted in FIGS. 20A-20D involves direct injection from the proximal medicine chamber (40), other systems may involve movement of the sensitive medicine from the proximal medicine chamber (40) to the distal medicine chamber (42) before injection, as shown in FIGS. 22A-22D.

Needle Latching Member

FIGS. 21A-21D depict the interaction between the latch groove (111) on the distal end of the transfer pipe (46) and a needle latching member (612) to prevent proximal movement of the needle spine assembly (76) (including the transfer pipe (46)) before injection is completed.

Figure 21A:
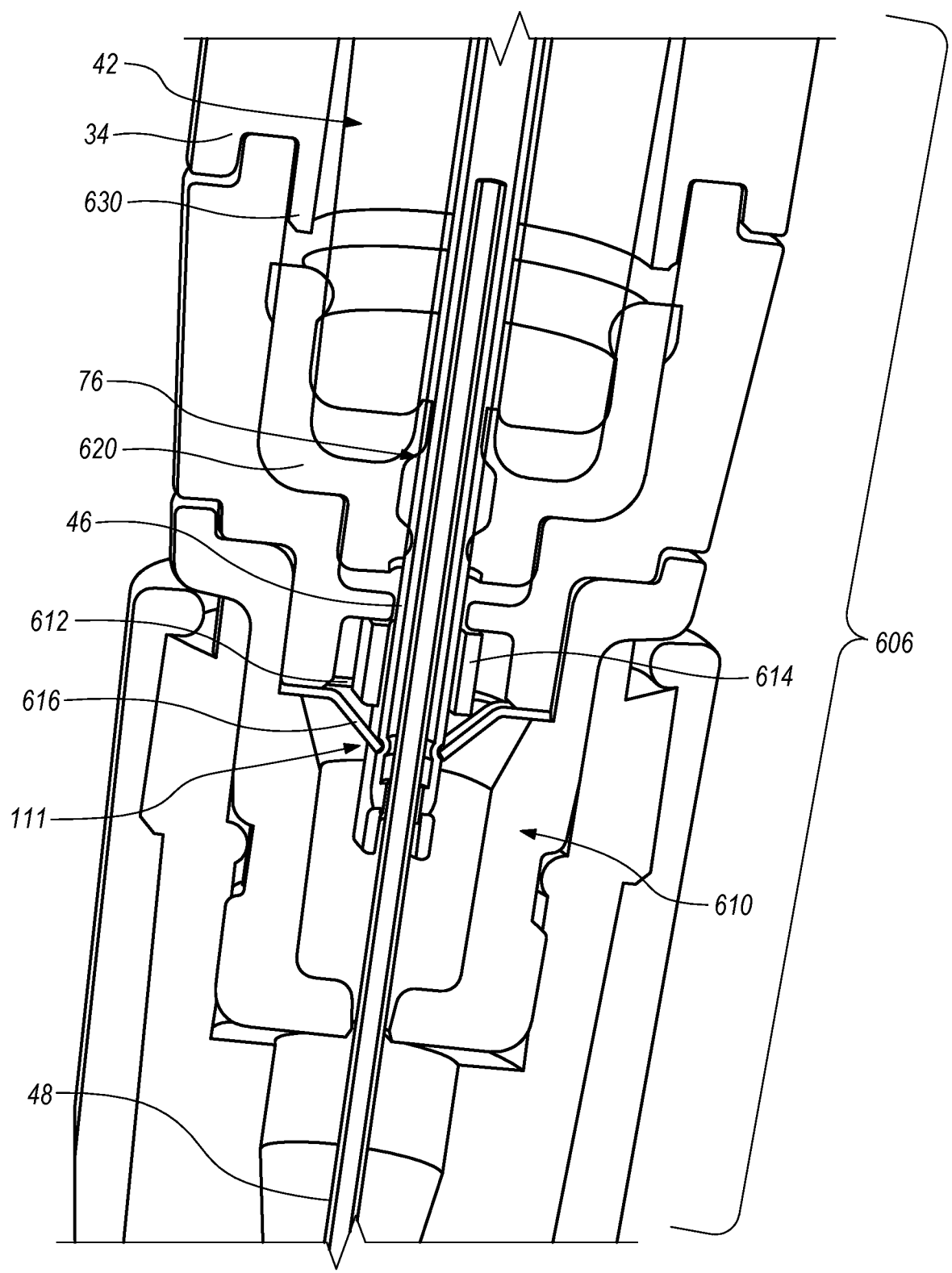
FIGS. 21A-21D illustrate a needle latching mechanism with adjustable force to unlatch the needle
Figure 21B:
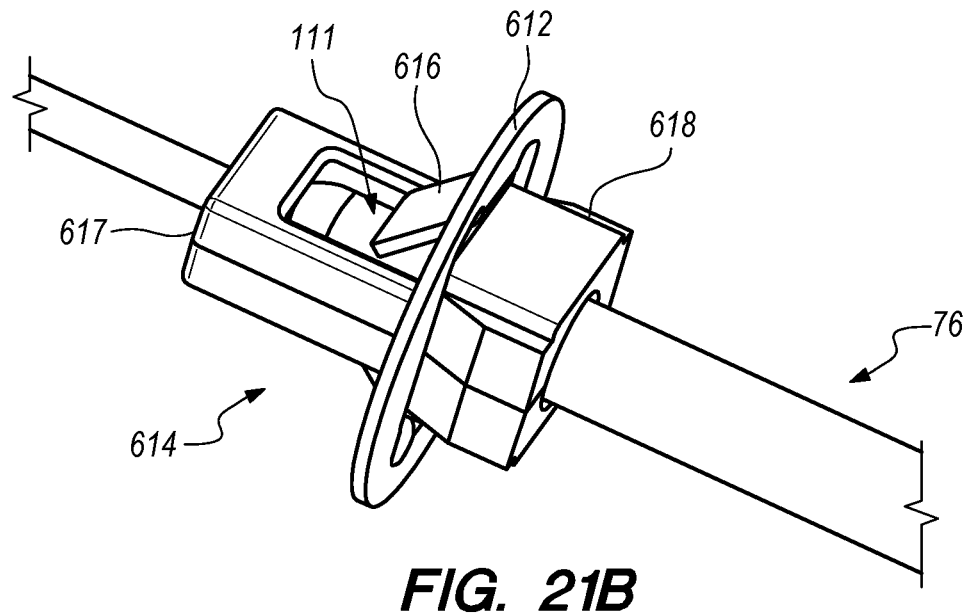
Figure 21C:
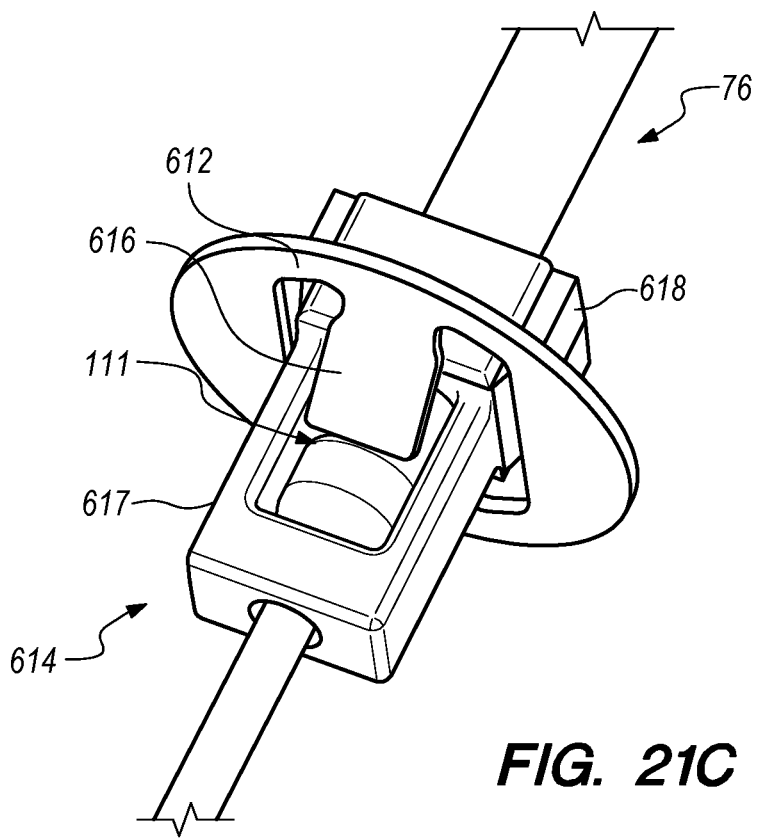
Figure 21D:
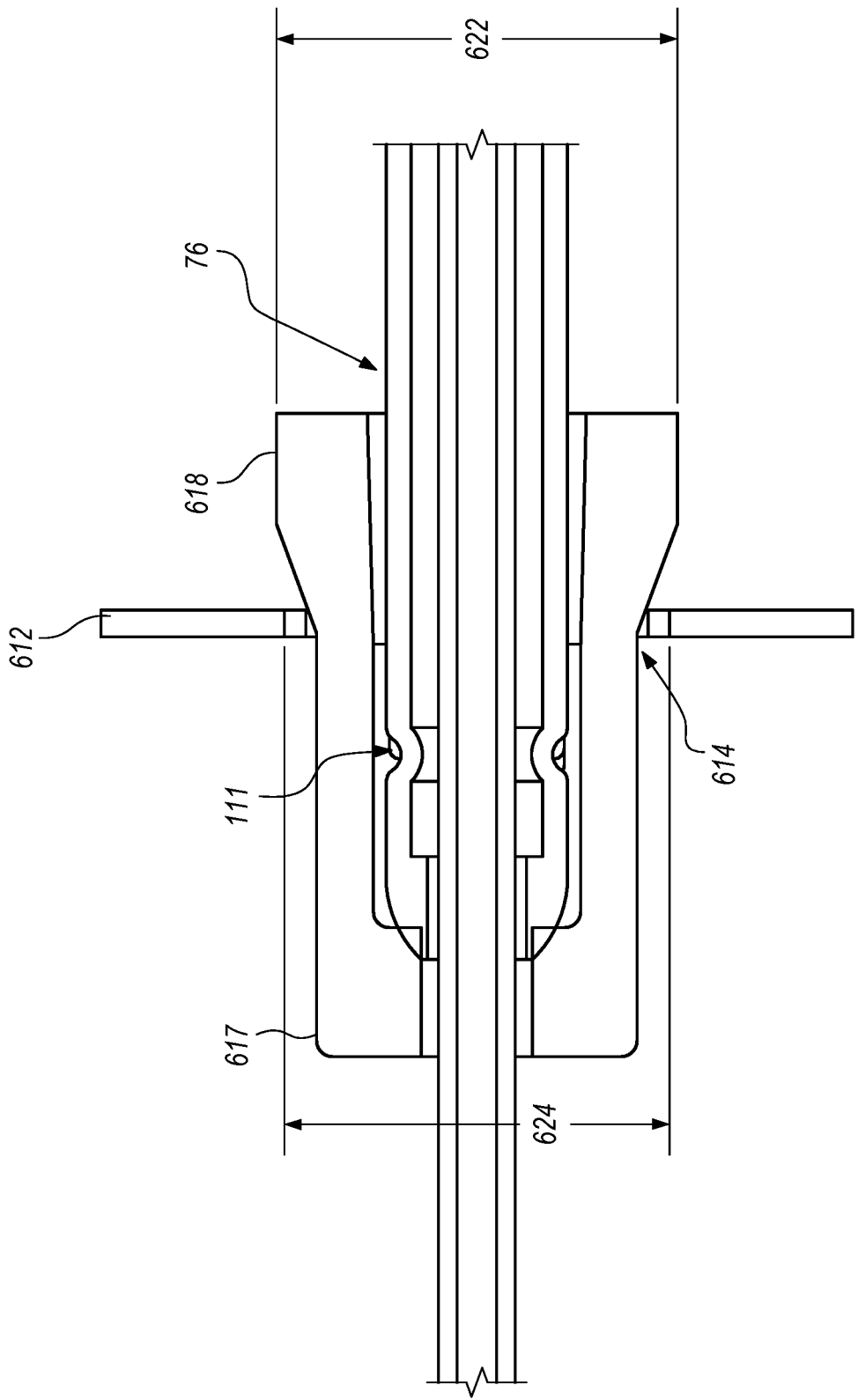
Figure 22A:
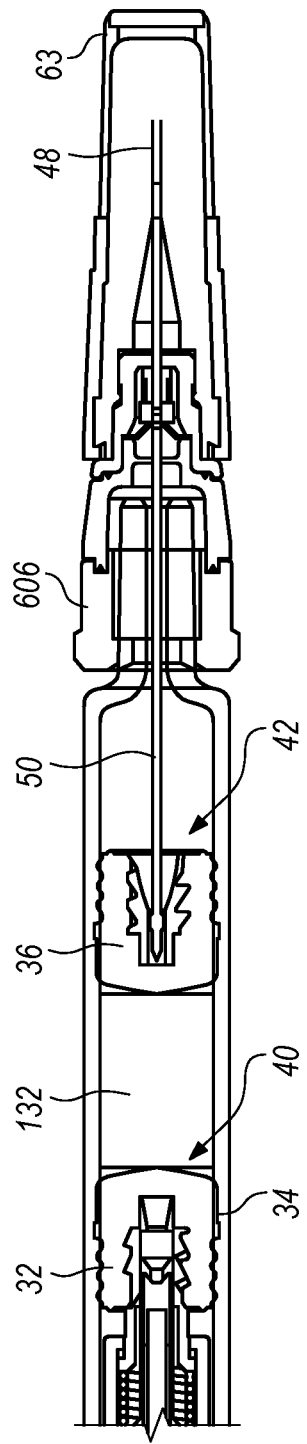
FIGS. 22A-22D illustrate an embodiment of the internal mechanism of a safe injection system for storage and delivery of a drug which is sensitive to contact with stainless steel.
Figure 22B:
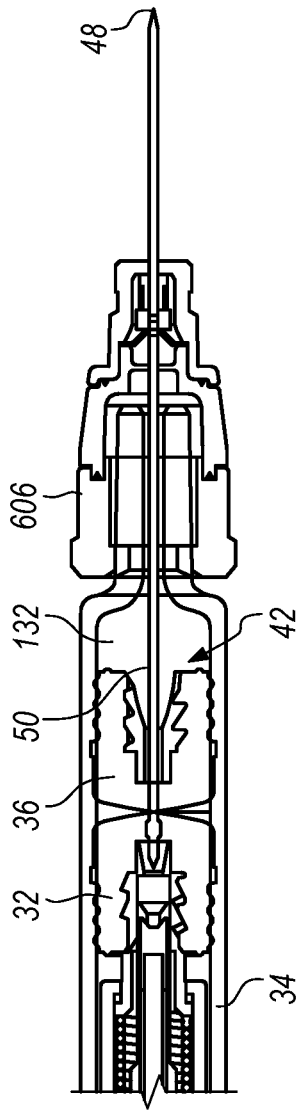
Figure 22C:
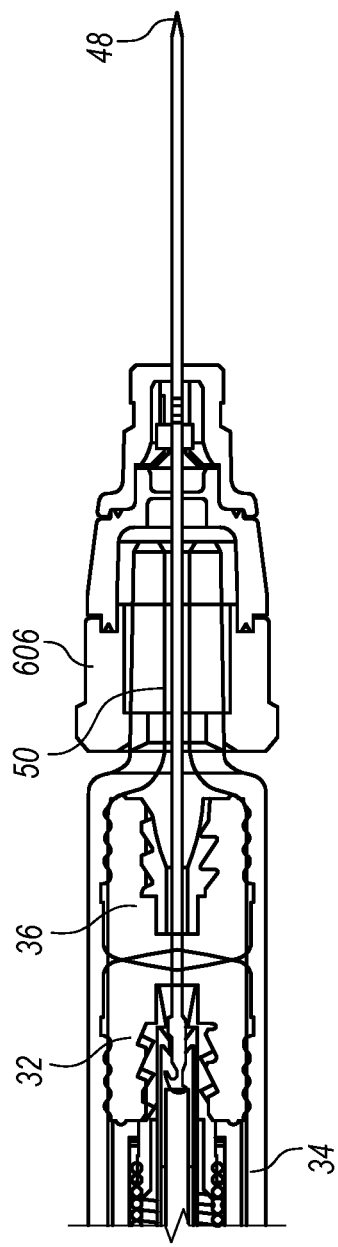
Figure 22D:
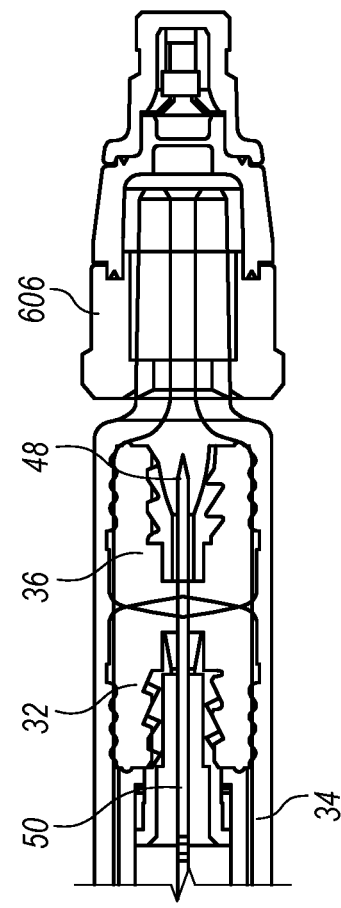

FIG. 21A shows a transfer pipe (46) with a latch groove (111) formed thereon and a proximal end of a distal needle end (48) inserted therein. In one embodiment, the proximal end of the distal needle end (48) may be the proximal end of the Luer needle, as described above. The transfer pipe (46) has a necked-down or radially-reduced latch groove (111) that is configured to interface with a latching member (612) and movable block member (614) such that during system assembly and use (e.g., mixing and injection), the needle spine assembly (76), including the transfer pipe (46), remains fixed in position relative to the syringe body (34), but after complete insertion of the plunger assembly relative to a small diameter flange (33—see, for example, FIG. 7N) (i.e., near or after full expulsion of the medicine which may be contained within the distal medicine chamber 42 of the syringe body 34), the needle spine assembly (76) is forced distally by the advancement of the plunger, advancing the movable block member (614) relative to the distal housing portion (610) such that the plurality (two are illustrated) of cantilevered latch members (616) of the latch member (612) are urged out of the way by the movable block member (614) to allow the needle spine assembly (76) (i.e., the needle distal end (48), transfer pipe (46), and proximal end (50)) to be retracted, thereby placing the needle distal end (48) safely within the plunger assembly (44). Alternatively, the needle distal end (48) may be retracted to a position below the outer surface of the distal housing portion (610) to safely protect the sharp point from the user. In other words, the cantilevered latch members (616) retain the position of the needle distal end (48) during injection and needle/syringe assembly, until they are pushed out of the way by the movable block member (614) at full plunger insertion (see FIG. 21D), after which the needle is free to be withdrawn as U.S. patent application Ser. Nos. 14/696,342 and 62/416,102, which were previously incorporated by reference herein.

The movable block member (614) includes a smaller distal portion (617) and a larger proximal portion (618) to increase the force needed to unlatch the needle spine assembly (76). The larger proximal portion (618) is configured to create a block outer diameter (622) dimension that will interfere with the inner diameter (624) of the latch (612) to increase the force to slide the movable block, thus increasing the force to unlatch the needle.

reduces the torque applied to the cantilevered latch members (616), thereby increasing the force needed to unlatch.

Vacuum Assisted Dual Chamber Safe Injection System

FIGS. 23-34 depict various aspects of a vacuum assisted dual chamber safe injection system similar to the ones depicted in FIGS. 6A-10B. The dual chamber safe injection system has a conventional off-the-shelf pre-filled syringe body (34) with proximal and distal stopper members (32, 36) disposed therein. The proximal and distal stopper members (32, 36) together with the syringe body (34) define proximal and distal medicine chambers (40, 42). The proximal and distal stopper members (32, 36) occlude the proximal and distal ends of the proximal medicine chamber (40). The distal stopper member (36) occludes a proximal end of the distal medicine chamber (42). The dual chamber safe injection system controls transfer of a first medicine component from the proximal medicine chamber (40) to the distal medicine chamber (42) and exit of a mixed/combined medicine from the distal medicine chamber (42) distally subject to sequential insertion of a plunger assembly relative to the syringe body (34) to various degrees by a user. The plunger assembly includes the proximal stopper member (32), a plunger housing member (69) and a plunger manipulation interface (128). The first medicine component located in the proximal medicine chamber (40) may be a liquid such as aqueous or oil based medicine solutions, a gel, or the first medicine component may be a diluent for mixing with the second medicine component in the distal medicine chamber (42). The second medicine component in the distal medicine chamber (42) may be a dry form medicine such as a powder, microspheres, emulsion, lyophilized or freeze dried medicine, or a cake like solid medicine. The second medicine component in the distal medicine chamber (42) may also be a liquid that mixes with the first medicine component from the proximal medicine chamber (40).

Figure 23:
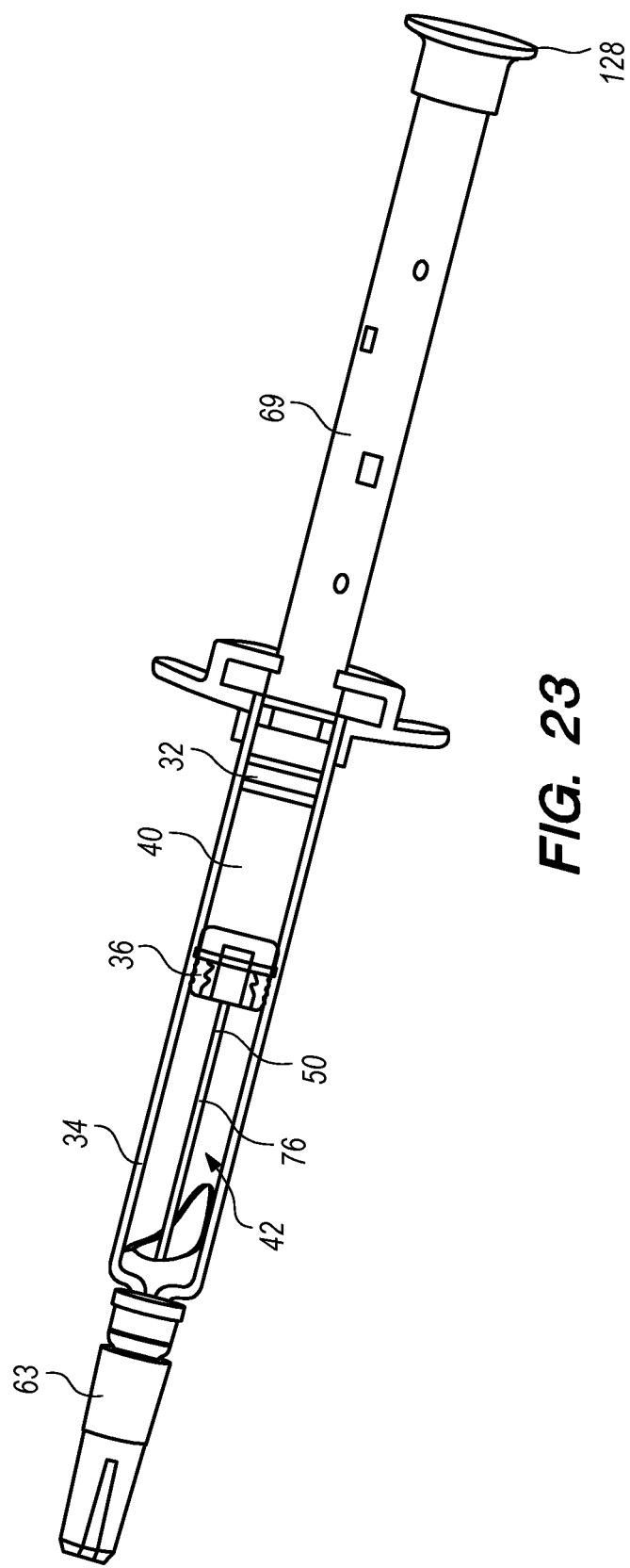
FIGS. 23-34 illustrate various aspects of vacuum assisted dual chamber safe injection systems wherein a distal needle end/tip may be withdrawn into a protected configuration after use according to various embodiments, including exemplary distal stopper bushings for use therein, which are shown in FIGS. 25, 26, and 34.

As described above, the dual chamber safe injection system proximal and distal stopper members (32, 36) are configured to be pierced by proximal needle end (50) at an appropriate time to assist with medication transfer. FIG. 23 illustrates a pre-utilization assembly with a needle cover (63) in place to mechanically isolate the distal needle end (48). The needle cover (63) may be removed and the assembly readied for injection into a patient. In some embodiments (not shown), the needle cover member (63) includes a vent (not shown) for allowing pressure resulting from the transfer and mixing of the medicine components to escape from inside the syringe body (34) while preventing contamination from entering the syringe body (34). However, such vented needle cover members are not always desirable.

Without venting, pressure builds in the distal medicine chamber (42) as the first medicine component is transferred under pressure from the proximal medicine chamber (40) to the distal medicine chamber (42). Pressure build up in the distal medicine chamber (42) may cause liquid (e.g., the mixed medicine) to be expelled from the distal medicine chamber (42) (e.g., through the needle distal end (48) before injection.

Accordingly, the vacuum assisted dual chamber safe injection system depicted in FIG. 23 includes a partial vacuum (e.g., 0.1 ATM or 90% vacuum) in the distal medicine chamber (42) before transfer of liquid from the proximal medicine chamber (40). The partial vacuum assists transfer of liquid from the proximal medicine chamber (40). For instance, after a portion of the transfer pipe (46) is pushed through the proximal stopper member (32) such that a proximal opening (270, see FIG. 29) is disposed in the proximal medicine chamber (40), the partial vacuum in the distal medicine chamber (42) draws liquid from the proximal medicine chamber (40) into the distal medicine chamber (42). The partial vacuum reduces the amount of distally directed force that must be applied to the proximal stopper member (32) via the plunger assembly to transfer the liquid from the proximal medicine chamber (40) into the distal medicine chamber (42). Transferring the liquid also at least partially releases the vacuum in the distal medicine chamber (42).

Figure 24:
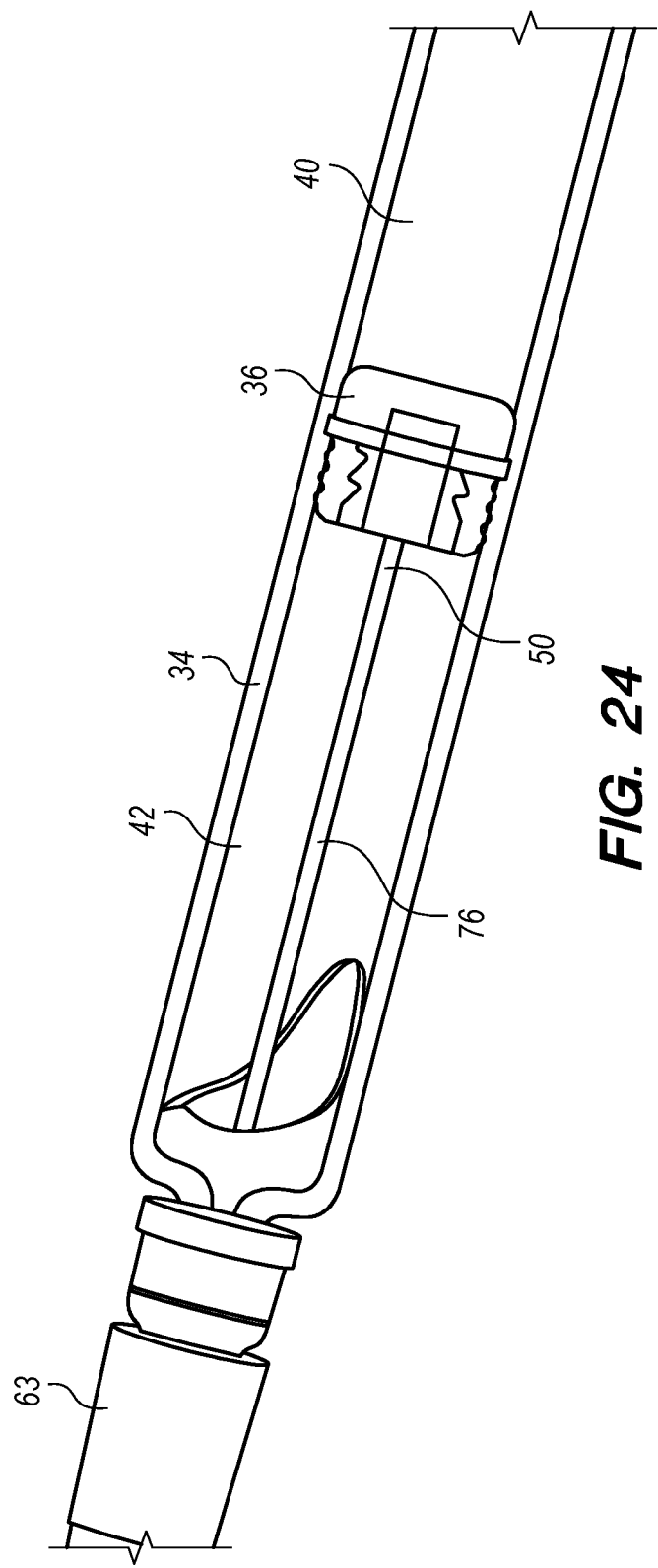

As shown in FIG. 24, the partial vacuum in the distal medicine chamber (42) produces a force ("Fv") on the distal stopper member (36), which must be temporarily resisted to maintain the dual chamber safe injection system in its transport/storage/pre-mixing configuration. The distally directed force (Fv) on the distal stopper member (36) is approximately the difference between the pressure in the proximal medicine chamber (40) and the pressure in the distal medicine chamber (42) multiplied by the area of the distal stopper member (36). In one embodiment:

pressure in the proximal medicine chamber (40)=1 ATM=14.7 psi pressure in the distal medicine chamber (42)=0.1 ATM=0.15 psi area of distal face of standard 3 cc stopper=0.09 in$^2$ force (Fv) on distal stopper member (36)=0.09(14.7−0.15)=1.31 lbs The resistance of the distal stopper member (36) to puncture by the harpoon coupling interface (not shown) may be sufficient to overcome the 1.31 lbs of force (Fv). However, with a sharper harpoon coupling interface or a less puncture resistant distal stopper member (36), the partial vacuum in the distal medicine chamber (42) may result in premature puncture of the distal stopper ember (36) by the harpoon coupling interface and even premature transfer of liquid from the proximal medicine chamber (40) into the distal medicine chamber (42).

Figure 25:
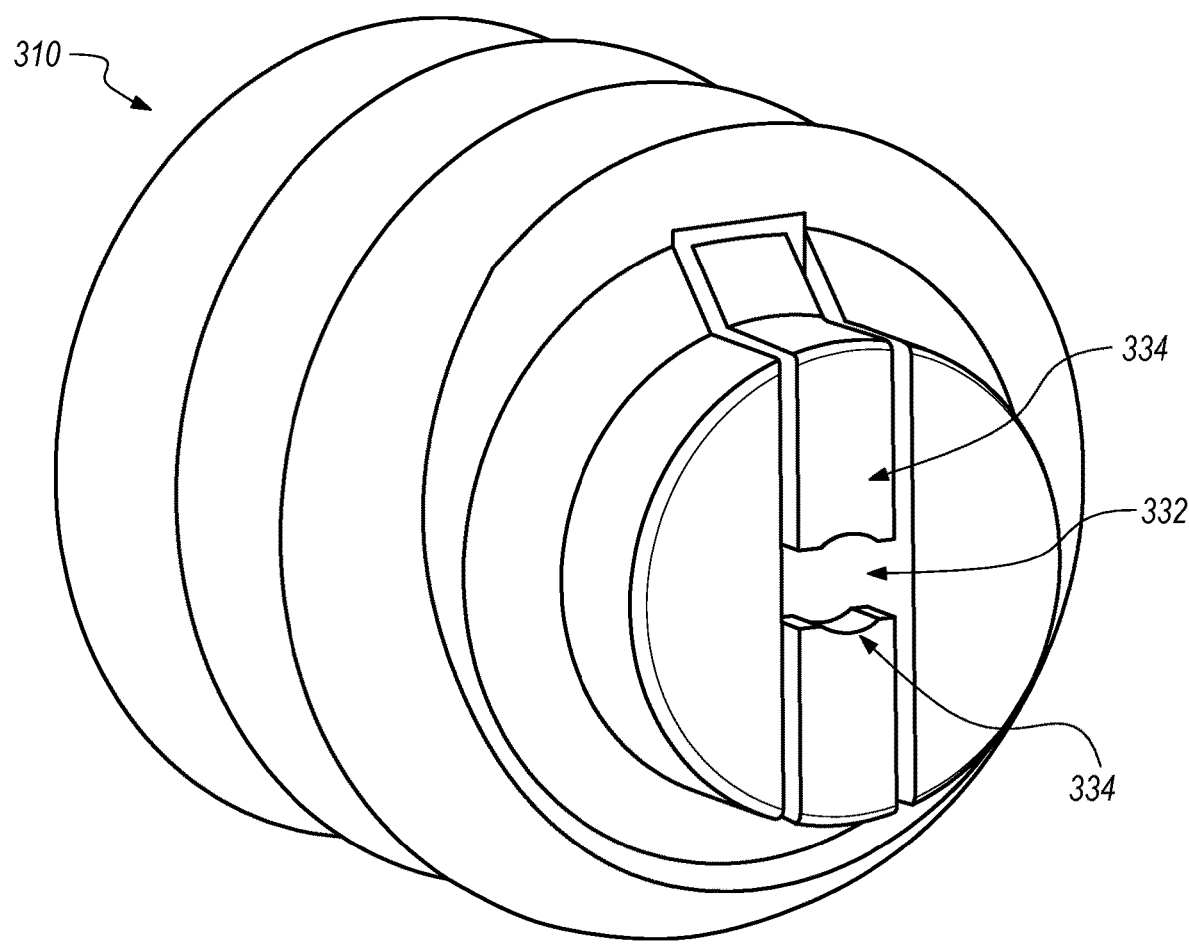
Figure 26:
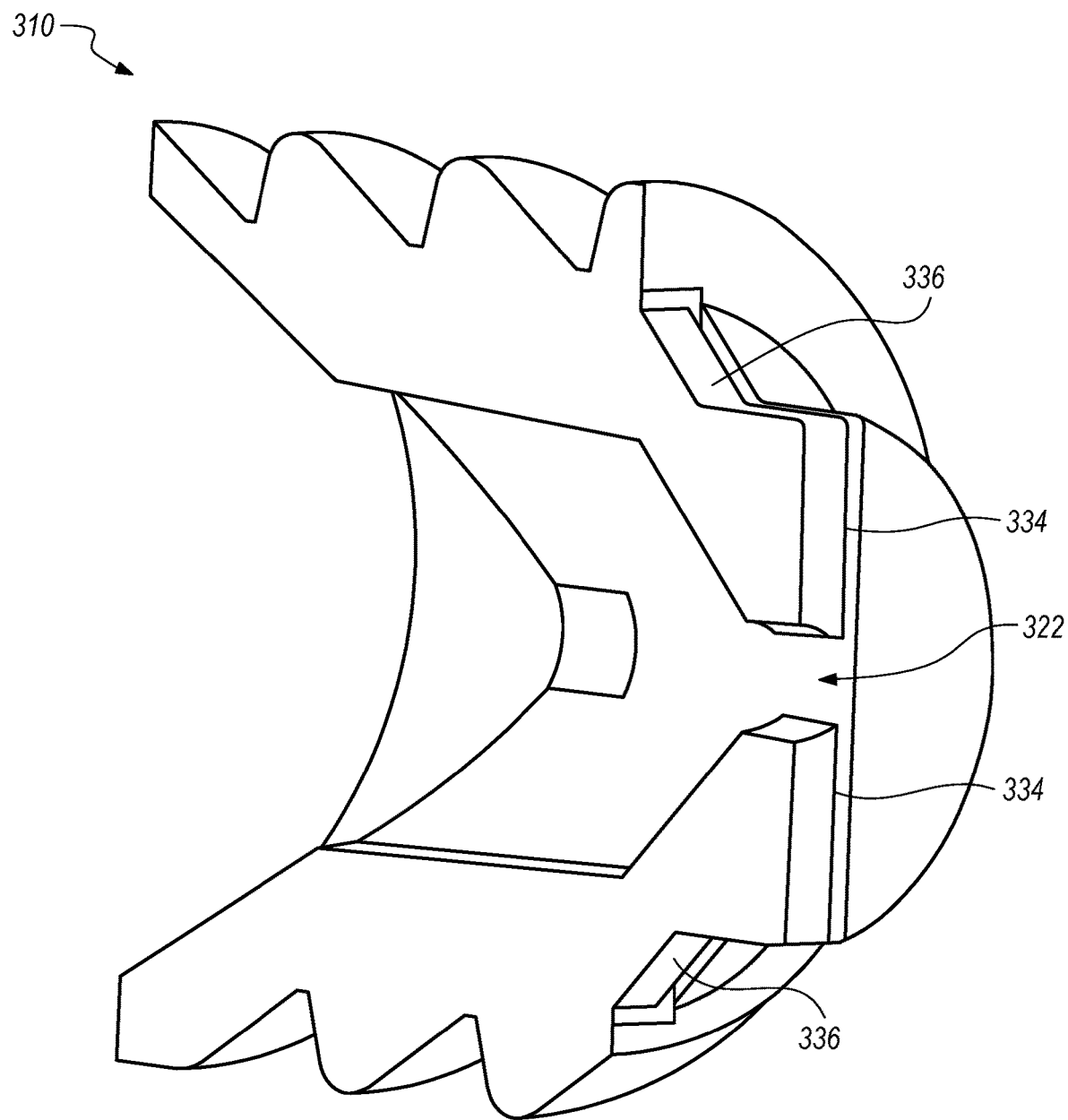

FIGS. 25 and 26 depict a distal stopper bushing (310) which includes a proximal gate (332). The distal stopper bushing (310) is configured to be screwed into the distal end of the distal stopper member (36). The proximal gate (332) includes a pair of movable arms (334), which are biased toward each other by respective spring elements (336). As such, the proximal gate (332) has two configurations: a closed configuration, in which the harpoon coupling interface cannot pass through the proximal gate (332); and an open configuration, in which the harpoon coupling interface can pass through the proximal gate (332). In the open configuration, the movable arms (334) are forced apart from each other (e.g., by relative movement of the harpoon coupling interface and the distal stopper member (36) to open the gate (332), as shown below).

Figure 27:
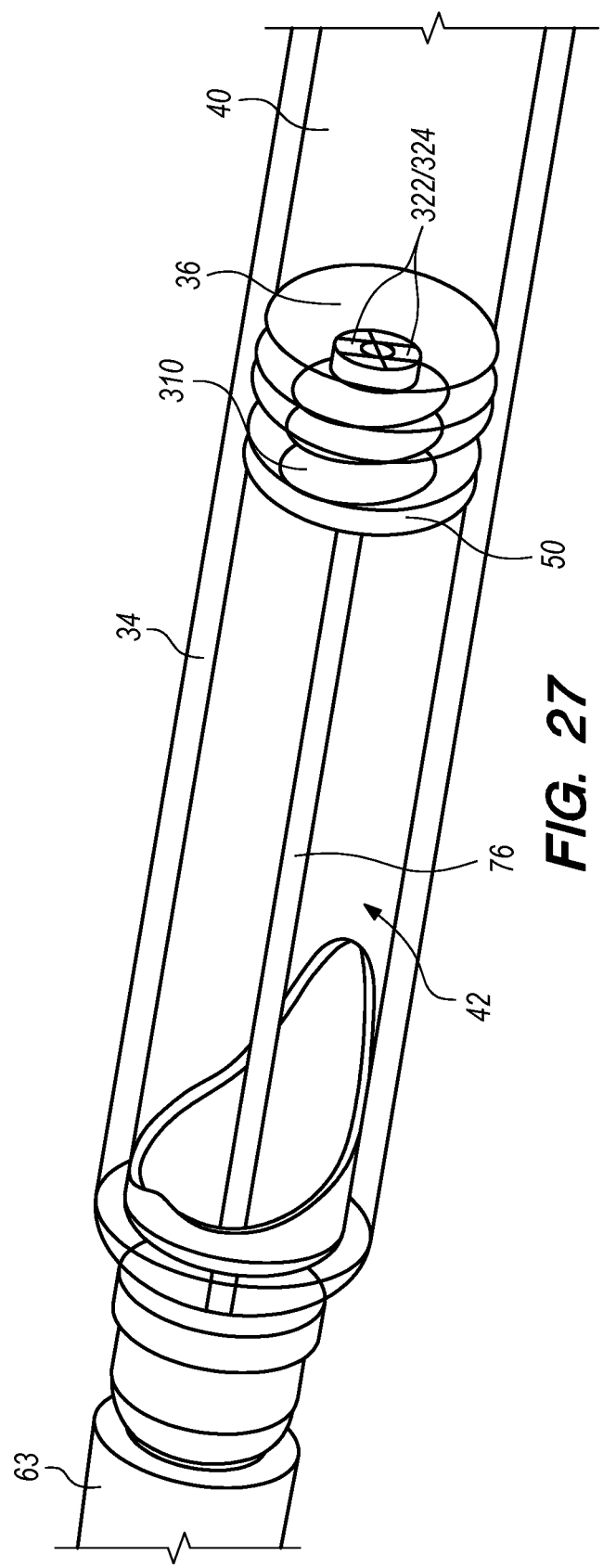
Figure 28:
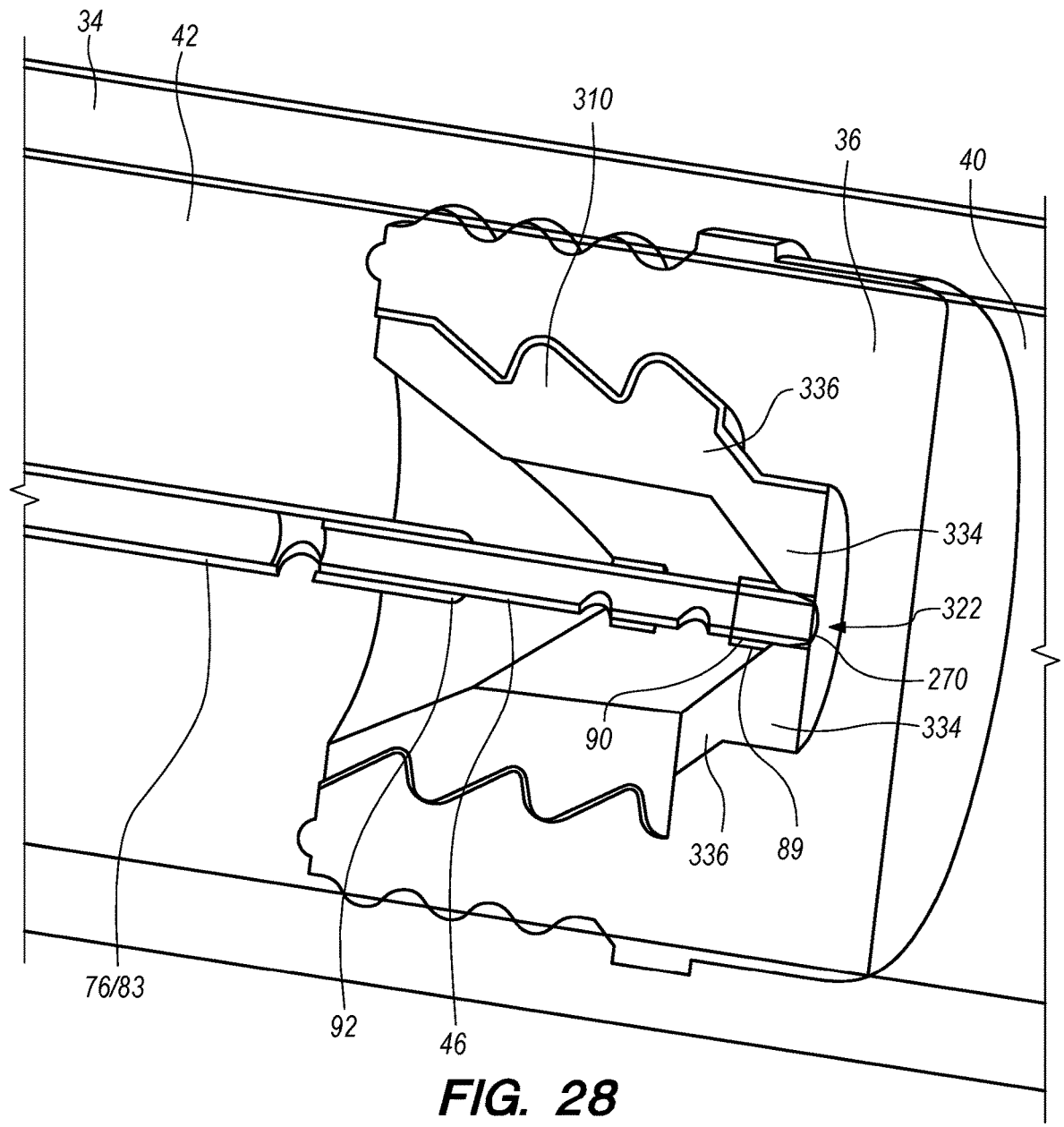

When the dual chamber injection system is in the transport/storage/pre-mixing configuration (see FIGS. 23, 24, 27, and 28) the gate (332) is in the closed configuration. The closed gate transfers the force (Fv) generated by the partial vacuum in the distal medicine chamber (42) to the harpoon coupling interface and the needle spine assembly (76) without piercing the distal stopper member (36), because the closed gate (322) prevents the harpoon coupling interface from contacting the distal stopper member (36), as shown in FIGS. 27 and 28. The harpoon coupling interface (89, see FIG. 28) includes a proximal shoulder (90) that interferes with the closed gate (322) to prevent the harpoon coupling interface (89) from passing therethrough. The harpoon coupling interface (89) has a hollow 3D arrowhead shape as described in U.S. Utility patent application filed on Nov. 1, 2017 and, entitled "SYSTEM AND METHOD FOR SAFETY SYRINGE," the disclosure of which has been previously incorporated by reference herein.

Figure 29:
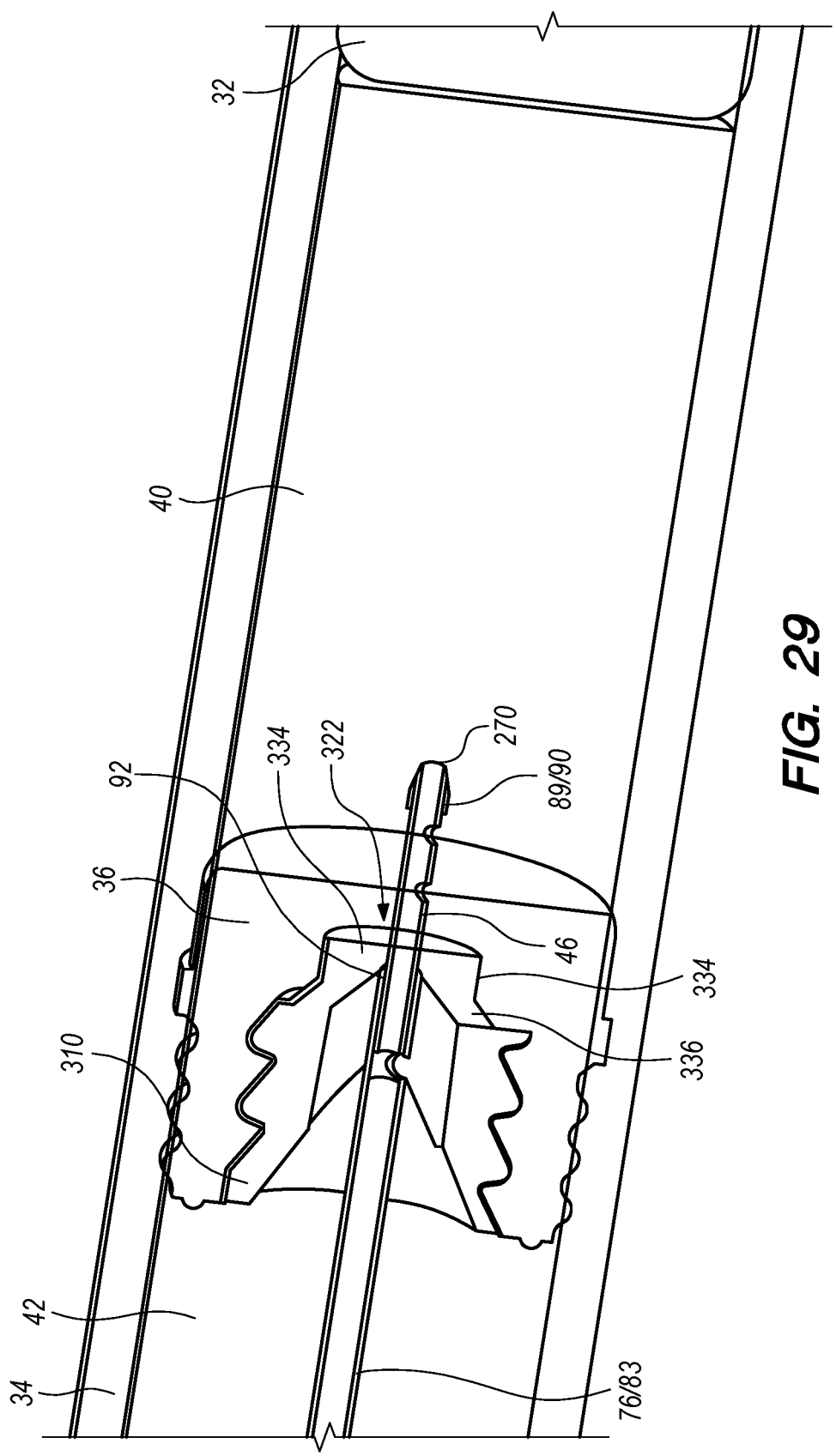

After a sufficient amount of distally directed force has been applied to plunger assembly, the distally directed force applied to the plunger, with the force (Fv) on distal stopper member (36) from the partial vacuum in the distal medicine chamber (42), overcomes the bias of the spring elements (336) in the arms (334) of the gate (332) to move the gate (332) from the closed configuration to the open configuration. Then the harpoon coupling interface (89) pierces the distal stopper member (36) partially followed by the transfer pipe (46), as shown in FIG. 29. Because the transfer pipe (46) has a smaller outer diameter than the distal end of the harpoon coupling interface (89), the gate (332) closes after proximal end of the harpoon coupling interface (89) pass therethrough.

Movement of the needle spine assembly (76) through the distal stopper member (36) is then temporarily halted by a distal shoulder (92) formed on the needle joining member (83) on the needle spine assembly (76), which has a larger outer diameter than the transfer pipe (46). The distal shoulder (92) will not pass through the closed gate (322), thereby holding the needle spine assembly (76) and the distal stopper member (36) in the position depicted in FIG. 29. In this position, the transfer pipe (46) spans the distal stopper member (36) and allows transfer of liquid therethrough. The partial vacuum in the distal medicine chamber (42) and the distally directed force has been applied to plunger assembly pull and push the liquid from the proximal medicine chamber (40) to the distal medicine chamber (42). Mechanical interference between the distal shoulder (92) and the closed gate (322) minimizes movement of the distal stopper member (36) during liquid transfer.

Figure 30:
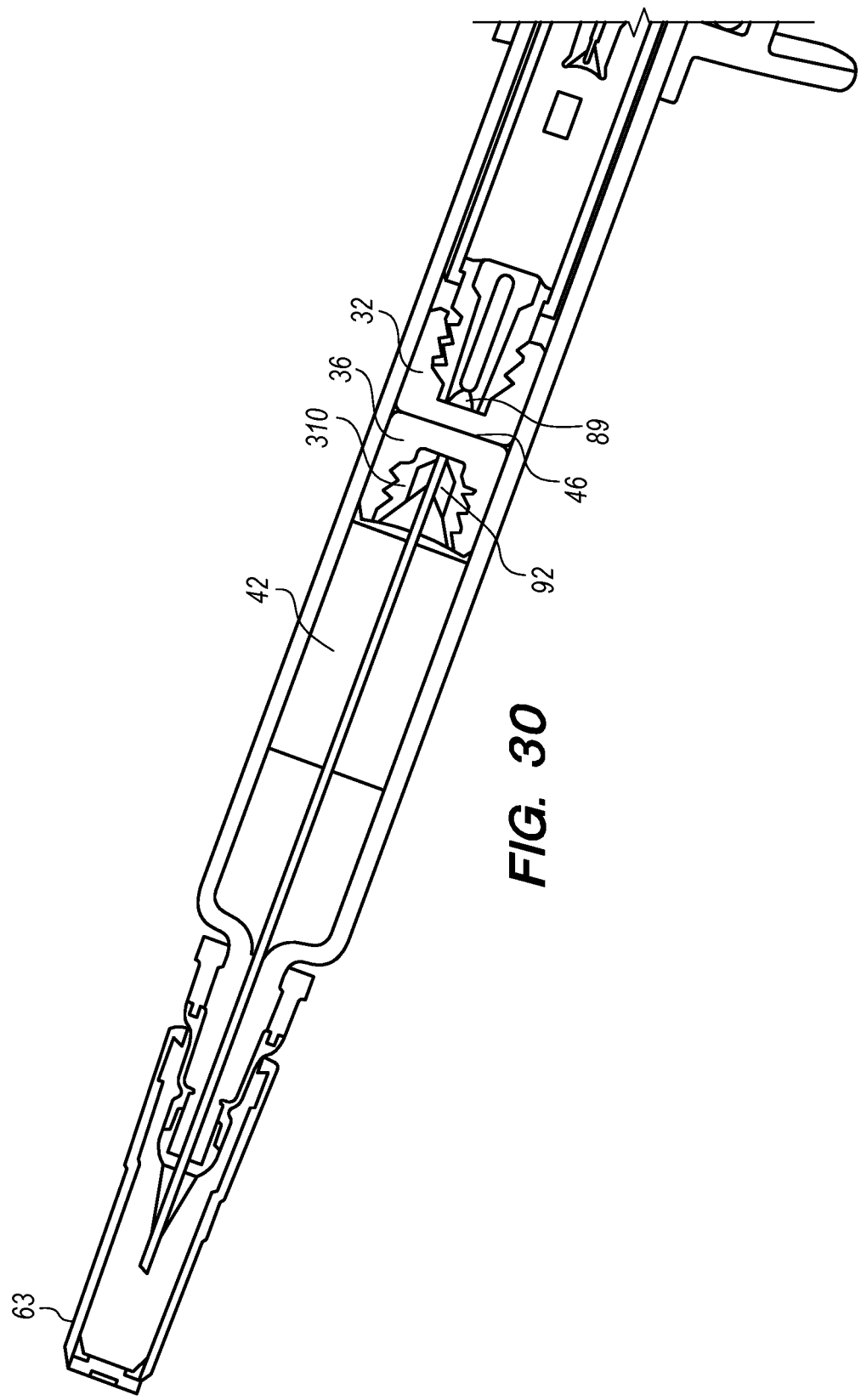

FIG. 30 depicts a configuration of the dual chamber safe injection system after liquid transfer from the proximal medicine chamber (40) to the distal medicine chamber (42) is substantially complete. The proximal stopper member (32) seals opening in the harpoon coupling interface (89, see FIG. 29) and the transfer pipe (46, see FIG. 29), stopping the liquid transfer. The partial vacuum in the distal medicine chamber (42) provides a space in the distal medicine chamber (42) after liquid transfer to allow the user to mix first and second medicine components by agitating the components.

Figure 31:
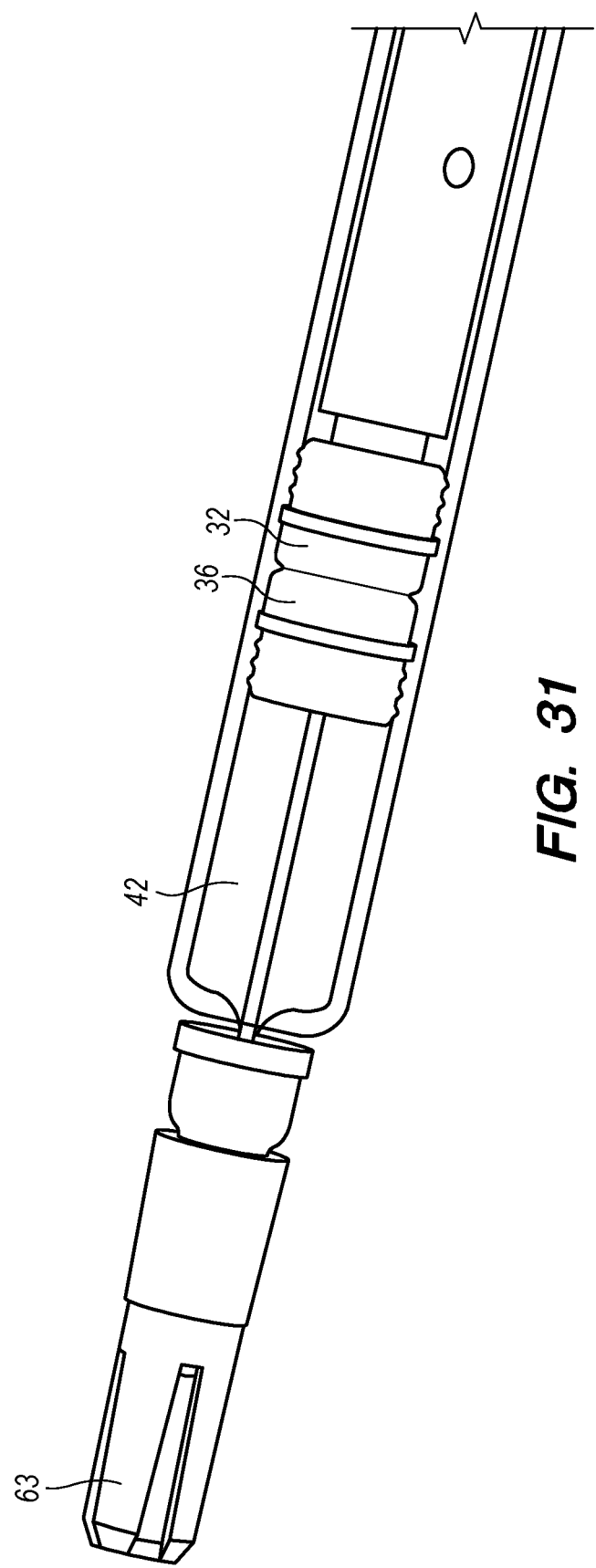

FIG. 31 depicts a configuration of the dual chamber safe injection system after sufficient distally directed force has been applied to plunger assembly to overcome the mechanical interference between the distal shoulder (92, see FIG. 29) and the closed gate (322, see FIG. 29) (i.e., by opening the gate (322)). After the distal and proximal stopper members (36, 32) are no longer prevented from moving distally by the distal shoulder (92, see FIG. 29) and the closed gate (322, see FIG. 29), the partial vacuum collapses the space by moving the distal and proximal stopper members (36, 32) distally. Distally directed force applied to plunger assembly may also assist in collapsing the space in the distal medicine chamber (42) (compare FIGS. 30 and 31).

After the partial vacuum collapses the space in the distal medicine chamber (42), the distal medicine chamber may include a small air bubble that does not need to be purged before injection. Accordingly, vacuum assisted dual chamber safe injection systems can function without purging unlike other injection systems. Consequently, the vacuum assisted dual chamber safe injection systems described herein can be used with auto injectors, pens, and other "reusable" or "disposable" housing interfaces without purging.

Figure 32:
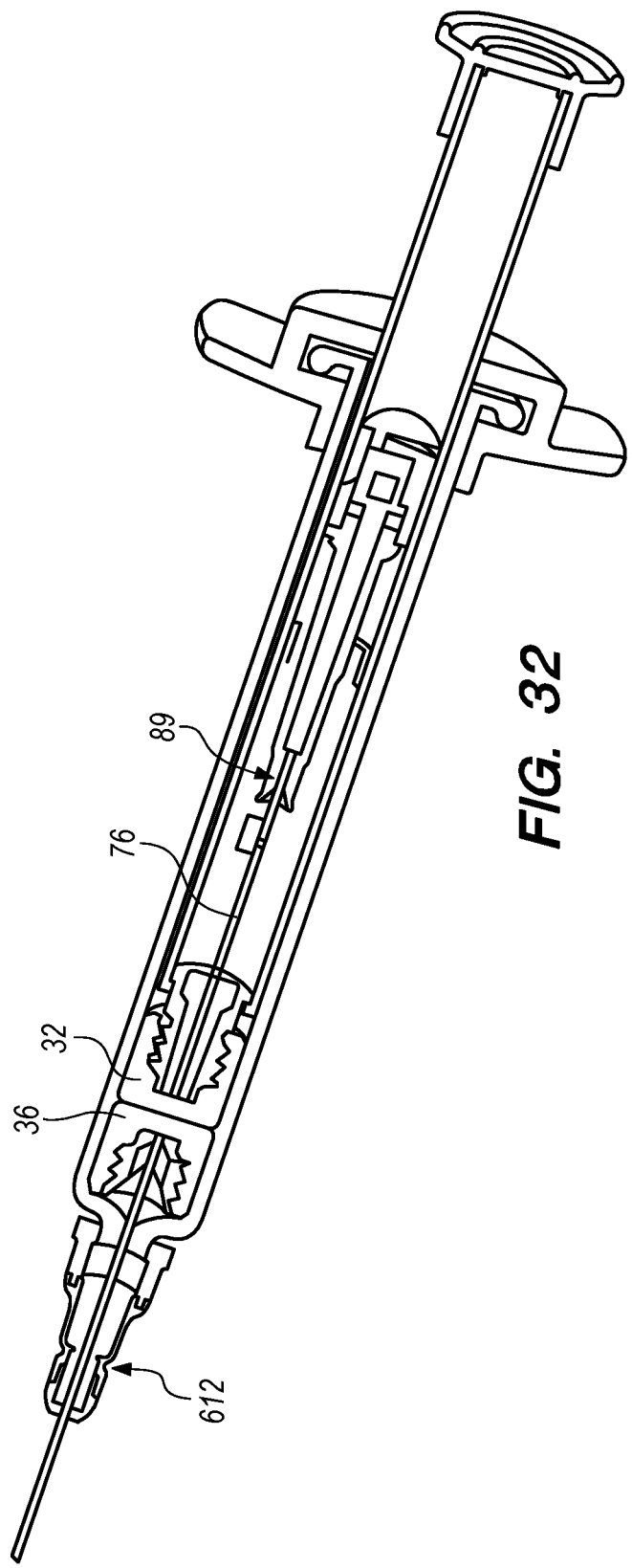

FIG. 32 depicts a configuration of the dual chamber safe injection system after the needle-latching member (612) has been disengaged from the needle spine assembly (76) and the harpoon coupling interface (89) has been secured to the needle retention feature, as described above. The energy storage member has been omitted from FIG. 32 for clarity.

Figure 33:
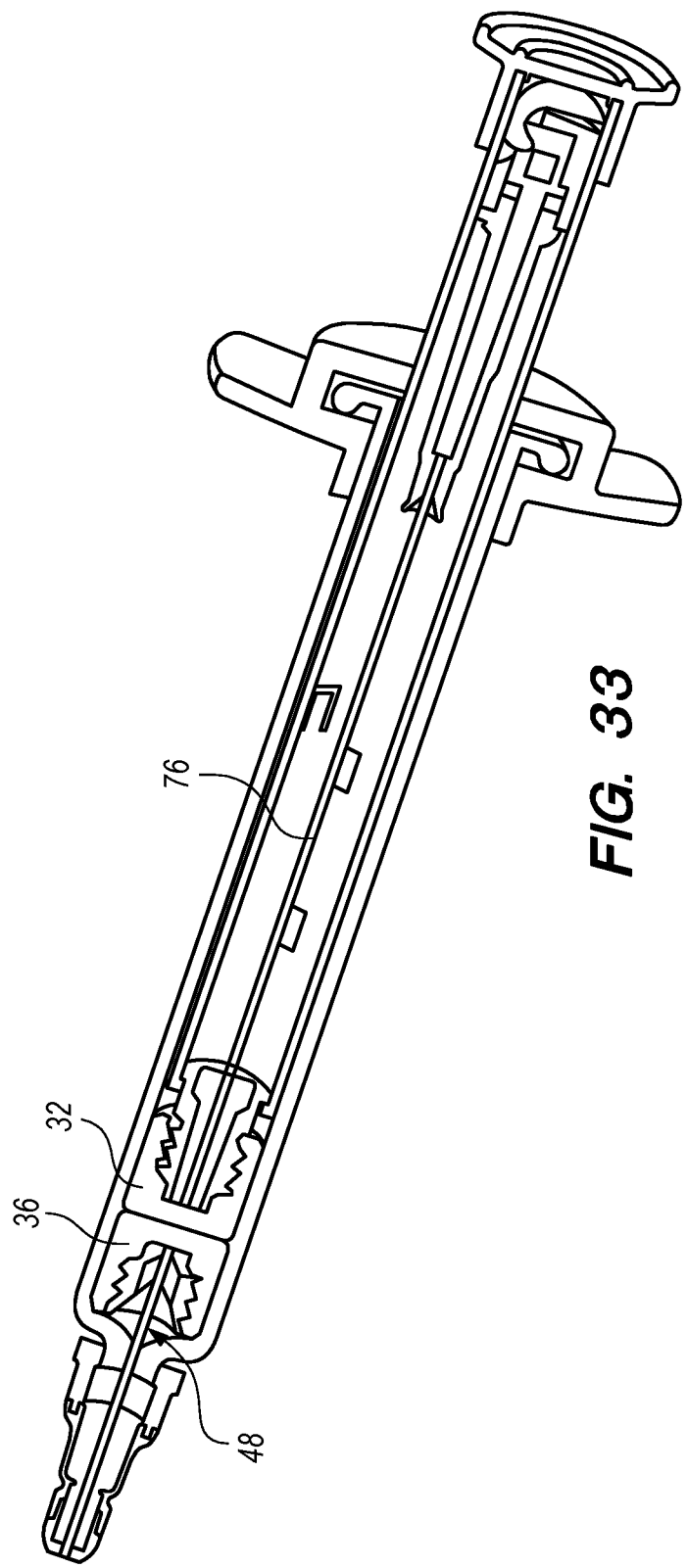

FIG. 33 depicts a configuration of the dual chamber safe injection system after a retraction mechanism has been triggered to retract the needle spine assembly (76) proximally relative to the syringe body (34) until the sharp end of the needle distal end (48) is in a safe position at least in the needle hub, as described above. The energy storage member has been omitted from FIG. 33 for clarity.

Figure 34:
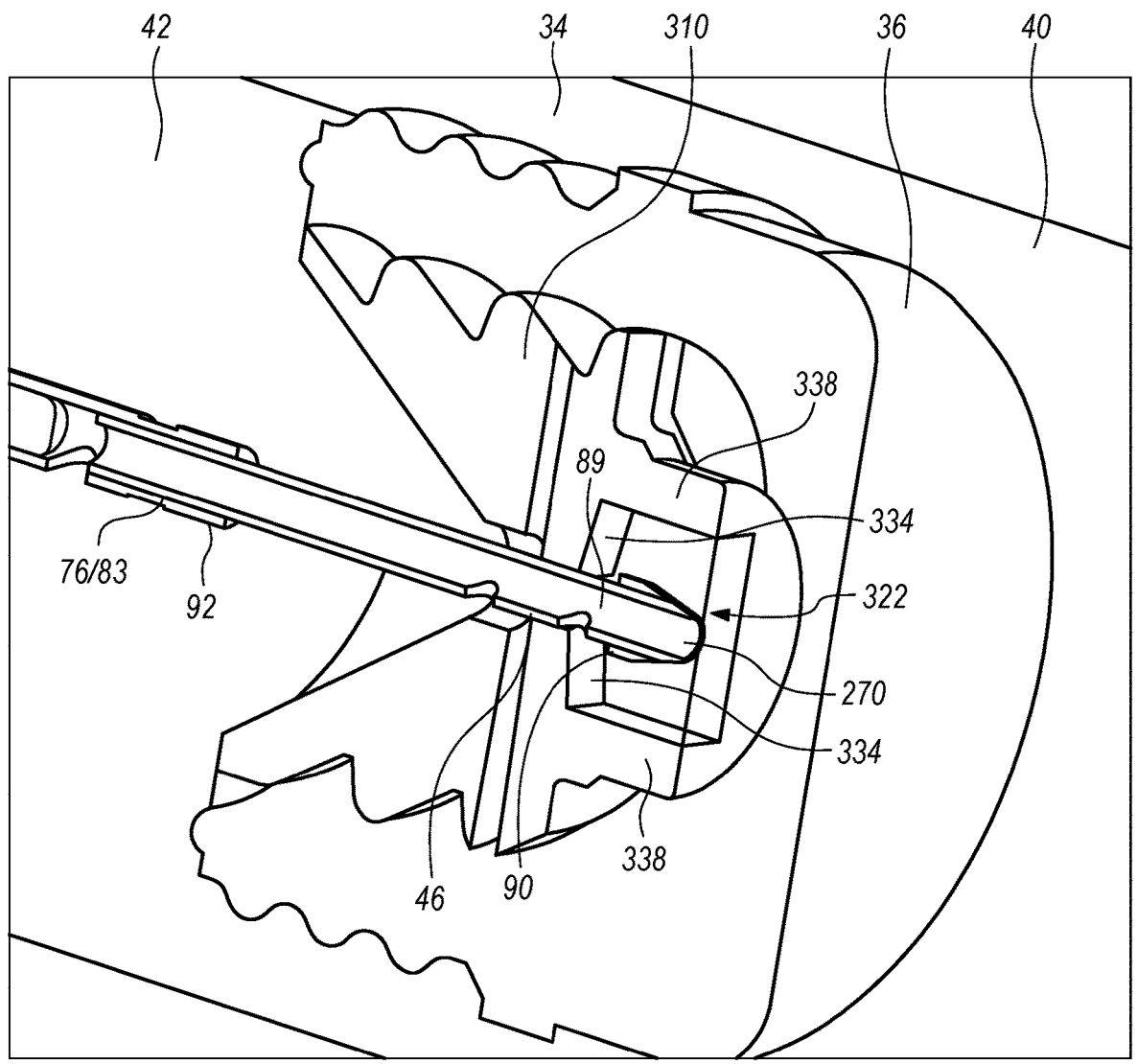

FIG. 34 depicts a distal stopper bushing (310) which includes a proximal gate (332) according to another embodiment. The difference between the distal stopper bushing (310) in FIG. 34 and the distal stopper bushing (310) in FIGS. 25-28 is the design of the proximal gate (332). In the proximal gate (332) depicted in FIG. 34, the pair of movable arms (334) rotate about respective self-energizing hinges (338) when the distal shoulder (92) presses against the movable arms (334) in the proximal direction. The force of the distal shoulder (92) on the movable arms (334) causes the arms to move closer to each other, thereby securing the transfer tube (46) to the movable arms (334). This secures the transfer tube (46) in an optimal position for liquid transfer. The position of the transfer tube (46) in the secured position can be adjusted by modifying the axial length of the self-energizing hinges (338) to adjust the force on the transfer tube (46) from the movable arms (334). After liquid transfer is complete, increased distally directed force on the plunger assembly overcomes the mechanical interference between the distal shoulder (92) and the closed gate (322) to allow for injection.

The vacuum assisted dual chamber safe injection system depicted in FIGS. 23-33 and described herein facilitate transfer of liquids from the proximal medicine chamber (40) to the distal medicine chamber (42) by pulling liquid into the distal medicine chamber (42) and by minimizing pressure buildup in the distal medicine chamber (42) with liquid transfer. The vacuum assisted dual chamber safe injection system also includes a distal stopper bushing (310) with a proximal gate (332) to prevent premature movement of the distal stopper member (36) caused by the partial vacuum in the distal medicine chamber (42).

Various exemplary embodiments of the invention are described herein. Reference is made to these examples in a non-limiting sense. They are provided to illustrate more broadly applicable aspects of the invention. Various changes may be made to the invention described and equivalents may be substituted without departing from the true spirit and scope of the invention. In addition, many modifications may be made to adapt a particular situation, material, composition of matter, process, process act(s) or step(s) to the objective(s), spirit or scope of the present invention. Further, as will be appreciated by those with skill in the art that each of the individual variations described and illustrated herein has discrete components and features which may be readily separated from or combined with the features of any of the other several embodiments without departing from the scope or spirit of the present inventions. All such modifications are intended to be within the scope of claims associated with this disclosure.

Any of the devices described for carrying out the subject diagnostic or interventional procedures may be provided in packaged combination for use in executing such interventions. These supply "kits" may further include instructions for use and be packaged in sterile trays or containers as commonly employed for such purposes.

The invention includes methods that may be performed using the subject devices. The methods may comprise the act of providing such a suitable device. Such provision may be performed by the end user. In other words, the "providing"

act merely requires the end user obtain, access, approach, position, set-up, activate, power-up or otherwise act to provide the requisite device in the subject method. Methods recited herein may be carried out in any order of the recited events which is logically possible, as well as in the recited order of events.

Exemplary aspects of the invention, together with details regarding material selection and manufacture have been set forth above. As for other details of the present invention, these may be appreciated in connection with the above-referenced patents and publications as well as generally known or appreciated by those with skill in the art. For example, one with skill in the art will appreciate that one or more lubricious coatings (e.g., hydrophilic polymers such as polyvinylpyrrolidone-based compositions, fluoropolymers such as tetrafluoroethylene, PTFE, hydrophilic gel or silicones) may be used in connection with various portions of the devices, such as relatively large interfacial surfaces of movably coupled parts, if desired, for example, to facilitate low friction manipulation or advancement of such objects relative to other portions of the instrumentation or nearby tissue structures. The same may hold true with respect to method-based aspects of the invention in terms of additional acts as commonly or logically employed.

In addition, though the invention has been described in reference to several examples optionally incorporating various features, the invention is not to be limited to that which is described or indicated as contemplated with respect to each variation of the invention. Various changes may be made to the invention described and equivalents (whether recited herein or not included for the sake of some brevity) may be substituted without departing from the true spirit and scope of the invention. In addition, where a range of values is provided, it is understood that every intervening value, between the upper and lower limit of that range and any other stated or intervening value in that stated range, is encompassed within the invention.

Also, it is contemplated that any optional feature of the inventive variations described may be set forth and claimed independently, or in combination with any one or more of the features described herein. Reference to a singular item, includes the possibility that there are plural of the same items present. More specifically, as used herein and in claims associated hereto, the singular forms "a," "an," "said," and "the" include plural referents unless the specifically stated otherwise. In other words, use of the articles allow for "at least one" of the subject item in the description above as well as claims associated with this disclosure. It is further noted that such claims may be drafted to exclude any optional element. As such, this statement is intended to serve as antecedent basis for use of such exclusive terminology as "solely," "only" and the like in connection with the recitation of claim elements, or use of a "negative" limitation.

Without the use of such exclusive terminology, the term "comprising" in claims associated with this disclosure shall allow for the inclusion of any additional element—irrespective of whether a given number of elements are enumerated in such claims, or the addition of a feature could be regarded as transforming the nature of an element set forth in such claims. Except as specifically defined herein, all technical and scientific terms used herein are to be given as broad a commonly understood meaning as possible while maintaining claim validity.

The breadth of the present invention is not to be limited to the examples provided and/or the subject specification, but rather only by the scope of claim language associated with this disclosure.

What is claimed is:

1. A system for mixing drug products and injecting, comprising: a cylindrical injection body defining a proximal opening and a distal needle interface at a distal end thereof; proximal and distal stopper members disposed in the cylindrical injection body, forming a proximal drug chamber between the proximal and distal stopper members and a distal drug chamber between the distal stopper member and the distal end of the cylindrical injection body; a plunger member defining a plunger interior and configured to insert the proximal stopper member relative to the cylindrical injection body, the plunger member including a needle retention feature disposed in the plunger interior, an energy-storage member disposed in the plunger interior, and an energy-storage member latching member disposed in the plunger interior; and a needle hub assembly coupled to the distal needle interface of the cylindrical injection body, the needle hub assembly including a needle having a needle proximal end feature, a hub, and a needle latching member configured to couple the needle to the hub, wherein first and second sizes of the respective proximal and distal drug chambers can be modified by movement of the proximal and distal stopper members relative to the cylindrical injection body, wherein the needle is at least partially retractable into plunger interior upon insertion of the plunger member relative to the cylindrical injection body to transform the energy-storage member latching member from a latched state to an unlatched state, and wherein the distal stopper includes a funnel disposed at a distal end thereof, the funnel tapering in a proximal direction, such that an inner diameter of a distal end of the funnel is larger than an inner diameter of a proximal end of the funnel wherein the distal stopper member comprises a proximal gate having a closed configuration wherein the needle proximal end feature cannot pass through the proximal gate, and an open configuration wherein the needle proximal end feature can pass through the proximal gate.

2. The system of claim 1, wherein the needle is configured to pierce entirely through at least the distal stopper member to be retracted into the plunger interior.

3. The system of claim 1, wherein the proximal and distal drug chambers respectively contain first and second components of a drug to be mixed together prior to injecting into a patient.

4. The system of claim 1, wherein the proximal and distal stopper members each includes a respective opposing surface,
wherein the opposing surface of the proximal stopper member faces a distal direction, and
wherein the opposing surface of the distal stopper member faces a proximal direction, and
wherein the proximal and distal stoppers comprising respective first and second polymer coatings on respective opposing surfaces thereof, such that the proximal drug chamber is defined by the cylindrical injection body and the first and second polymer coatings.

5. The system of claim 1, wherein the distal drug chamber contains a partial vacuum.

6. The system of claim 1, wherein the proximal gate comprises a pair of movable arms operatively coupled to a pair of spring elements, the pair of spring elements biasing the proximal gate in the closed configuration.

7. The system of claim 1, wherein the proximal gate comprises a pair of movable arms operatively coupled to a pair of self-energizing hinges.

8. The system of claim 1, wherein the funnel is configured to receive the needle proximal end feature and guide the needle into coaxial alignment with the distal stopper member.

9. The system of claim 1, wherein the needle proximal end feature comprises a proximal shoulder that cannot past through the proximal gate in the closed configuration, but can pass through the proximal gate in the open configuration.

10. The system of claim 9, wherein the needle comprises a distal shoulder that cannot past through the proximal gate in the closed configuration, but can pass through the proximal gate in the open configuration, and wherein the distal shoulder is distal of the proximal shoulder.

11. The system of claim 1, wherein the system has
a transport configuration wherein the needle proximal end feature is disposed in the distal drug chamber,
a transfer configuration wherein the needle proximal end feature has at least partially pierced the distal stopper member and is at least partially disposed in the proximal drug chamber, and
a mixed configuration wherein the proximal and distal stopper members are in contact with each other, thereby transferring a first drug component from the proximal drug chamber to the distal drug chamber to mix the first drug component with a second drug component in the distal drug chamber.

12. The system of claim 11, the cylindrical injection body comprising a position indicator configured to be adjacent with a distal end of the distal stopper when the system is in the mixed configuration.

13. The system of claim 11, the plunger member comprising a retention clip configured to be selectively coupled to the cylindrical injection body when the system is in the mixed configuration to prevent proximal movement of the plunger member relative to the cylindrical injection body.

14. The system of claim 13, wherein the retention clip is configured to generate an audible signal when the retention clip is selectively coupled to the cylindrical injection body.

15. The system of claim 11, wherein the needle comprises:
a distal end opening;
a middle opening disposed in the distal drug chamber when the system is in the transport, transfer, and mixed configurations; and
a proximal opening disposed in the proximal drug chamber when the system is in the transfer configuration.

16. The system of claim 15, wherein the needle further comprises a plurality of proximal openings, the proximal opening being one of the plurality of proximal openings,
wherein at least some of the plurality of proximal openings are disposed in the proximal drug chamber when the system is in the transfer configuration, and
wherein at least some of the plurality of proximal openings are configured to be occluded by the proximal stopper member when the system is in the mixed configuration.

17. The system of claim 16, the proximal stopper member comprising a plug configured to occlude at least some of the plurality of proximal openings when the system is in the mixed configuration.

18. The system of claim 17, wherein a length of the plug is greater than a distance between a proximal most opening of the plurality of proximal openings and a distal most opening of the plurality of proximal openings.

19. A method for mixing and injecting medicine into a patient, comprising: providing a system comprising a cylindrical injection body defining a proximal opening and a distal needle interface at a distal end thereof, proximal and distal stopper members disposed in the cylindrical injection body, forming a proximal medicine chamber between the proximal and distal stopper members and a distal medicine chamber between the distal stopper member and the distal end of the cylindrical injection body, a plunger member defining a plunger interior and configured to insert the proximal stopper member relative to the cylindrical injection body, and a needle member having a distal needle tip, a medicine passage, a plurality of transfer openings, and a proximal end; and wherein the distal stopper includes a funnel disposed at a distal end thereof, the funnel tapering in a proximal direction, such that an inner diameter of a distal end of the funnel is larger than an inner diameter of a proximal end of the funnel; advancing the plunger member to pierce the proximal end of the needle member through the distal stopper to allow the passage of a first medicine component from the proximal medicine chamber through the medicine passage, and into the distal medicine chamber to allow mixing of the first medicine component with a second medicine component in the distal medicine chamber to form a mixed medicine; advancing the plunger member to inject the mixed medicine into a patient; and automatically retracting the distal needle tip into the cylindrical injection body when the mixed medicine has been injected into the patient wherein the distal stopper member comprises a proximal gate having a closed configuration wherein the needle proximal end feature cannot pass through the proximal gate, and an open configuration wherein the needle proximal end feature can pass through the proximal gate.

* * * * *